(12) United States Patent
Mickelsen

(10) Patent No.: US 11,426,573 B2
(45) Date of Patent: Aug. 30, 2022

(54) CATHETERS, CATHETER SYSTEMS, AND METHODS FOR PUNCTURING THROUGH A TISSUE STRUCTURE AND ABLATING A TISSUE REGION

(71) Applicant: University of Iowa Research Foundation, Iowa City, IA (US)

(72) Inventor: Steven Richard Mickelsen, Iowa City, IA (US)

(73) Assignee: University of Iowa Research Foundation, Iowa City, IA (US)

( * ) Notice: Subject to any disclaimer, the term of this patent is extended or adjusted under 35 U.S.C. 154(b) by 0 days.

(21) Appl. No.: 16/875,076

(22) Filed: May 15, 2020

(65) Prior Publication Data

US 2021/0031020 A1 Feb. 4, 2021

Related U.S. Application Data

(63) Continuation of application No. 15/917,194, filed on Mar. 9, 2018, now abandoned, which is a (Continued)

(51) Int. Cl.
*A61B 18/14* (2006.01)
*A61M 39/10* (2006.01)
(Continued)

(52) U.S. Cl.
CPC ........... *A61M 39/10* (2013.01); *A61B 5/0538* (2013.01); *A61B 5/4833* (2013.01);
(Continued)

(58) Field of Classification Search
CPC ...... A61B 18/1492; A61B 2018/00613; A61B 2018/00363; A61B 2018/00375
See application file for complete search history.

(56) References Cited

U.S. PATENT DOCUMENTS

| 4,200,104 A | 4/1980 | Harris |
| 4,470,407 A | 9/1984 | Hussein |

(Continued)

FOREIGN PATENT DOCUMENTS

| EP | 1042990 A1 | 10/2000 |
| EP | 1125549 | 8/2001 |

(Continued)

OTHER PUBLICATIONS

Office Action for Canadian Application No. 2,881,462, dated Mar. 19, 2019, 5 pages.

(Continued)

*Primary Examiner* — Joanne M Hoffman
*Assistant Examiner* — Sean W Collins
(74) *Attorney, Agent, or Firm* — Smith Gambrell & Russell LLP

(57) ABSTRACT

A percutaneous catheter system for use within the human body and an ablation catheter for ablating a selected tissue region within the body of a subject. The percutaneous catheter system can include two catheters that are operatively coupled to one another by magnetic coupling through a tissue structure. The ablation catheter can include electrodes positioned within a central portion. The ablation catheter is positioned such that the central portion of a flexible shaft at least partially surrounds the selected tissue region. Each electrode of the ablation catheter can be activated independently to apply ablative energy to the selected tissue region. The ablation catheter can employ high impedance structures to change the current density at specific points. Methods of puncturing through a tissue structure using the percutaneous catheter system are disclosed. Also disclosed are methods for ablating a selected tissue region using the ablation catheter.

20 Claims, 43 Drawing Sheets

Related U.S. Application Data continuation of application No. 15/819,726, filed on Nov. 21, 2017, now abandoned, which is a continuation of application No. 14/400,455, filed as application No. PCT/US2013/031252 on Mar. 14, 2013, now Pat. No. 9,861,802.

(60) Provisional application No. 61/681,552, filed on Aug. 9, 2012.

(51) Int. Cl.

| | |
|---|---|
| *A61B 5/0538* | (2021.01) |
| *A61B 5/00* | (2006.01) |
| *A61B 18/12* | (2006.01) |
| *A61M 25/01* | (2006.01) |
| *A61M 25/06* | (2006.01) |
| *A61B 34/00* | (2016.01) |
| *A61M 25/09* | (2006.01) |
| *A61M 25/00* | (2006.01) |
| *A61B 17/22* | (2006.01) |
| *A61B 18/02* | (2006.01) |
| *A61B 18/18* | (2006.01) |
| *A61B 18/20* | (2006.01) |
| *A61B 18/00* | (2006.01) |
| *A61B 17/00* | (2006.01) |

(52) U.S. Cl.
CPC ...... *A61B 18/1206* (2013.01); *A61B 18/1492* (2013.01); *A61B 34/73* (2016.02); *A61M 25/0127* (2013.01); *A61M 25/0169* (2013.01); *A61M 25/0606* (2013.01); *A61M 25/09* (2013.01); *A61B 17/22004* (2013.01); *A61B 18/02* (2013.01); *A61B 18/1815* (2013.01); *A61B 18/20* (2013.01); *A61B 2017/00876* (2013.01); *A61B 2018/0075* (2013.01); *A61B 2018/00363* (2013.01); *A61B 2018/00375* (2013.01); *A61B 2018/00577* (2013.01); *A61B 2018/00613* (2013.01); *A61B 2018/00839* (2013.01); *A61B 2018/126* (2013.01); *A61B 2018/128* (2013.01); *A61B 2018/1467* (2013.01); *A61B 2034/731* (2016.02); *A61B 2217/005* (2013.01); *A61B 2218/002* (2013.01); *A61M 2025/0089* (2013.01)

(56) References Cited

U.S. PATENT DOCUMENTS

| | | |
|---|---|---|
| 4,739,759 A | 4/1988 | Rexroth et al. |
| 5,234,004 A | 8/1993 | Hascoet et al. |
| 5,242,441 A | 9/1993 | Avitall |
| 5,257,635 A | 11/1993 | Langberg |
| 5,281,213 A | 1/1994 | Milder et al. |
| 5,304,214 A | 4/1994 | DeFord et al. |
| 5,306,296 A | 4/1994 | Wright et al. |
| 5,334,193 A | 8/1994 | Nardella |
| 5,341,807 A | 8/1994 | Nardella |
| 5,342,301 A | 8/1994 | Saab |
| 5,398,683 A | 3/1995 | Edwards et al. |
| 5,443,463 A | 8/1995 | Stern et al. |
| 5,454,370 A | 10/1995 | Avitall |
| 5,515,848 A | 5/1996 | Corbett, III et al. |
| 5,531,685 A | 7/1996 | Hemmer et al. |
| 5,545,161 A | 8/1996 | Imran |
| 5,558,091 A | 9/1996 | Acker et al. |
| 5,578,040 A | 11/1996 | Smith |
| 5,617,854 A | 4/1997 | Munsif |
| 5,624,430 A | 4/1997 | Eton et al. |
| 5,662,108 A | 9/1997 | Budd et al. |
| 5,667,491 A | 9/1997 | Pliquett et al. |
| 5,672,170 A | 9/1997 | Cho |
| 5,700,243 A | 12/1997 | Narciso, Jr. |
| 5,702,438 A | 12/1997 | Avitall |
| 5,706,823 A | 1/1998 | Wodlinger |
| 5,722,400 A | 3/1998 | Ockuly et al. |
| 5,722,402 A | 3/1998 | Swanson et al. |
| 5,749,914 A | 5/1998 | Janssen |
| 5,779,699 A | 7/1998 | Lipson |
| 5,788,692 A | 8/1998 | Campbell et al. |
| 5,810,762 A | 9/1998 | Hofmann |
| 5,833,710 A | 11/1998 | Jacobson |
| 5,836,874 A | 11/1998 | Swanson et al. |
| 5,836,942 A | 11/1998 | Netherly et al. |
| 5,836,947 A | 11/1998 | Fleischman et al. |
| 5,843,154 A | 12/1998 | Osypka |
| 5,849,028 A | 12/1998 | Chen |
| 5,863,291 A | 1/1999 | Schaer |
| 5,868,736 A | 2/1999 | Swanson et al. |
| 5,871,523 A | 2/1999 | Fleischman et al. |
| 5,876,336 A | 3/1999 | Swanson et al. |
| 5,885,278 A | 3/1999 | Fleischman et al. |
| 5,895,404 A | 4/1999 | Ruiz |
| 5,899,917 A | 5/1999 | Edwards et al. |
| 5,904,709 A | 5/1999 | Arndt et al. |
| 5,913,854 A | 6/1999 | Maguire et al. |
| 5,916,158 A | 6/1999 | Webster, Jr. |
| 5,916,213 A | 6/1999 | Haissaguerre et al. |
| 5,921,924 A | 7/1999 | Avitall |
| 5,928,269 A | 7/1999 | Alt |
| 5,928,270 A | 7/1999 | Ramsey, III |
| 6,002,955 A | 12/1999 | Willems et al. |
| 6,006,131 A | 12/1999 | Cooper et al. |
| 6,009,351 A | 12/1999 | Flachman |
| 6,014,579 A | 1/2000 | Pomeranz et al. |
| 6,029,671 A | 2/2000 | Stevens et al. |
| 6,033,403 A | 3/2000 | Tu et al. |
| 6,035,238 A | 3/2000 | Ingle et al. |
| 6,045,550 A | 4/2000 | Simpson et al. |
| 6,068,653 A | 5/2000 | LaFontaine |
| 6,071,274 A | 6/2000 | Thompson et al. |
| 6,071,281 A | 6/2000 | Burnside et al. |
| 6,074,389 A | 6/2000 | Levine et al. |
| 6,076,012 A | 6/2000 | Swanson et al. |
| 6,090,104 A | 7/2000 | Webster, Jr. |
| 6,096,036 A | 8/2000 | Bowe et al. |
| 6,113,595 A | 9/2000 | Muntermann |
| 6,119,041 A | 9/2000 | Pomeranz et al. |
| 6,120,500 A | 9/2000 | Bednarek et al. |
| 6,146,381 A | 11/2000 | Bowe et al. |
| 6,164,283 A | 12/2000 | Lesh |
| 6,167,291 A | 12/2000 | Barajas et al. |
| 6,171,305 B1 | 1/2001 | Sherman |
| 6,216,034 B1 | 4/2001 | Hofmann et al. |
| 6,219,582 B1 | 4/2001 | Hofstad et al. |
| 6,223,085 B1 | 4/2001 | Dann et al. |
| 6,231,518 B1 | 5/2001 | Grabek et al. |
| 6,245,064 B1 | 6/2001 | Lesh et al. |
| 6,251,107 B1 | 6/2001 | Schaer |
| 6,251,128 B1 | 6/2001 | Knopp et al. |
| 6,270,476 B1 | 8/2001 | Santoianni et al. |
| 6,272,384 B1 | 8/2001 | Simon et al. |
| 6,287,306 B1 | 9/2001 | Kroll et al. |
| 6,314,963 B1 | 11/2001 | Vaska et al. |
| 6,322,559 B1 | 11/2001 | Daulton et al. |
| 6,350,263 B1 | 2/2002 | Wetzig et al. |
| 6,370,412 B1 | 4/2002 | Armoundas et al. |
| 6,391,024 B1 | 5/2002 | Sun et al. |
| 6,447,505 B2 | 9/2002 | McGovern et al. |
| 6,464,699 B1 | 10/2002 | Swanson |
| 6,470,211 B1 | 10/2002 | Ideker et al. |
| 6,502,576 B1 | 1/2003 | Lesh |
| 6,503,247 B2 | 1/2003 | Swartz et al. |
| 6,517,534 B1 | 2/2003 | McGovern et al. |
| 6,527,724 B1 | 3/2003 | Fenici |
| 6,527,767 B2 | 3/2003 | Wang et al. |
| 6,592,581 B2 | 7/2003 | Bowe |
| 6,595,991 B2 | 7/2003 | Tollner et al. |
| 6,607,520 B2 | 8/2003 | Keane |
| 6,623,480 B1 | 9/2003 | Kuo et al. |
| 6,638,278 B2 | 10/2003 | Falwell et al. |

(56) References Cited

U.S. PATENT DOCUMENTS

| | | |
|---|---|---|
| 6,666,863 B2 | 12/2003 | Wentzel et al. |
| 6,669,693 B2 | 12/2003 | Friedman |
| 6,702,811 B2 | 3/2004 | Stewart et al. |
| 6,719,756 B1 | 4/2004 | Muntermann |
| 6,723,092 B2 | 4/2004 | Brown et al. |
| 6,728,563 B2 | 4/2004 | Rashidi |
| 6,743,225 B2 | 6/2004 | Sanchez et al. |
| 6,743,226 B2 | 6/2004 | Cosman et al. |
| 6,743,239 B1 | 6/2004 | Kuehn et al. |
| 6,764,486 B2 | 7/2004 | Natale |
| 6,780,181 B2 | 8/2004 | Kroll et al. |
| 6,805,128 B1 | 10/2004 | Pless |
| 6,807,447 B2 | 10/2004 | Griffin, III |
| 6,892,091 B1 | 5/2005 | Ben-Haim et al. |
| 6,893,438 B2 | 5/2005 | Hall et al. |
| 6,926,714 B1 | 8/2005 | Sra |
| 6,955,173 B2 | 10/2005 | Lesh |
| 6,960,206 B2 | 11/2005 | Keane |
| 6,960,207 B2 | 11/2005 | Vanney et al. |
| 6,972,016 B2 | 12/2005 | Hill, III et al. |
| 6,973,339 B2 | 12/2005 | Govari |
| 6,979,331 B2 | 12/2005 | Hintringer et al. |
| 6,984,232 B2 | 1/2006 | Vanney et al. |
| 6,985,776 B2 | 1/2006 | Kane et al. |
| 7,001,383 B2 | 2/2006 | Keidar |
| 7,041,095 B2 | 5/2006 | Wang et al. |
| 7,113,831 B2 | 9/2006 | Hooven |
| 7,171,263 B2 | 1/2007 | Darvish et al. |
| 7,182,725 B2 | 2/2007 | Bonan et al. |
| 7,195,628 B2 | 3/2007 | Falkenberg |
| 7,207,988 B2 | 4/2007 | Leckrone et al. |
| 7,207,989 B2 | 4/2007 | Pike, Jr. et al. |
| 7,229,402 B2 | 6/2007 | Diaz et al. |
| 7,229,437 B2 | 6/2007 | Johnson et al. |
| 7,250,049 B2 | 7/2007 | Roop et al. |
| 7,282,057 B2 | 10/2007 | Surti et al. |
| 7,285,116 B2 | 10/2007 | de la Rama et al. |
| 7,285,119 B2 | 10/2007 | Stewart et al. |
| 7,326,208 B2 | 2/2008 | Vanney et al. |
| 7,346,379 B2 | 3/2008 | Eng et al. |
| 7,367,974 B2 | 5/2008 | Haemmerich et al. |
| 7,374,567 B2 | 5/2008 | Heuser |
| 7,387,629 B2 | 6/2008 | Vanney et al. |
| 7,387,630 B2 | 6/2008 | Mest |
| 7,387,636 B2 | 6/2008 | Cohn et al. |
| 7,416,552 B2 | 8/2008 | Paul et al. |
| 7,419,477 B2 | 9/2008 | Simpson et al. |
| 7,419,489 B2 | 9/2008 | Vanney et al. |
| 7,422,591 B2 | 9/2008 | Phan |
| 7,429,261 B2 | 9/2008 | Kunis et al. |
| 7,435,248 B2 | 10/2008 | Taimisto et al. |
| 7,513,896 B2 | 4/2009 | Orszulak |
| 7,527,625 B2 | 5/2009 | Knight et al. |
| 7,578,816 B2 | 8/2009 | Boveja et al. |
| 7,588,567 B2 | 9/2009 | Boveja et al. |
| 7,623,899 B2 | 11/2009 | Worley et al. |
| 7,678,108 B2 | 3/2010 | Christian et al. |
| 7,681,579 B2 | 3/2010 | Schwartz |
| 7,771,421 B2 | 8/2010 | Stewart et al. |
| 7,805,182 B2 | 9/2010 | Weese et al. |
| 7,850,642 B2 | 12/2010 | Moll et al. |
| 7,850,685 B2 | 12/2010 | Kunis et al. |
| 7,857,808 B2 | 12/2010 | Oral et al. |
| 7,857,809 B2 | 12/2010 | Drysen |
| 7,869,865 B2 | 1/2011 | Govari et al. |
| 7,896,873 B2 | 3/2011 | Hiller et al. |
| 7,917,211 B2 | 3/2011 | Zacouto |
| 7,918,819 B2 | 4/2011 | Karmarkar et al. |
| 7,918,850 B2 | 4/2011 | Govari et al. |
| 7,922,714 B2 | 4/2011 | Stevens-Wright |
| 7,955,827 B2 | 6/2011 | Rubinsky et al. |
| 8,048,067 B2 | 11/2011 | Davalos et al. |
| 8,048,072 B2 | 11/2011 | Verin et al. |
| 8,100,895 B2 | 1/2012 | Panos et al. |
| 8,100,900 B2 | 1/2012 | Prinz et al. |
| 8,108,069 B2 | 1/2012 | Stabler et al. |
| 8,133,220 B2 | 3/2012 | Lee et al. |
| 8,137,342 B2 | 3/2012 | Crossman |
| 8,145,289 B2 | 3/2012 | Calabro' et al. |
| 8,147,486 B2 | 4/2012 | Honour et al. |
| 8,160,690 B2 | 4/2012 | Wilfley et al. |
| 8,175,680 B2 | 5/2012 | Panescu |
| 8,182,477 B2 | 5/2012 | Orszulak et al. |
| 8,206,384 B2 | 6/2012 | Falwell et al. |
| 8,206,385 B2 | 6/2012 | Stangenes et al. |
| 8,216,221 B2 | 7/2012 | Ibrahim et al. |
| 8,221,411 B2 | 7/2012 | Francischelli et al. |
| 8,226,648 B2 | 7/2012 | Paul et al. |
| 8,228,065 B2 | 7/2012 | Wirtz et al. |
| 8,235,986 B2 | 8/2012 | Kulesa et al. |
| 8,235,988 B2 | 8/2012 | Davis et al. |
| 8,251,986 B2 | 8/2012 | Chornenky et al. |
| 8,282,631 B2 | 10/2012 | Davalos et al. |
| 8,287,532 B2 | 10/2012 | Carroll et al. |
| 8,414,508 B2 | 4/2013 | Thapliyal et al. |
| 8,430,875 B2 | 4/2013 | Ibrahim et al. |
| 8,433,394 B2 | 4/2013 | Harlev et al. |
| 8,449,535 B2 | 5/2013 | Deno et al. |
| 8,454,594 B2 | 6/2013 | Demarais et al. |
| 8,463,368 B2 | 6/2013 | Harlev et al. |
| 8,475,450 B2 | 7/2013 | Govari et al. |
| 8,486,063 B2 | 7/2013 | Werneth et al. |
| 8,500,733 B2 | 8/2013 | Watson |
| 8,535,304 B2 | 9/2013 | Sklar et al. |
| 8,538,501 B2 | 9/2013 | Venkatachalam et al. |
| 8,562,588 B2 | 10/2013 | Hobbs et al. |
| 8,568,406 B2 | 10/2013 | Harlev et al. |
| 8,568,410 B2 | 10/2013 | Vakharia et al. |
| 8,571,635 B2 | 10/2013 | McGee |
| 8,571,647 B2 | 10/2013 | Harlev et al. |
| 8,579,897 B2 | 11/2013 | Vakharia et al. |
| 8,585,695 B2 | 11/2013 | Shih |
| 8,588,885 B2 | 11/2013 | Hall et al. |
| 8,597,288 B2 | 12/2013 | Christian |
| 8,608,735 B2 | 12/2013 | Govari et al. |
| 8,628,522 B2 | 1/2014 | Ibrahim et al. |
| 8,632,534 B2 | 1/2014 | Pearson et al. |
| 8,647,338 B2 | 2/2014 | Chornenky et al. |
| 8,708,952 B2 | 4/2014 | Cohen et al. |
| 8,734,442 B2 | 5/2014 | Cao et al. |
| 8,771,267 B2 | 7/2014 | Kunis et al. |
| 8,795,310 B2 | 8/2014 | Fung et al. |
| 8,808,273 B2 | 8/2014 | Caples et al. |
| 8,808,281 B2 | 8/2014 | Emons et al. |
| 8,834,461 B2 | 9/2014 | Werneth et al. |
| 8,834,464 B2 | 9/2014 | Stewart et al. |
| 8,868,169 B2 | 10/2014 | Narayan et al. |
| 8,876,817 B2 | 11/2014 | Avitall et al. |
| 8,880,195 B2 | 11/2014 | Azure |
| 8,886,309 B2 | 11/2014 | Luther et al. |
| 8,903,488 B2 | 12/2014 | Callas et al. |
| 8,920,411 B2 | 12/2014 | Gelbart et al. |
| 8,926,589 B2 | 1/2015 | Govari |
| 8,932,287 B2 | 1/2015 | Gelbart et al. |
| 8,945,117 B2 | 2/2015 | Bencini |
| 8,979,841 B2 | 3/2015 | Kunis et al. |
| 8,986,278 B2 | 3/2015 | Fung et al. |
| 9,002,442 B2 | 4/2015 | Harley et al. |
| 9,005,189 B2 | 4/2015 | Davalos et al. |
| 9,005,194 B2 | 4/2015 | Oral et al. |
| 9,011,425 B2 | 4/2015 | Fischer et al. |
| 9,044,245 B2 | 6/2015 | Condie et al. |
| 9,055,959 B2 | 6/2015 | Vaska et al. |
| 9,072,518 B2 | 7/2015 | Swanson |
| 9,078,667 B2 | 7/2015 | Besser et al. |
| 9,101,374 B1 | 8/2015 | Hoch et al. |
| 9,119,533 B2 | 9/2015 | Ghaffari |
| 9,119,634 B2 | 9/2015 | Gelbart et al. |
| 9,131,897 B2 | 9/2015 | Harada et al. |
| 9,155,590 B2 | 10/2015 | Mathur |
| 9,162,037 B2 | 10/2015 | Belson et al. |
| 9,179,972 B2 | 11/2015 | Olson |
| 9,186,481 B2 | 11/2015 | Avitall et al. |
| 9,192,769 B2 | 11/2015 | Donofrio et al. |

(56) References Cited

U.S. PATENT DOCUMENTS

| | | |
|---|---|---|
| 9,211,405 B2 | 12/2015 | Mahapatra et al. |
| 9,216,055 B2 | 12/2015 | Spence et al. |
| 9,233,248 B2 | 1/2016 | Luther et al. |
| 9,237,926 B2 | 1/2016 | Nollert et al. |
| 9,262,252 B2 | 2/2016 | Kirkpatrick et al. |
| 9,277,957 B2 | 3/2016 | Long et al. |
| 9,282,910 B2 | 3/2016 | Narayan et al. |
| 9,289,258 B2 | 3/2016 | Cohen |
| 9,289,606 B2 | 3/2016 | Paul et al. |
| 9,295,516 B2 | 3/2016 | Pearson et al. |
| 9,301,801 B2 | 4/2016 | Scheib |
| 9,375,268 B2 | 6/2016 | Long |
| 9,414,881 B2 | 8/2016 | Callas et al. |
| 9,468,495 B2 | 10/2016 | Kunis et al. |
| 9,474,486 B2 | 10/2016 | Eliason et al. |
| 9,474,574 B2 | 10/2016 | Ibrahim et al. |
| 9,480,525 B2 | 11/2016 | Lopes et al. |
| 9,486,272 B2 | 11/2016 | Bonyak et al. |
| 9,486,273 B2 | 11/2016 | Lopes et al. |
| 9,492,227 B2 | 11/2016 | Lopes et al. |
| 9,492,228 B2 | 11/2016 | Lopes et al. |
| 9,517,103 B2 | 12/2016 | Panescu et al. |
| 9,526,573 B2 | 12/2016 | Lopes et al. |
| 9,532,831 B2 | 1/2017 | Reinders et al. |
| 9,539,010 B2 | 1/2017 | Gagner et al. |
| 9,554,848 B2 | 1/2017 | Stewart et al. |
| 9,554,851 B2 | 1/2017 | Sklar et al. |
| 9,700,368 B2 | 7/2017 | Callas et al. |
| 9,724,170 B2 | 8/2017 | Mickelsen |
| 9,757,193 B2 | 9/2017 | Zarins et al. |
| 9,782,099 B2 | 10/2017 | Williams et al. |
| 9,795,442 B2 | 10/2017 | Salahieh et al. |
| 9,861,802 B2 | 1/2018 | Mickelsen |
| 9,913,685 B2 | 3/2018 | Clark et al. |
| 9,931,487 B2 | 4/2018 | Quinn et al. |
| 9,987,081 B1 | 6/2018 | Bowers et al. |
| 9,999,465 B2 | 6/2018 | Long et al. |
| 10,016,232 B1 | 7/2018 | Bowers et al. |
| 10,117,707 B2 | 11/2018 | Garcia et al. |
| 10,130,423 B1 | 11/2018 | Viswanathan et al. |
| 10,172,673 B2 | 1/2019 | Viswanathan et al. |
| 10,292,755 B2 | 5/2019 | Arena et al. |
| 10,322,286 B2 | 6/2019 | Viswanathan et al. |
| 10,433,906 B2 | 10/2019 | Mickelsen |
| 10,433,908 B2 | 10/2019 | Viswanathan et al. |
| 10,448,989 B2 | 10/2019 | Arena et al. |
| 10,507,302 B2 | 12/2019 | Leeflang et al. |
| 10,624,693 B2 | 4/2020 | Mickelsen et al. |
| 2001/0000791 A1 | 5/2001 | Suorsa et al. |
| 2001/0007070 A1 | 7/2001 | Stewart et al. |
| 2001/0044624 A1 | 11/2001 | Seraj et al. |
| 2002/0052602 A1 | 5/2002 | Wang et al. |
| 2002/0077627 A1 | 6/2002 | Johnson et al. |
| 2002/0087169 A1 | 7/2002 | Brock et al. |
| 2002/0091384 A1 | 7/2002 | Hooven et al. |
| 2002/0095176 A1 | 7/2002 | Liddicoat et al. |
| 2002/0111618 A1 | 8/2002 | Stewart et al. |
| 2002/0156526 A1 | 10/2002 | Hlavka et al. |
| 2002/0161323 A1 | 10/2002 | Miller et al. |
| 2002/0169445 A1 | 11/2002 | Jain et al. |
| 2002/0177765 A1 | 11/2002 | Bowe et al. |
| 2002/0183638 A1 | 12/2002 | Swanson |
| 2003/0014098 A1 | 1/2003 | Quijano et al. |
| 2003/0018374 A1 | 1/2003 | Paulos |
| 2003/0023287 A1 | 1/2003 | Edwards et al. |
| 2003/0028189 A1 | 2/2003 | Woloszko et al. |
| 2003/0050637 A1 | 3/2003 | Maguire et al. |
| 2003/0114849 A1 | 6/2003 | Ryan |
| 2003/0125729 A1 | 7/2003 | Hooven et al. |
| 2003/0130598 A1 | 7/2003 | Manning et al. |
| 2003/0130711 A1 | 7/2003 | Pearson et al. |
| 2003/0204161 A1 | 10/2003 | Petrie |
| 2003/0229379 A1 | 12/2003 | Ramsey |
| 2004/0039382 A1 | 2/2004 | Kroll et al. |
| 2004/0049181 A1 | 3/2004 | Stewart et al. |
| 2004/0049182 A1 | 3/2004 | Koblish et al. |
| 2004/0082859 A1 | 4/2004 | Schaer |
| 2004/0082948 A1 | 4/2004 | Stewart et al. |
| 2004/0087939 A1 | 5/2004 | Eggers et al. |
| 2004/0111087 A1 | 6/2004 | Stern et al. |
| 2004/0199157 A1 | 10/2004 | Palanker et al. |
| 2004/0215139 A1 | 10/2004 | Cohen |
| 2004/0231683 A1 | 11/2004 | Eng et al. |
| 2004/0236360 A1 | 11/2004 | Cohn et al. |
| 2004/0254607 A1 | 12/2004 | Wittenberger et al. |
| 2004/0267337 A1 | 12/2004 | Hayzelden |
| 2005/0033282 A1 | 2/2005 | Hooven |
| 2005/0187545 A1 | 8/2005 | Hooven et al. |
| 2005/0222632 A1 | 10/2005 | Obino |
| 2005/0251130 A1 | 11/2005 | Boveja et al. |
| 2005/0261672 A1 | 11/2005 | Deem et al. |
| 2006/0009755 A1 | 1/2006 | Sra |
| 2006/0009759 A1 | 1/2006 | Chrisitian et al. |
| 2006/0015095 A1 | 1/2006 | Desinger et al. |
| 2006/0015165 A1 | 1/2006 | Bertolero et al. |
| 2006/0024359 A1 | 2/2006 | Walker et al. |
| 2006/0058781 A1 | 3/2006 | Long |
| 2006/0111702 A1 | 5/2006 | Oral et al. |
| 2006/0142801 A1 | 6/2006 | Demarais et al. |
| 2006/0167448 A1 | 7/2006 | Kozel |
| 2006/0217703 A1 | 9/2006 | Chornenky et al. |
| 2006/0241734 A1 | 10/2006 | Marshall et al. |
| 2006/0264752 A1 | 11/2006 | Rubinsky et al. |
| 2006/0270900 A1 | 11/2006 | Chin et al. |
| 2006/0287648 A1 | 12/2006 | Schwartz |
| 2006/0293730 A1 | 12/2006 | Rubinsky et al. |
| 2006/0293731 A1 | 12/2006 | Rubinsky et al. |
| 2007/0005053 A1 | 1/2007 | Dando |
| 2007/0021744 A1 | 1/2007 | Creighton |
| 2007/0060989 A1 | 3/2007 | Deem et al. |
| 2007/0066972 A1 | 3/2007 | Ormsby et al. |
| 2007/0129721 A1 | 6/2007 | Phan et al. |
| 2007/0129760 A1 | 6/2007 | Demarais et al. |
| 2007/0156135 A1 | 7/2007 | Rubinsky et al. |
| 2007/0167740 A1 | 7/2007 | Grunewald et al. |
| 2007/0167940 A1 | 7/2007 | Stevens-Wright |
| 2007/0173878 A1 | 7/2007 | Heuser |
| 2007/0208329 A1 | 9/2007 | Ward et al. |
| 2007/0225589 A1 | 9/2007 | Viswanathan |
| 2007/0249923 A1 | 10/2007 | Keenan |
| 2007/0260223 A1 | 11/2007 | Scheibe et al. |
| 2007/0270792 A1 | 11/2007 | Hennemann et al. |
| 2008/0009855 A1 | 1/2008 | Hamou |
| 2008/0033426 A1 | 2/2008 | Machell |
| 2008/0065061 A1 | 3/2008 | Viswanathan |
| 2008/0086120 A1 | 4/2008 | Mirza et al. |
| 2008/0091195 A1 | 4/2008 | Silwa et al. |
| 2008/0103545 A1 | 5/2008 | Bolea et al. |
| 2008/0132885 A1 | 6/2008 | Rubinsky et al. |
| 2008/0161789 A1 | 7/2008 | Thao et al. |
| 2008/0172048 A1 | 7/2008 | Martin et al. |
| 2008/0200913 A1 | 8/2008 | Viswanathan |
| 2008/0208118 A1 | 8/2008 | Goldman |
| 2008/0208186 A1* | 8/2008 | Slater ................. A61B 18/1492 606/41 |
| 2008/0243214 A1 | 10/2008 | Koblish |
| 2008/0281322 A1 | 11/2008 | Sherman et al. |
| 2008/0300574 A1 | 12/2008 | Belson et al. |
| 2008/0300587 A1* | 12/2008 | Anderson ........... A61B 18/1492 606/29 |
| 2008/0300588 A1 | 12/2008 | Groth et al. |
| 2008/0319436 A1 | 12/2008 | Daniel et al. |
| 2009/0024084 A1 | 1/2009 | Khosla et al. |
| 2009/0048591 A1 | 2/2009 | Ibrahim et al. |
| 2009/0062788 A1 | 3/2009 | Long et al. |
| 2009/0076500 A1 | 3/2009 | Azure |
| 2009/0105654 A1 | 4/2009 | Kurth et al. |
| 2009/0138009 A1 | 5/2009 | Viswanathan et al. |
| 2009/0149917 A1 | 6/2009 | Whitehurst et al. |
| 2009/0163905 A1 | 6/2009 | Winkler et al. |
| 2009/0228003 A1 | 9/2009 | Sinelnikov |
| 2009/0240248 A1 | 9/2009 | Deford et al. |
| 2009/0275827 A1 | 11/2009 | Aiken et al. |
| 2009/0281477 A1 | 11/2009 | Mikus et al. |

(56) References Cited

U.S. PATENT DOCUMENTS

| | | |
|---|---|---|
| 2009/0306651 A1 | 12/2009 | Schneider |
| 2010/0004623 A1 | 1/2010 | Hamilton et al. |
| 2010/0004661 A1 | 1/2010 | Verin et al. |
| 2010/0023004 A1 | 1/2010 | Francischelli et al. |
| 2010/0137861 A1 | 6/2010 | Soroff et al. |
| 2010/0185140 A1 | 7/2010 | Kassab et al. |
| 2010/0185186 A1 | 7/2010 | Longoria |
| 2010/0191112 A1 | 7/2010 | Demarais et al. |
| 2010/0191232 A1 | 7/2010 | Boveda |
| 2010/0241185 A1 | 9/2010 | Mahapatra et al. |
| 2010/0261994 A1 | 10/2010 | Davalos et al. |
| 2010/0274238 A1 | 10/2010 | Klimovitch |
| 2010/0280513 A1 | 11/2010 | Juergen et al. |
| 2010/0280539 A1 | 11/2010 | Miyoshi et al. |
| 2010/0292687 A1 | 11/2010 | Kauphusman et al. |
| 2010/0312096 A1 | 12/2010 | Guttman et al. |
| 2010/0312300 A1 | 12/2010 | Ryu et al. |
| 2011/0028962 A1 | 2/2011 | Werneth et al. |
| 2011/0028964 A1 | 2/2011 | Edwards |
| 2011/0098694 A1 | 4/2011 | Long |
| 2011/0106221 A1 | 5/2011 | Neal, II et al. |
| 2011/0130708 A1 | 6/2011 | Perry et al. |
| 2011/0144524 A1 | 6/2011 | Fish et al. |
| 2011/0144633 A1 | 6/2011 | Govari |
| 2011/0160785 A1 | 6/2011 | Mori et al. |
| 2011/0190659 A1 | 8/2011 | Long et al. |
| 2011/0190727 A1 | 8/2011 | Edmunds et al. |
| 2011/0208185 A1 | 8/2011 | Diamant et al. |
| 2011/0213231 A1 | 9/2011 | Hall et al. |
| 2011/0276047 A1 | 11/2011 | Sklar et al. |
| 2011/0276075 A1 | 11/2011 | Fung et al. |
| 2011/0288544 A1 | 11/2011 | Verin et al. |
| 2011/0288547 A1 | 11/2011 | Morgan et al. |
| 2011/0313417 A1 | 12/2011 | De La Rama et al. |
| 2012/0029512 A1 | 2/2012 | Willard et al. |
| 2012/0046570 A1 | 2/2012 | Villegas et al. |
| 2012/0053581 A1 | 3/2012 | Wittkampf et al. |
| 2012/0059255 A1 | 3/2012 | Paul et al. |
| 2012/0071872 A1 | 3/2012 | Rubinsky et al. |
| 2012/0078320 A1 | 3/2012 | Schotzko et al. |
| 2012/0078343 A1 | 3/2012 | Fish |
| 2012/0089089 A1 | 4/2012 | Swain et al. |
| 2012/0095459 A1 | 4/2012 | Callas et al. |
| 2012/0101413 A1 | 4/2012 | Beetel et al. |
| 2012/0158021 A1 | 6/2012 | Morrill |
| 2012/0165667 A1 | 6/2012 | Altmann et al. |
| 2012/0172859 A1 | 7/2012 | Condie et al. |
| 2012/0172867 A1 | 7/2012 | Ryu et al. |
| 2012/0197100 A1 | 8/2012 | Razavi et al. |
| 2012/0209260 A1 | 8/2012 | Lambert et al. |
| 2012/0220998 A1 | 8/2012 | Long et al. |
| 2012/0265198 A1 | 10/2012 | Crow et al. |
| 2012/0283582 A1 | 11/2012 | Mahapatra et al. |
| 2012/0303019 A1 | 11/2012 | Zhao et al. |
| 2012/0310052 A1 | 12/2012 | Mahapatra et al. |
| 2012/0310230 A1 | 12/2012 | Willis |
| 2012/0310237 A1 | 12/2012 | Swanson |
| 2012/0316557 A1 | 12/2012 | Sartor et al. |
| 2013/0030430 A1 | 1/2013 | Stewart et al. |
| 2013/0060247 A1 | 3/2013 | Sklar et al. |
| 2013/0060248 A1 | 3/2013 | Sklar et al. |
| 2013/0079768 A1 | 3/2013 | De Luca et al. |
| 2013/0090651 A1 | 4/2013 | Smith |
| 2013/0096655 A1 | 4/2013 | Moffitt et al. |
| 2013/0103027 A1 | 4/2013 | Sklar et al. |
| 2013/0103064 A1 | 4/2013 | Arenson et al. |
| 2013/0131662 A1 | 5/2013 | Wittkampf |
| 2013/0158538 A1 | 6/2013 | Govari |
| 2013/0172715 A1 | 7/2013 | Just et al. |
| 2013/0172864 A1 | 7/2013 | Ibrahim et al. |
| 2013/0172875 A1 | 7/2013 | Govari et al. |
| 2013/0184702 A1 | 7/2013 | Neal, II et al. |
| 2013/0218157 A1 | 8/2013 | Callas et al. |
| 2013/0226174 A1 | 8/2013 | Ibrahim et al. |
| 2013/0237984 A1 | 9/2013 | Sklar |
| 2013/0253415 A1 | 9/2013 | Sano et al. |
| 2013/0296679 A1 | 11/2013 | Condie et al. |
| 2013/0310829 A1 | 11/2013 | Cohen |
| 2013/0317385 A1 | 11/2013 | Sklar et al. |
| 2013/0331831 A1 | 12/2013 | Werneth et al. |
| 2013/0338467 A1 | 12/2013 | Grasse et al. |
| 2014/0005664 A1 | 1/2014 | Govari et al. |
| 2014/0024911 A1 | 1/2014 | Harlev et al. |
| 2014/0039288 A1 | 2/2014 | Shih |
| 2014/0051993 A1 | 2/2014 | McGee |
| 2014/0052118 A1 | 2/2014 | Laske et al. |
| 2014/0052126 A1 | 2/2014 | Long et al. |
| 2014/0052216 A1 | 2/2014 | Long et al. |
| 2014/0058377 A1 | 2/2014 | Deem et al. |
| 2014/0081113 A1 | 3/2014 | Cohen et al. |
| 2014/0100563 A1 | 4/2014 | Govari et al. |
| 2014/0107644 A1 | 4/2014 | Falwell et al. |
| 2014/0142408 A1 | 5/2014 | De La Rama et al. |
| 2014/0148804 A1 | 5/2014 | Ward et al. |
| 2014/0163480 A1 | 6/2014 | Govari et al. |
| 2014/0163546 A1 | 6/2014 | Govari et al. |
| 2014/0171942 A1 | 6/2014 | Werneth et al. |
| 2014/0180035 A1 | 6/2014 | Anderson |
| 2014/0187916 A1 | 7/2014 | Clark et al. |
| 2014/0194716 A1 | 7/2014 | Diep et al. |
| 2014/0194867 A1 | 7/2014 | Fish et al. |
| 2014/0200567 A1 | 7/2014 | Cox et al. |
| 2014/0235986 A1 | 8/2014 | Harlev et al. |
| 2014/0235988 A1 | 8/2014 | Ghosh |
| 2014/0235989 A1 | 8/2014 | Wodlinger et al. |
| 2014/0243851 A1 | 8/2014 | Cohen et al. |
| 2014/0276712 A1 | 9/2014 | Mallin et al. |
| 2014/0276760 A1 | 9/2014 | Bonyak et al. |
| 2014/0276782 A1 | 9/2014 | Paskar |
| 2014/0276791 A1 | 9/2014 | Ku et al. |
| 2014/0288556 A1 | 9/2014 | Ibrahim et al. |
| 2014/0303721 A1 | 10/2014 | Fung et al. |
| 2014/0343549 A1 | 11/2014 | Spear et al. |
| 2014/0364845 A1 | 12/2014 | Rashidi |
| 2014/0371613 A1 | 12/2014 | Narayan et al. |
| 2015/0005767 A1 | 1/2015 | Werneth et al. |
| 2015/0011995 A1 | 1/2015 | Avitall et al. |
| 2015/0066108 A1 | 3/2015 | Shi et al. |
| 2015/0119674 A1 | 4/2015 | Fischell et al. |
| 2015/0126840 A1 | 5/2015 | Thakur et al. |
| 2015/0133914 A1 | 5/2015 | Koblish |
| 2015/0138977 A1 | 5/2015 | Dacosta |
| 2015/0141978 A1 | 5/2015 | Subramaniam et al. |
| 2015/0142041 A1 | 5/2015 | Kendale et al. |
| 2015/0148796 A1 | 5/2015 | Bencini |
| 2015/0150472 A1 | 6/2015 | Harlev et al. |
| 2015/0157402 A1 | 6/2015 | Kunis et al. |
| 2015/0157412 A1 | 6/2015 | Wallace et al. |
| 2015/0164584 A1 | 6/2015 | Davalos et al. |
| 2015/0173824 A1 | 6/2015 | Davalos et al. |
| 2015/0173828 A1 | 6/2015 | Avitall |
| 2015/0174404 A1 | 6/2015 | Rousso et al. |
| 2015/0182740 A1 | 7/2015 | Mickelsen |
| 2015/0196217 A1 | 7/2015 | Harlev et al. |
| 2015/0223726 A1 | 8/2015 | Harlev et al. |
| 2015/0230699 A1 | 8/2015 | Berul et al. |
| 2015/0258344 A1 | 9/2015 | Tandri et al. |
| 2015/0265342 A1 | 9/2015 | Long et al. |
| 2015/0265344 A1 | 9/2015 | Aktas et al. |
| 2015/0272656 A1 | 10/2015 | Chen |
| 2015/0272664 A9 | 10/2015 | Cohen |
| 2015/0272667 A1 | 10/2015 | Govari et al. |
| 2015/0282729 A1 | 10/2015 | Harlev et al. |
| 2015/0289923 A1 | 10/2015 | Davalos et al. |
| 2015/0304879 A1 | 10/2015 | Dacosta |
| 2015/0320481 A1 | 11/2015 | Cosman et al. |
| 2015/0321021 A1 | 11/2015 | Tandri et al. |
| 2015/0327944 A1 | 11/2015 | Neal, II et al. |
| 2015/0342532 A1 | 12/2015 | Basu et al. |
| 2015/0343212 A1 | 12/2015 | Rousso et al. |
| 2015/0351836 A1 | 12/2015 | Prutchi |
| 2015/0359583 A1 | 12/2015 | Swanson |
| 2016/0000500 A1 | 1/2016 | Salahieh et al. |
| 2016/0008061 A1 | 1/2016 | Fung et al. |

(56) References Cited

U.S. PATENT DOCUMENTS

| | | |
|---|---|---|
| 2016/0008065 A1 | 1/2016 | Gliner et al. |
| 2016/0029960 A1 | 2/2016 | Toth et al. |
| 2016/0038772 A1 | 2/2016 | Thapliyal et al. |
| 2016/0051204 A1 | 2/2016 | Harlev et al. |
| 2016/0051324 A1 | 2/2016 | Stewart et al. |
| 2016/0058493 A1 | 3/2016 | Neal, II et al. |
| 2016/0058506 A1 | 3/2016 | Spence et al. |
| 2016/0066993 A1 | 3/2016 | Avitall et al. |
| 2016/0074679 A1 | 3/2016 | Thapliyal et al. |
| 2016/0095531 A1 | 4/2016 | Narayan et al. |
| 2016/0095642 A1 | 4/2016 | Deno et al. |
| 2016/0095653 A1 | 4/2016 | Lambert et al. |
| 2016/0100797 A1 | 4/2016 | Mahapatra et al. |
| 2016/0100884 A1 | 4/2016 | Fay et al. |
| 2016/0106498 A1 | 4/2016 | Highsmith et al. |
| 2016/0106500 A1 | 4/2016 | Olson |
| 2016/0113709 A1 | 4/2016 | Maor |
| 2016/0113712 A1 | 4/2016 | Cheung et al. |
| 2016/0120564 A1 | 5/2016 | Kirkpatrick et al. |
| 2016/0128770 A1 | 5/2016 | Afonso et al. |
| 2016/0166167 A1 | 6/2016 | Narayan et al. |
| 2016/0166310 A1 | 6/2016 | Stewart et al. |
| 2016/0166311 A1 | 6/2016 | Long et al. |
| 2016/0174865 A1 | 6/2016 | Stewart et al. |
| 2016/0183877 A1 | 6/2016 | Williams et al. |
| 2016/0184003 A1 | 6/2016 | Srimathveeravalli et al. |
| 2016/0184004 A1 | 6/2016 | Hull et al. |
| 2016/0213282 A1 | 7/2016 | Leo et al. |
| 2016/0220307 A1 | 8/2016 | Miller et al. |
| 2016/0235470 A1 | 8/2016 | Callas et al. |
| 2016/0287314 A1 | 10/2016 | Arena et al. |
| 2016/0310211 A1 | 10/2016 | Long |
| 2016/0324564 A1 | 11/2016 | Gerlach et al. |
| 2016/0324573 A1 | 11/2016 | Mickelsen et al. |
| 2016/0331441 A1 | 11/2016 | Konings |
| 2016/0331459 A1 | 11/2016 | Townley et al. |
| 2016/0354142 A1 | 12/2016 | Pearson et al. |
| 2016/0361109 A1 | 12/2016 | Weaver et al. |
| 2017/0001016 A1 | 1/2017 | De Ridder |
| 2017/0035499 A1 | 2/2017 | Stewart et al. |
| 2017/0042449 A1 | 2/2017 | Deno et al. |
| 2017/0042615 A1 | 2/2017 | Salahieh et al. |
| 2017/0056648 A1 | 3/2017 | Syed et al. |
| 2017/0065330 A1 | 3/2017 | Mickelsen et al. |
| 2017/0065339 A1 | 3/2017 | Mickelsen |
| 2017/0065340 A1 | 3/2017 | Long |
| 2017/0065343 A1 | 3/2017 | Mickelsen |
| 2017/0071543 A1 | 3/2017 | Basu et al. |
| 2017/0095291 A1 | 4/2017 | Harrington et al. |
| 2017/0105793 A1 | 4/2017 | Cao et al. |
| 2017/0120048 A1 | 5/2017 | He et al. |
| 2017/0146584 A1 | 5/2017 | Daw et al. |
| 2017/0151029 A1 | 6/2017 | Mickelsen |
| 2017/0172654 A1 | 6/2017 | Wittkampf et al. |
| 2017/0181795 A1 | 6/2017 | Debruyne |
| 2017/0189097 A1 | 7/2017 | Viswanathan et al. |
| 2017/0215953 A1 | 8/2017 | Long et al. |
| 2017/0245928 A1 | 8/2017 | Xiao et al. |
| 2017/0246455 A1 | 8/2017 | Athos et al. |
| 2017/0312024 A1 | 11/2017 | Harlev et al. |
| 2017/0312025 A1 | 11/2017 | Harlev et al. |
| 2017/0312027 A1 | 11/2017 | Harlev et al. |
| 2018/0001056 A1 | 1/2018 | Leeflang et al. |
| 2018/0042674 A1 | 2/2018 | Mickelsen |
| 2018/0042675 A1 | 2/2018 | Long |
| 2018/0043153 A1 | 2/2018 | Viswanathan et al. |
| 2018/0064488 A1 | 3/2018 | Long et al. |
| 2018/0085160 A1 | 3/2018 | Viswanathan et al. |
| 2018/0093088 A1 | 4/2018 | Mickelsen |
| 2018/0133460 A1 | 5/2018 | Townley et al. |
| 2018/0168511 A1 | 6/2018 | Hall et al. |
| 2018/0184982 A1 | 7/2018 | Basu et al. |
| 2018/0193090 A1 | 7/2018 | de la Rama et al. |
| 2018/0200497 A1 | 7/2018 | Mickelsen |
| 2018/0289417 A1 | 10/2018 | Schweitzer et al. |
| 2018/0303488 A1 | 10/2018 | Hill |
| 2018/0311497 A1 | 11/2018 | Viswanathan et al. |
| 2018/0344393 A1 | 12/2018 | Gruba et al. |
| 2018/0360534 A1 | 12/2018 | Teplitsky et al. |
| 2019/0038171 A1 | 2/2019 | Howard |
| 2019/0046791 A1 | 2/2019 | Ebbers et al. |
| 2019/0069950 A1 | 3/2019 | Viswanathan et al. |
| 2019/0125439 A1 | 5/2019 | Rohl et al. |
| 2019/0151015 A1 | 5/2019 | Viswanathan et al. |
| 2019/0183378 A1 | 6/2019 | Mosesov et al. |
| 2019/0209238 A1 | 7/2019 | Jimenez |
| 2019/0223938 A1 | 7/2019 | Arena et al. |
| 2019/0223950 A1 | 7/2019 | Gelbart et al. |
| 2019/0231421 A1 | 8/2019 | Viswanathan et al. |
| 2019/0233809 A1 | 8/2019 | Neal, II et al. |
| 2019/0256839 A1 | 8/2019 | Neal, II et al. |
| 2019/0269912 A1 | 9/2019 | Viswanathan et al. |
| 2019/0328445 A1 | 10/2019 | Sano et al. |
| 2019/0336198 A1 | 11/2019 | Viswanathan et al. |
| 2019/0376055 A1 | 12/2019 | Davalos et al. |
| 2020/0114121 A1 | 4/2020 | Leeflang et al. |

FOREIGN PATENT DOCUMENTS

| | | |
|---|---|---|
| EP | 0797956 | 6/2003 |
| EP | 1127552 | 6/2006 |
| EP | 1340469 | 3/2007 |
| EP | 1009303 | 6/2009 |
| EP | 2213729 | 8/2010 |
| EP | 2425871 | 3/2012 |
| EP | 1803411 | 8/2012 |
| EP | 2532320 A2 | 12/2012 |
| EP | 2587275 | 5/2013 |
| EP | 2663227 | 11/2013 |
| EP | 1909678 | 1/2014 |
| EP | 2217165 | 3/2014 |
| EP | 2376193 | 3/2014 |
| EP | 2708181 | 3/2014 |
| EP | 2777579 A1 | 9/2014 |
| EP | 2934307 | 10/2015 |
| EP | 2777585 | 6/2016 |
| EP | 2382935 B1 | 3/2018 |
| EP | 3111871 B1 | 3/2018 |
| EP | 3151773 B1 | 4/2018 |
| EP | 3056242 B1 | 7/2018 |
| JP | H06-507797 | 9/1994 |
| JP | H10-510745 | 10/1998 |
| JP | 2000-508196 | 7/2000 |
| JP | 2005-516666 | 6/2005 |
| JP | 2006-506184 | 2/2006 |
| JP | 2007-325935 | 12/2007 |
| JP | 2008-538997 | 11/2008 |
| JP | 2009-500129 | 1/2009 |
| JP | 2011-509158 | 3/2011 |
| JP | 2012-050538 | 3/2012 |
| WO | WO 92/07622 | 5/1992 |
| WO | WO 92/21278 | 12/1992 |
| WO | WO 92/21285 | 12/1992 |
| WO | WO 94/07413 | 4/1994 |
| WO | WO 97/24073 | 7/1997 |
| WO | WO 97/25917 | 7/1997 |
| WO | WO 97/37719 | 10/1997 |
| WO | WO 1999/004851 | 2/1999 |
| WO | WO 1999/022659 | 5/1999 |
| WO | WO 1999/056650 | 11/1999 |
| WO | WO 1999/059486 | 11/1999 |
| WO | WO 2002/056782 | 7/2002 |
| WO | WO 2003/053289 | 7/2003 |
| WO | WO 2003/065916 | 8/2003 |
| WO | WO 2004/045442 | 6/2004 |
| WO | WO 2004/086994 | 10/2004 |
| WO | WO 2005/046487 | 5/2005 |
| WO | WO 2006/115902 | 11/2006 |
| WO | WO 2007/006055 | 1/2007 |
| WO | WO 2007/079438 | 7/2007 |
| WO | WO 2009/082710 | 7/2009 |
| WO | WO 2009/089343 | 7/2009 |
| WO | WO 2009/137800 | 11/2009 |
| WO | WO 2010/014480 | 2/2010 |

(56) References Cited

FOREIGN PATENT DOCUMENTS

| WO | WO 2011/028310 | 3/2011 |
|---|---|---|
| WO | WO 2011/154805 | 12/2011 |
| WO | WO 2012/051433 | 4/2012 |
| WO | WO 2012/153928 | 11/2012 |
| WO | WO 2013/019385 | 2/2013 |
| WO | WO 2014/025394 | 2/2014 |
| WO | WO 2014/031800 | 2/2014 |
| WO | WO 2014/036439 | 3/2014 |
| WO | WO 2014/160832 | 10/2014 |
| WO | WO 2015/066322 | 5/2015 |
| WO | WO 2015/099786 | 7/2015 |
| WO | WO 2015/103530 | 7/2015 |
| WO | WO 2015/103574 | 7/2015 |
| WO | WO 2015/130824 | 9/2015 |
| WO | WO 2015/140741 | 9/2015 |
| WO | WO 2015/143327 | 9/2015 |
| WO | WO 2015/171921 | 11/2015 |
| WO | WO 2015/175944 | 11/2015 |
| WO | WO 2015/192018 | 12/2015 |
| WO | WO 2015/192027 | 12/2015 |
| WO | WO 2016/059027 | 4/2016 |
| WO | WO 2016/060983 | 4/2016 |
| WO | WO 2016/081650 | 5/2016 |
| WO | WO 2016/090175 | 6/2016 |
| WO | WO 2017/093926 | 6/2017 |
| WO | WO 2017/119934 | 7/2017 |
| WO | WO 2017/120169 | 7/2017 |
| WO | WO 2017/192477 | 11/2017 |
| WO | WO 2017/192495 | 11/2017 |
| WO | WO 2017/218734 | 12/2017 |
| WO | WO 2018/005511 | 1/2018 |
| WO | WO 2018/191149 | 10/2018 |
| WO | WO 2018/200800 | 11/2018 |
| WO | WO 2019/118436 | 6/2019 |
| WO | WO 2019/133606 | 7/2019 |
| WO | WO 2019/234133 | 12/2019 |

OTHER PUBLICATIONS

Partial Supplementary European Search Report for European Application No. 13827672.0, dated Mar. 23, 2016, 6 pages.
Supplementary European Search Report for European Application No. 13827672.0, dated Jul. 11, 2016, 12 pages.
Office Action for European Application No. 13827672.0, dated Feb. 5, 2018, 6 pages.
Notice of Reasons for Rejection for Japanese Application No. 2015-526522, dated Mar. 6, 2017, 3 pages.
Office Action for U.S. Appl. No. 14/400,455, dated Mar. 30, 2017, 10 pages.
International Search Report and Written Opinion for International Application No. PCT/US2013/031252, dated Jul. 19, 2013, 12 pages.
Extended European Search Report for European Application No. 19182099.2, dated Dec. 13, 2019, 7 pages.
Office Action for Japanese Application No. 2018-036714, dated Jan. 16, 2019, 8 pages.
Office Action for Japanese Application No. 2018-036714, dated Nov. 27, 2019, 5 pages.
Office Action for U.S. Appl. No. 15/819,726, dated Jun. 4, 2018, 17 pages.
Office Action for U.S. Appl. No. 15/917,194, dated Jun. 4, 2018, 17 pages.
Office Action for U.S. Appl. No. 15/917,194, dated Oct. 9, 2018, 13 pages.
Office Action for U.S. Appl. No. 15/917,194, dated Apr. 29, 2019, 10 pages.
Office Action for U.S. Appl. No. 15/917,194, dated Dec. 20, 2019, 10 pages.
First Office Action for Chinese Application No. 201580006848.8, dated Jan. 29, 2018, 15 pages.
Office Action for European Application No. 15701856.5, dated Dec. 11, 2017, 6 pages.
Notice of Reasons for Rejection for Japanese Application No. 2016-544072, dated Oct. 1, 2018, 11 pages.
Office Action for U.S. Appl. No. 15/201,983, dated Apr. 3, 2019, 16 pages.
Office Action for U.S. Appl. No. 15/201,983, dated Nov. 15, 2019, 15 pages.
International Search Report and Written Opinion for International Application No. PCT/US2015/010138, dated Mar. 26, 2015, 14 pages.
International Preliminary Reporton Patentability for International Application No. PCT/US2015/010138, dated Jul. 12, 2016, 9 pages.
Supplementary European Search Report for European Application No. 15733297.4, dated Aug. 10, 2017, 7 pages.
Office Action for U.S. Appl. No. 15/201,997, dated Apr. 3, 2017, 6 pages.
Office Action for U.S. Appl. No. 15/201,997, dated Aug. 29, 2017, 12 pages.
Office Action for U.S. Appl. No. 15/201,997, dated Jul. 12, 2018, 12 pages.
Office Action for U.S. Appl. No. 15/201,997, dated Dec. 17, 2018, 17 pages.
International Search Report and Written Opinion for International Application No. PCT/US2015/010223, dated Apr. 10, 2015, 19 pages.
International Preliminary Report on Patentability for International Application No. PCT/US2015/010223, dated Jul. 12, 2016, 12 pages.
Office Action for U.S. Appl. No. 15/341,512, dated Aug. 1, 2019, 19 pages.
Office Action for U.S. Appl. No. 15/341,512, dated Nov. 12, 2019, 18 pages.
International Search Report and Written Opinion for International Application No. PCT/US2015/029734, dated Nov. 24, 2015, 15 pages.
Extended European Search Report for European Application No. 18189811.5, dated May 14, 2019, 7 pages.
Office Action for U.S. Appl. No. 15/795,062, dated Dec. 19, 2017, 14 pages.
Office Action for U.S. Appl. No. 15/795,062, dated Apr. 9, 2018, 20 pages.
Office Action for U.S. Appl. No. 15/795,062, dated May 3, 2019, 21 pages.
Office Action for U.S. Appl. No. 15/795,062, dated Nov. 4, 2019, 23 pages.
Office Action for U.S. Appl. No. 15/795,062, dated Apr. 20, 2020, 19 pages.
Office Action for European Application No. 15726465.6, dated Dec. 10, 2019, 6 pages.
Office Action for U.S. Appl. No. 15/341,523, dated Jan. 29, 2019, 10 pages.
Office Action for U.S. Appl. No. 15/341,523, dated Jul. 30, 2019, 8 pages.
International Search Report and Written Opinion for International Application No. PCT/US2015/031086, dated Oct. 21, 2015, 16 pages.
Office Action for U.S. Appl. No. 15/795,075, dated Feb. 6, 2018, 9 pages.
Office Action for U.S. Appl. No. 15/795,075, dated Jun. 15, 2018, 10 pages.
Office Action for U.S. Appl. No. 15/795,075, dated Apr. 10, 2019, 11 pages.
Office Action for U.S. Appl. No. 15/795,075, dated Jul. 31, 2019, 12 pages.
Extended European Search Report for European Application No. 15849844.4, dated May 3, 2018, 8 pages.
Office Action for U.S. Appl. No. 15/484,969, dated Sep. 4, 2019, 12 pages.
International Search Report and Written Opinion for International Application No. PCT/US2015/055105, dated Mar. 1, 2016, 15 pages.

(56) References Cited

OTHER PUBLICATIONS

Office Action for U.S. Appl. No. 15/796,255, dated Jan. 10, 2018, 12 pages.
Extended European Search Report for European Application No. 15806855.1, dated Jan. 3, 2018, 8 pages.
Office Action for U.S. Appl. No. 15/354,475, dated May 23, 2019, 7 pages.
International Search Report and Written Opinion for International Application No. PCT/US2015/035582, dated Oct. 2, 2015, 17 pages.
Extended European Search Report for European Application No. 15806278.6, dated Feb. 9, 2018, 5 pages.
International Search Report and Written Opinion for International Application No. PCT/US2015/035592, dated Oct. 2, 2015, 13 pages.
Extended European Search Report for European Application No. 16884132.8, dated Jul. 8, 2019, 7 pages.
Office Action for U.S. Appl. No. 15/334,646, dated Jul. 25, 2017, 19 pages.
Office Action for U.S. Appl. No. 15/334,646, dated Nov. 16, 2017, 26 pages.
International Search Report and Written Opinion for International Application No. PCT/US2016/057664, dated Feb. 24, 2017, 11 pages.
Office Action for U.S. Appl. No. 15/796,375, dated Jan. 24, 2018, 25 pages.
Office Action for U.S. Appl. No. 15/796,375, dated May 30, 2018, 26 pages.
Office Action for U.S. Appl. No. 15/796,375, dated Nov. 16, 2018, 27 pages.
Office Action for U.S. Appl. No. 16/416,677, dated Aug. 15, 2019, 8 pages.
Extended European Search Report for European Application No. 17736218.3 dated Aug. 23, 2019, 9 pages.
International Search Report and Written Opinion for International Application No. PCT/US2017/012099, dated May 18, 2017, 17 pages.
Office Action for U.S. Appl. No. 15/711,266, dated Feb. 23, 2018, 14 pages.
International Search Report and Written Opinion for International Application No. PCT/US2018/029938, dated Aug. 29, 2018, 14 pages.
Office Action for U.S. Appl. No. 16/181,027, dated Sep. 4, 2019, 12 pages.
International Search Report and Written Opinion for International Application No. PCT/US2019/014226, dated Apr. 29, 2019, 15 pages.
Office Action for U.S. Appl. No. 16/240,066, dated May 29, 2019, 7 pages.
Office Action for U.S. Appl. No. 16/375,561, dated Oct. 17, 2019, 15 pages.
Extended European Search Report for European Application No. 17814062.0, dated Feb. 4, 2020, 9 pages.
International Search Report and Written Opinion for International Application No. PCT/US2017/037609, dated Nov. 8, 2017, 13 pages.
Office Action for U.S. Appl. No. 15/672,916, dated Feb. 13, 2018, 16 pages.
Office Action for U.S. Appl. No. 15/672,916, dated Jul. 20, 2018, 23 pages.
Office Action for U.S. Appl. No. 15/672,916, dated Apr. 9, 2019, 31 pages.
Office Action for U.S. Appl. No. 15/499,804, dated Jan. 3, 2018, 20 pages.
Office Action for U.S. Appl. No. 15/794,717, dated Feb. 1, 2018, 10 pages.
International Search Report and Written Opinion for International Application No. PCT/US2018/029552, dated Jun. 29, 2018, 13 pages.
Partial European Search Report for European Application No. 18170210.1, dated Feb. 14, 2019, 13 pages.
Extended European Search Report for European Application No. 18170210.1, dated May 17, 2019, 11 pages.
International Search Report and Written Opinion for International Application No. PCT/US2018/050660, dated Nov. 26, 2018, 13 pages.
Office Action for U.S. Appl. No. 15/970,404, dated Oct. 9, 2018, 21 pages.
Office Action for U.S. Appl. No. 15/970,404, dated Apr. 12, 2019, 20 pages.
Office Action for U.S. Appl. No. 15/970,404, dated Nov. 12, 2019, 19 pages.
International Search Report and Written Opinion for International Application No. PCT/US2019/028943, dated Sep. 17, 2019, 17 pages.
International Search Report and Written Opinion for International Application No. PCT/US2019/017322, dated May 10, 2019, 15 pages.
International Search Report and Written Opinion for International Application No. PCT/US2019/030922, dated Sep. 6, 2019, 12 pages.
International Search Report and Written Opinion for International Application No. PCT/US2019/030882, dated Sep. 10, 2019, 17 pages.
Office Action for U.S. Appl. No. 16/405,515, dated Sep. 6, 2019, 9 pages.
International Search Report and Written Opinion for International Application No. PCT/US2019/031135, dated Aug. 5, 2019, 11 pages.
Du Pre, B.C. et al., "Minimal coronary artery damage by myocardial electroporation ablation," Europace, 15(1):144-149 (2013).
Hobbs, E. P., "Investor Relations Update: Tissue Ablation via Irreversible Electroporation (IRE)," Powerpoint (2004), 16 pages.
Lavee, J. et al., "A Novel Nonthermal Energy Source for Surgical Epicardial Atrial Ablation: Irreversible Electroporation," The Heart Surgery Forum #2006-1202, 10(2), 2007 [Epub Mar. 2007].
Madhavan, M. et al., "Novel Percutaneous Epicardial Autonomic Modulation in the Canine for Atrial Fibrillation: Results of an Efficacy and Safety Study," Pace, 00:1-11 (2016).
Neven, K. et al., "Safety and Feasibility of Closed Chest Epicardial Catheter Ablation Using Electroporation," Circ Arrhythm Electrophysiol., 7:913-919 (2014).
Neven, K. et al., "Myocardial Lesion Size After Epicardial Electroporation Catheter Ablation After Subxiphoid Puncture," Circ Arrhythm Electrophysiol., 7(4):728-733 (2014).
Neven, K. et al., "Epicardial linear electroporation ablation and lesion size," Heart Rhythm, 11:1465-1470 (2014).
Van Driel, V.J.H.M. et al., "Pulmonary Vein Stenosis After Catheter Ablation Electroporation Versus Radiofrequency," Circ Arrhythm Electrophysiol., 7(4):734-738 (2014).
Van Driel, V.J.H.M. et al., "Low vulnerability of the right phrenic nerve to electroporation ablation," Heart Rhythm, 12:1838-1844 (2015).
Wittkampf, F.H. et al., "Myocardial Lesion Depth With Circular Electroporation Ablation," Circ. Arrhythm Electrophysiol., 5(3):581-586 (2012).
Wittkampf, F.H. et al., "Feasibility of Electroporation for the Creation of Pulmonary Vein Ostial Lesions," J Cardiovasc Electrophysiol, 22(3):302-309 (Mar. 2011).
Office Action for U.S. Appl. No. 15/795,075, dated Jul. 16, 2020, 14 pages.
Office Action for U.S. Appl. No. 15/484,969, dated Jul. 16, 2020, 12 pages.

* cited by examiner

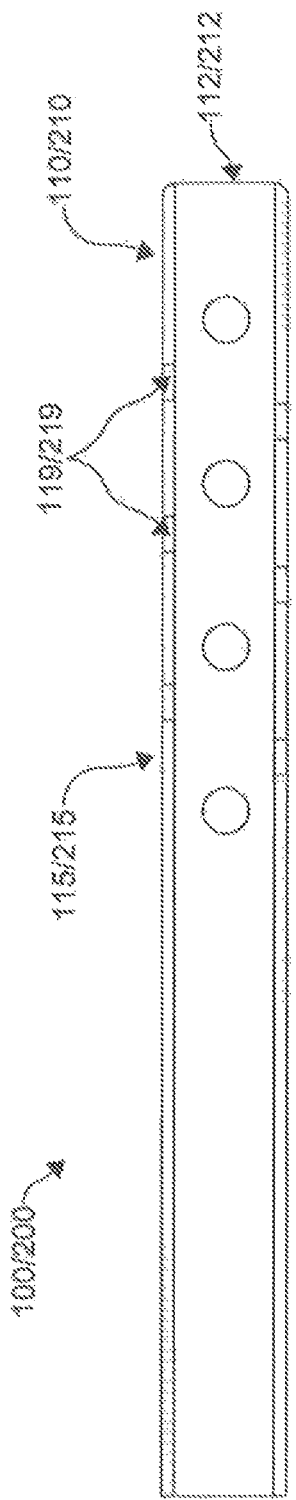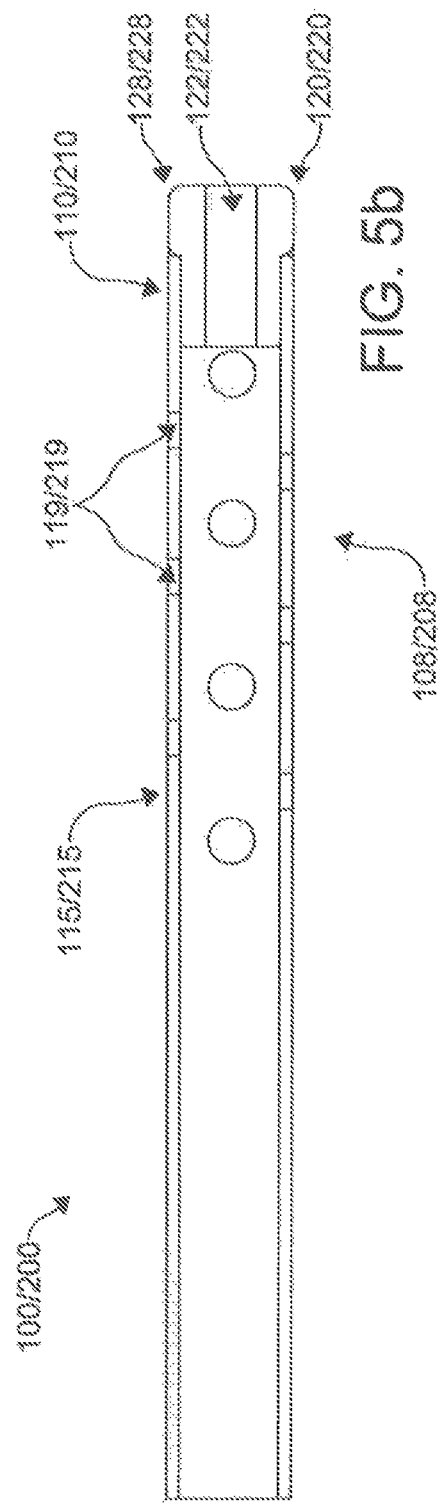

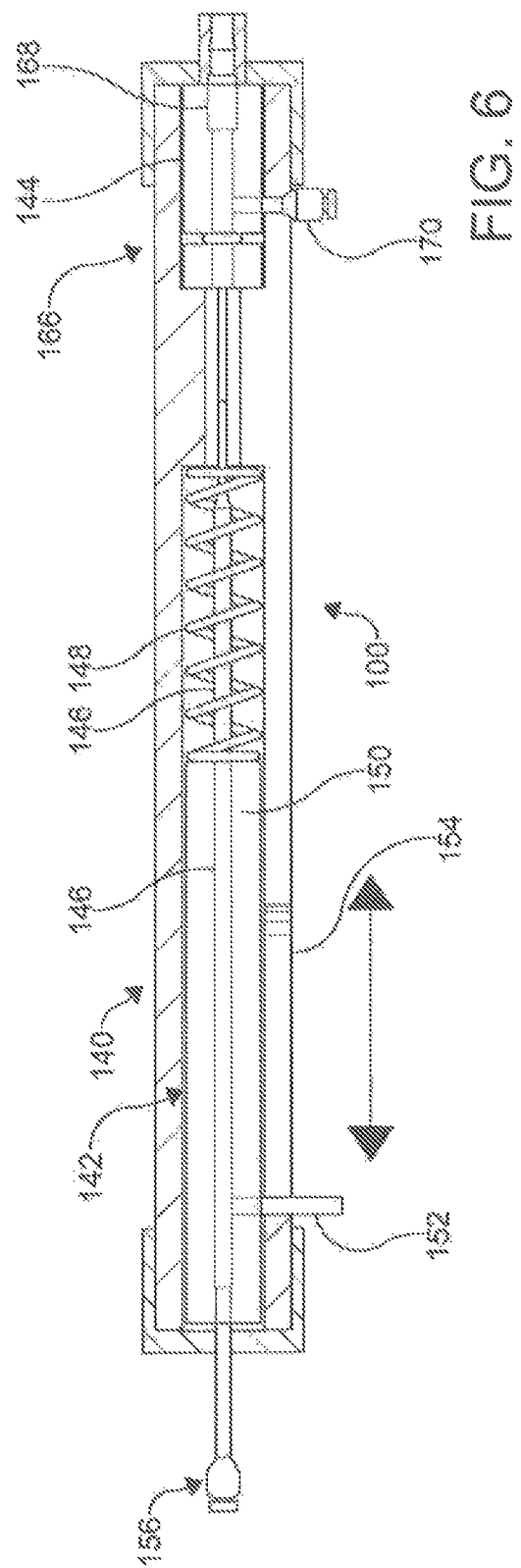

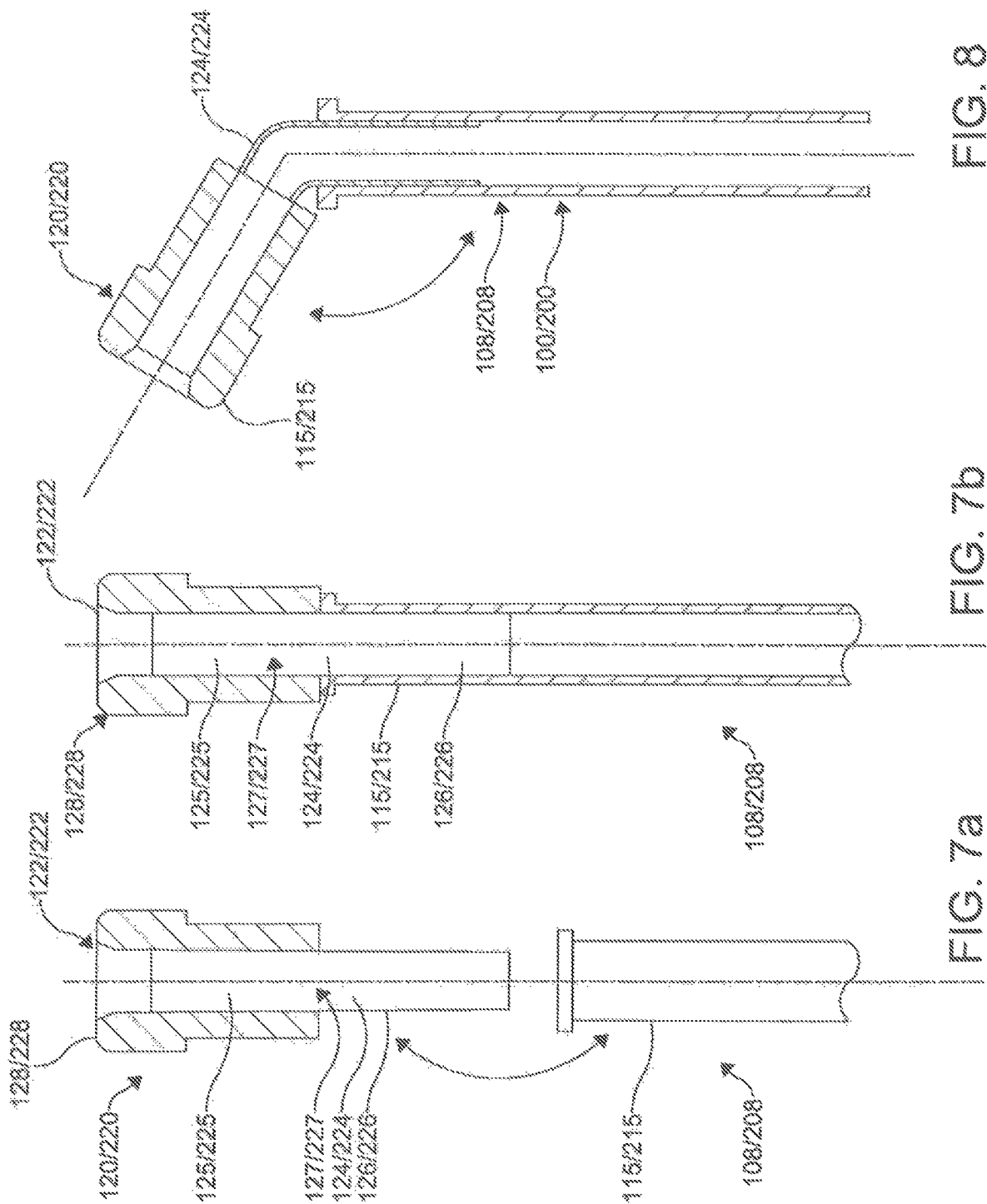

```
1000 ─→
```

┌─────────────────────────────────────────────────────────┐
│ Position distal end 110 of first catheter 100           │
│ proximate a first side of a tissue structure - 1100     │
└─────────────────────────────────────────────────────────┘
                            ↓
┌─────────────────────────────────────────────────────────┐
│ Position distal end 210 of second catheter 200          │
│ proximate a second side of the tissue structure - 1200  │
└─────────────────────────────────────────────────────────┘
                            ↓
┌─────────────────────────────────────────────────────────┐
│ Couple magnet assembly 120 of first catheter 100        │
│ to magnet assembly 220 of second catheter 200 - 1300    │
└─────────────────────────────────────────────────────────┘
                            ↓
┌─────────────────────────────────────────────────────────┐
│ Advance needle 130 of first catheter 100 to exit opening 112 │
│ and be received by opening 212 of second catheter 200 - 1400 │
└─────────────────────────────────────────────────────────┘

FIG. 15

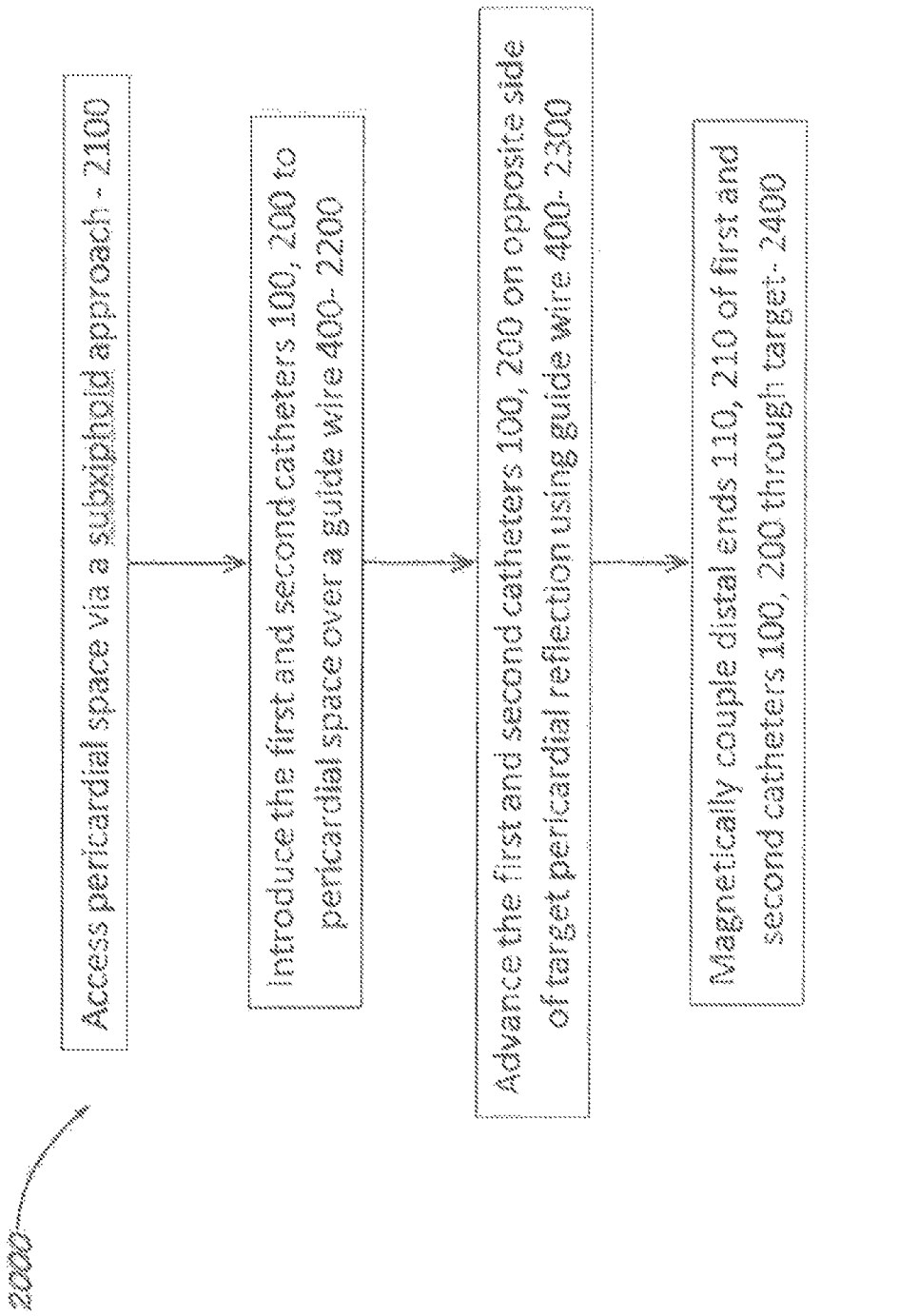

CATHETERS, CATHETER SYSTEMS, AND METHODS FOR PUNCTURING THROUGH A TISSUE STRUCTURE AND ABLATING A TISSUE REGION

CLAIM OF PRIORITY

This application is a continuation of U.S. patent application Ser. No. 15/917,194, filed on Mar. 9, 2018, now abandoned, which is a continuation of U.S. patent application Ser. No. 15/819,726, filed on Nov. 21, 2017, which is a continuation of U.S. patent application Ser. No. 14/400,455, filed on Nov. 11, 2014, now U.S. Pat. No. 9,861,802, which is a U.S. National Phase of PCT/US2013/031252, filed on Mar. 14, 2013 and claims benefit of U.S. Provisional Patent Application No. 61/681,552, filed on Aug. 9, 2012, which are all relied upon and incorporated herein in their entirety by reference.

FIELD

This invention relates to percutaneous catheter systems and ablation catheters. More particularly, this invention relates to percutaneous catheter systems for puncturing through a tissue structure within the body of a subject and to ablation catheters for ablating a selected tissue region within the body of a subject.

BACKGROUND

Atrial fibrillation can be treated by isolating portions of the atria. Such isolation of the atria can be done by open-heart surgery (e.g., a modified Maze procedure) or, most commonly, by a trans-venous catheter technique. In the majority of cases, the doctor cauterizes the left atrial muscle tissues using radiofrequency ablation techniques, with the ablation lesion targeting and/or circumscribing the pulmonary veins. Isolation of these anatomic portions of atria prevents the electrical propagation of the arrhythmia into the remainder of the atria. The operator places electrophysiologic catheters into the right heart. Under fluoroscopic guidance, a catheter is advanced adjacent to the atrial septum. In most cases, a puncture of the atrial septum (right to left) is made with a specialized needle catheter. A guidewire is then advanced into the left atrium.

The trans-septal catheter is removed and a guide catheter is delivered over the wire into the left atrium. An ablation catheter is then advanced into the left atrium under fluoroscopic guidance. Typically, electrophysiologists use additional imaging and mapping technology to improve safety and efficacy of the procedure, such as intercardiac ultrasound, cardiac CT, or non-contact mapping systems. Once the ablation/mapping catheters are in the left atrium, the operator delivers radiofrequency energy to the target sites. The operator moves the ablation catheter in a point-by-point fashion connecting the lesions to effectively electrically isolate the pulmonary veins from the rest of the atrium.

These known procedures typically take 3-6 hours to complete. The procedural success varies between operators and patient selection (success rate is between 50-85% for a single attempt). A substantial minority of patients requires subsequent ablation procedures to "touch up" the prior ablation site. The cost of these procedures is highly variable and increases substantially with duration of procedure and the addition of adjuvant imaging/mapping technology. The current procedures are associated with a 5-6% risk of procedural complications, including a 1/200 risk of stroke due to the need to instrument (i.e., place one or more medical devices into) the left atrium. Other concerning complications include cardiac perforation, tamponade, pulmonary vein stenosis, and atrial-esophageal fistula. Despite attempts to simplify and streamline the procedure, the anatomic variations of the left atrium and pulmonary veins have limited the utility of alternative ablation techniques.

Known epicardial techniques for atrial fibrillation also have various limitations. For example, most current epicardial ablation strategies require the operator to blindly navigate recesses of the pericardial space with an ablation catheter, and reflections of the pericardial anatomy pose an obstacle to delivery of a single contiguous lesion 30 using these techniques. (See the broken line in FIG. 1.) Thus, the pericardial anatomy greatly limits the efficacy and technical ease of current pericardial/epicardial catheter-based procedures.

Although the membranous reflections of the pericardial space that must be breached are very thin and relatively avascular, the angle, spatial limitations, and relative orientation of the surgical access point to the adjacent pericardial reflections do not facilitate simple puncture with a blunt catheter or a standard needle. Moreover, the large vessel and cardiac chambers adjacent to the pericardial reflections make the proposition of blind puncture with conventional catheters very risky.

Currently known cardiac ablation catheters typically require frequent repositioning and/or advanced noncontact mapping techniques to identify incomplete segments in the ablation lesion. For epicardial techniques performed from the pericardial space, such manipulation is fraught with danger and technical limitations. Standard unipolar applications require an externalized grounding pad that results in a diffuse or spherical virtual electrode. Current bipolar ablation techniques utilize electrode pairs that are in close proximity, require the use of cumbersome equipment, and often require entry into both the pericardium and the left atrial blood pool.

Accordingly, there is a need in the pertinent art for devices, systems, and methods for efficiently and reliably locating and puncturing pericardial reflections. There is a further need in the pertinent art for devices, systems, and methods for delivering a single contiguous lesion within the pericardial space without the need for repositioning of equipment.

SUMMARY

Described herein is a percutaneous catheter system including first and second catheters. Each catheter can include a longitudinal axis, a longitudinal length, a proximal portion, and a distal portion. The distal portion of each catheter defines a distal end of its respective catheter. Each catheter defines at least one lumen extending from an opening of the distal end of the catheter toward the proximal portion of the catheter along the longitudinal length of the catheter. Each catheter has a magnet assembly positioned proximate the distal end of the catheter and operatively coupled to the distal portion of the catheter. Optionally, the magnet assembly of each respective catheter can be permanently and/or fixedly attached to a flexible extension mounted within a lumen of the catheter. The magnet assembly of the first catheter is configured for magnetic coupling to the magnet assembly of the second catheter such that the longitudinal axis of the first catheter is substantially axially aligned with the longitudinal axis of the second catheter. The magnet assemblies of the first and second catheters can be configured for magnetic coupling to one another through a tissue structure, such as, for example, a pericardial reflection.

Methods of puncturing through a tissue structure are also described. In exemplary methods, the percutaneous catheter system can permit an operator to deliver a guidewire around target structures, thereby facilitating the deployment of an over-the-wire ablation catheter system. The catheter systems provide means for delivering a single isolating lesion around the pulmonary veins using a subxiphoid pericardial access point. The circumscribing lesion can be produced by any currently known energy sources, including radiofrequency (RF), cryoablation, electroporation, microwave, laser, and ultrasound energy sources. However, the circumscribing lesion can also be produced by a non-energetic ablation.

In exemplary methods, extended bipolar application of high voltage ultra short direct current impulses (HVUSDCI) are used. These impulses produce brief but extremely strong electric fields within the tissue leading to irreversible electroporation (IE), cell death, and injury. However, it should be noted that the total energy applied is relatively low averaging (estimated range 0.025 J to 45 J per pulse). At these energy levels there is very little tissue heating. Thus the mechanism of tissue injury is non-thermal; this is in contrast to RF ablation, which produces thermal tissue ablation through resistive heating.

Also described herein is an ablation catheter for ablating a selected tissue region. The ablation catheter can have a flexible elongate shaft and a plurality of electrodes spaced along a longitudinal length of the flexible elongate shaft. The flexible elongate shaft has a longitudinal axis, a longitudinal length, a proximal portion, a central portion, and a distal portion, with the central portion being positioned between the proximal portion and the distal portion along the longitudinal length of the flexible elongate shaft. The elongate shaft can also define a primary lumen (and, optionally, one or more secondary lumens) of the ablation catheter. The plurality of electrodes can be positioned exclusively within the central portion of the elongate shaft. The electrodes can be separated by high impedance structures. The flexible elongate shaft can be selectively positioned within the body of a subject such that the central portion of the elongate shaft at least partially surrounds the selected tissue region and the proximal and distal portions of the elongate shaft are positioned external to the body of the subject. Upon positioning of the elongate shaft in this manner, each electrode of the plurality of electrodes is configured for selective, independent activation to apply ablative energy to the selected tissue region. Each of the high impedance structures is configured for selective, independent activation to intersect the theoretic field lines created by surrounding electrodes. An ablation catheter system including an ablation catheter, one or more signal generators, and a routing console is also described.

Further described herein are methods of ablating the selected tissue region. In exemplary methods, the ablation catheter can be deployed into the pericardial space with both the proximal and distal portions of the catheter outside the body. The ablation catheter can be more flexible than other clinically available catheter-based ablation devices to thereby permit tissue contact around the left atrial structures. The electrodes of the ablation catheter can be capable of monitoring and/or delivering RF energy, electroporation impulses, and programmed cardiac pacing and/or neurostimulus. Unlike other known ablation catheters, the electrodes of the described ablation catheter also can have the capability of delivering extended bipolar high voltage, ultra-short impulses. The feature of individualizing the activation of each extended bipolar electrode can take advantage of the natural geometry inside the pericardial space to deliver energy to a series of electrodes arranged around the target structure and control the vector of the electrical current.

Once the ablation catheter is deployed, a linear lesion can be created without repositioning the catheter, thereby increasing efficiency and effectiveness (when compared to standard point-by-point techniques). This ablation catheter can provide a stable and contiguous array of electrodes along the target path that can deliver ablation and can also be used to confirm electrophysiologic block using an extended bipolar electrocardiographic technique. The ablation catheter takes advantage of the natural contours of the left atrial epicardial surface to provide reliable and stable electrode contact. Additionally, the high-voltage, ultra-short duration impulses used in electroporation techniques do not require that the electrode be in direct contact with the ablation target.

Moreover, the epicardial positioning can have mechanical advantages over endocardial multi-electrode arrays. Indeed, the positioning of the described ablation catheter can be varied with little effort to provide full circumferential coverage around a target structure. The flexibility of the ablation catheter provides a mechanism for ensuring secure tissue contact and/or tissue proximity around complex anatomic geometry. The natural spatial limitation of the pericardial space can provide a natural mechanism to assure electrode approximation. In addition, high impedance structures (e.g., insulators) found along the ablation catheter can change the contour of the current moving between electrodes. Such changes to the contour can lead to an increased current density at the farthest point along the flow of current and the electrodes.

The risks of performing ablation from the epicardial surface can place the electrodes of the ablation catheter closer to some important bystander structures. However, the electrodes of the ablation catheter can be configured to deliver ablative energy with programmed directional vectors. With RF energy, extended bipolar ablation can result in a 40-50% deeper lesion in the direction of the programmed vector. With electroporation, the potential for creating a preferential directional injury vector is greater. In exemplary methods, extended bipolar irreversible electroporation (which cause no thermal injury) can be delivered.

These and other objects and advantages of the invention will become apparent from the following detailed description of the preferred embodiment of the invention.

Both the foregoing general description and the following detailed description are exemplary and explanatory only and are intended to provide further explanation of the invention as claimed. The accompanying drawings are included to provide a further understanding of the invention and are incorporated in and constitute part of this specification, illustrate several embodiments of the invention, and together with the description serve to explain the principles of the invention.

BRIEF DESCRIPTION OF THE FIGURES

These and other features of the preferred embodiments of the invention will become more apparent in the detailed description in which reference is made to the appended drawings wherein:

FIGS. 5a-e are a series of cross sectional views of a portion of the catheter of the system of FIG. 3.

FIG. 6 is a cross sectional view of a portion of a catheter of the system of FIG. 3.

FIGS. 7a-b are cross sectional views of the assembly of a portion of a catheter of system FIG. 3.

FIG. 8 is a cross sectional view of the portion of the catheter of assembled in FIGS. 7a-b.

FIG. 15 is a depiction of a process to puncture a tissue structure using a percutaneous catheter system according to an aspect.

FIG. 24 is a depiction of a process to puncture a tissue structure using percutaneous catheter system according to an aspect.

DETAILED DESCRIPTION

The present invention can be understood more readily by reference to the following detailed description, examples, drawings, and claims, and their previous and following description. However, before the present devices, systems, and/or methods are disclosed and described, it is to be understood that this invention is not limited to the specific devices, systems, and/or methods disclosed unless otherwise specified, and, as such, can, of course, vary. It is also to be understood that the terminology used herein is for the purpose of describing particular aspects only and is not intended to be limiting.

The following description of the invention is provided as an enabling teaching of the invention in its best, currently known embodiment. To this end, those skilled in the relevant art will recognize and appreciate that many changes can be made to the various aspects of the invention described herein, while still obtaining the beneficial results of the present invention. It will also be apparent that some of the desired benefits of the present invention can be obtained by selecting some of the features of the present invention without utilizing other features. Accordingly, those who work in the art will recognize that many modifications and adaptations to the present invention are possible and can even be desirable in certain circumstances and are a part of the present invention. Thus, the following description is provided as illustrative of the principles of the present invention and not in limitation thereof.

As used throughout, the singular forms "a," "an" and "the" include plural referents unless the context clearly dictates otherwise. Thus, for example, reference to "a delivery conduit" can include two or more such delivery conduits unless the context indicates otherwise.

As used herein, the terms "optional" or "optionally" mean that the subsequently described event or circumstance may or may not occur, and that the description includes instances where said event or circumstance occurs and instances where it does not.

The word "or" as used herein means any one member of a particular list and also includes any combination of members of that list.

It is contemplated that the disclosed devices and systems can comprise elements of the devices and systems described in U.S. Pat. No. 6,314,963, the disclosure of which is incorporated herein by reference in their entireties.

Figure 1:
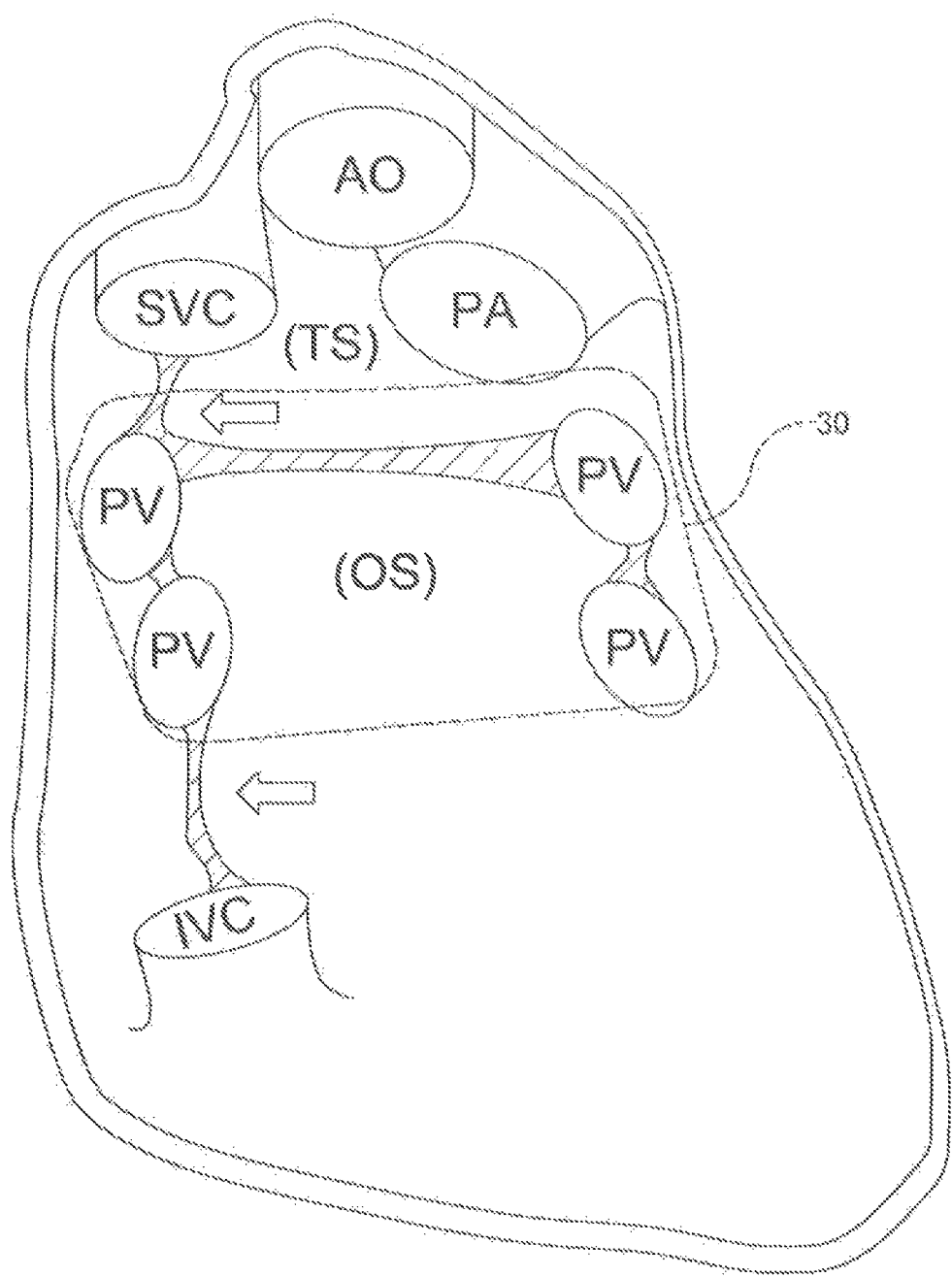
FIG. 1 depicts the posterior pericardial anatomy with a membranous reflection illustrating a hypothetical lesion delivered to the left atria (note: heart is absent from the illustration).
Figure 2:
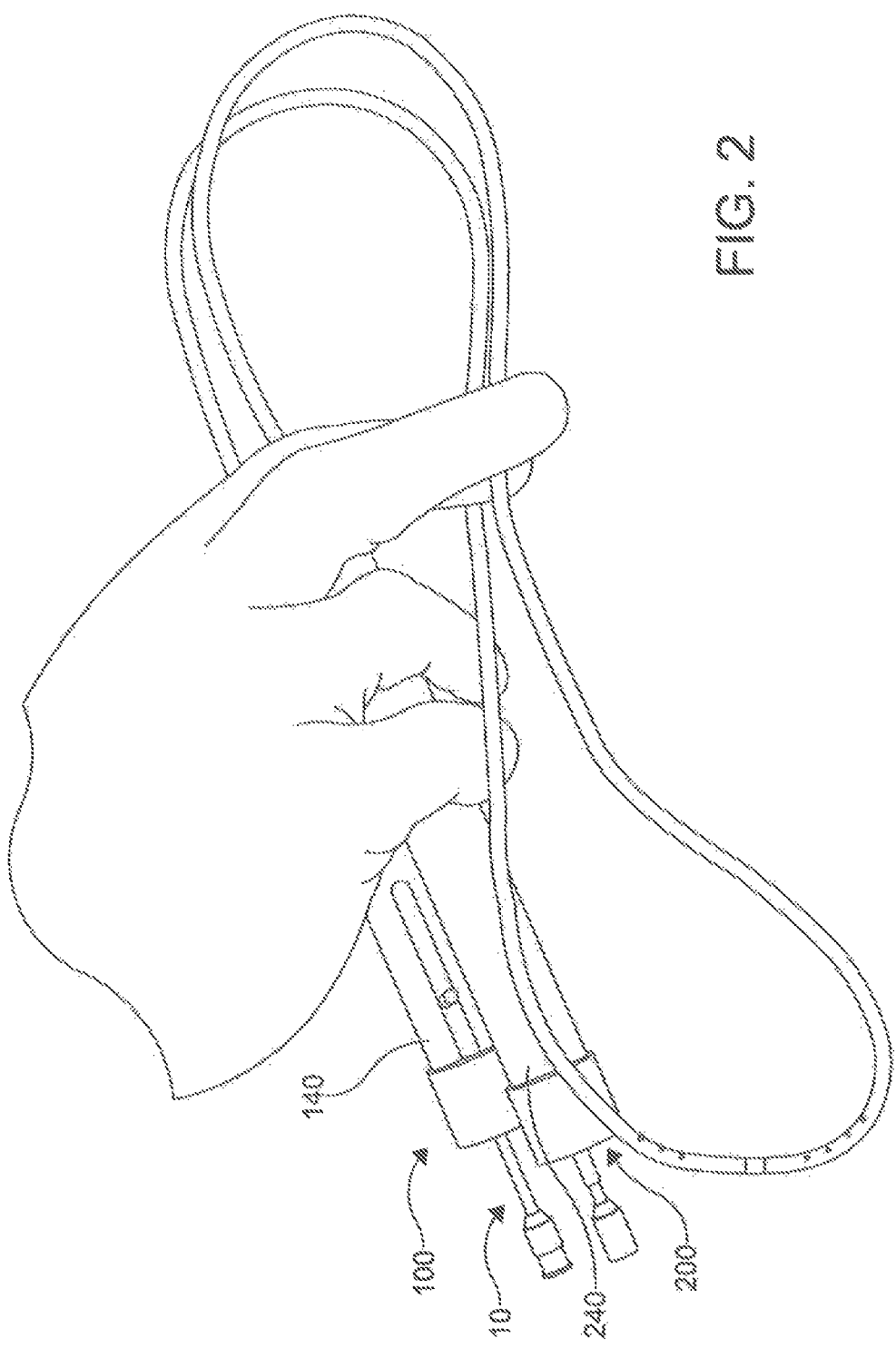
FIG. 2 is a perspective view of a percutaneous catheter system according to an aspect.

It is contemplated that the percutaneous catheter system 10 and ablation catheter 20 of the present invention can allow an operator to deliver a single isolating lesion around the pulmonary veins of a subject using a subxiphoid pericardial access point. The circumscribing lesion can be produced by any of the currently available energy sources, including, for example and without limitation, HVUS-DCI, RF, cryoablation, electroporation, microwave, laser, biologics, radiation, small molecule chemicals (e.g., ethanol ablation) and ultrasound. However, it is contemplated that the circumscribing lesion can be produced by any ablative energy source. In use, it is contemplated that, once an operator achieves a stable catheter position for the ablation catheter 20, delivery of a single circumscribing lesion 30 around the pulmonary veins (as shown in FIG. 1) of the subject can become much simpler. The atrial fibrillation ablation technique described herein can require fewer steps, catheters, time, and equipment than conventional atrial fibrillation ablation techniques. Further, it is contemplated that the described percutaneous catheter system 10 can minimize or avoid the need for expensive advanced mapping and imaging equipment; instead, the described percutaneous catheter system 10 can permit usage of a purely anatomic approach. Consequently, it is contemplated that the described percutaneous catheter system can minimize the expense of atrial fibrillation ablation, thereby making atrial fibrillation ablation to a larger population of patients.

Catheter System for Puncturing Through a Tissue Structure

With reference to FIGS. 2-24, disclosed herein, is a percutaneous catheter system 10 for use within the body of a subject. In one aspect, the percutaneous catheter system 10 comprises a first catheter 100 and a second catheter 200. The first catheter 100 can be referred to as the male catheter 100 and the second catheter 200 can be referred to as the female catheter 200. In this aspect, the first catheter 100 and the second catheter 200 can each have respective longitudinal axes 102, 202, longitudinal lengths 104, 204, proximal portions 106, 206, and distal portions, 108, 208. In exemplary aspects, the first and second catheters 100, 200 can each have a longitudinal length 104, 204 ranging from about 20 cm to about 50 cm. In another exemplary aspect, the longitudinal length 104, 204 of the first catheter 100 and the second catheter 200 are approximately the same. While the length of the catheters 100, 200 in relation to one another is not critical in many aspects, it is important that the catheters 100, 200 are configured to work as a pair. However, the lengths of the catheters 100, 200 collectively need to have a combined length that is long enough to reach the key areas of the anatomy for which the catheter system 10 is being used. In these aspects, it is contemplated, following magnetic coupling between the first catheter 100 and the second catheter 200, the total length of the first catheter 100 and the second catheter 200 can range from about 40 cm to about 100 cm.

In other exemplary aspects, at least one of the first catheter 100 and the second catheter 200 can be flexible. In other exemplary aspects, both the first catheter 100 and the second catheter 200 can be flexible. The catheters 100, 200 should be comprised of a material that is also kink resistant. In an aspect, the catheters 100, 200 can be comprised of kink resistant material such as expanded PTFE and/or more standard biocompatible materials (coil reinforced silicon, PFA, Pebax, and/or PVC). The construction can utilize expanded PTFE with progressively decreasing density distally, however other construction techniques could be employed. The stiffer proximal segment provides necessary column strength and transmission of torsional force for navigation. In an aspect, the distal portions 106 (which can range between 10-20 cm) are more flexible to permit a-traumatic manipulation and navigation by over the wire techniques through tortuous anatomy. In some embodiments, in order to prevent kinking, braided reinforcement, as well as other types of reinforcement, can be utilized.

In an exemplary aspect, the first and second catheters 100, 200 are configured to be flexible enough so that the catheters 100, 200 can permit a 180° turn around a 1.5 cm obstacle. However, the catheters 100, 200 can be made to perform to other standards (e.g., perform 180° turns around various sized obstacles) in other exemplary embodiments.

In another aspect, the distal portion 108 of the first catheter 100 can define a distal end 110 of the first catheter 100. In an aspect, the distal end 110 can have a nominal outer diameter between 1 mm to 5 mm to accommodate a magnet assembly 120. In this aspect, the distal end 110 of the first catheter 100 can define an opening 112. In an aspect, the end of the proximal portion 106 is configured to be larger than the distal end 110 in order to facilitate the manipulation of the catheter 100 at the handle 140, discussed in more detail below.

In an additional aspect, the first catheter 100 can define at least one lumen 116, 118 extending from the opening 112 of the distal end 108 toward the proximal portion 106 of the first catheter 100 along at least a portion of the longitudinal length 104 of the first catheter 100. The lumen can be defined by an outer shaft 115 of the catheter 100. In a further aspect, the first catheter 100 can comprise a first magnet assembly 120 positioned proximate the distal end 110 of the first catheter 100 and operatively coupled to the distal portion 108 of the first catheter 100.

In another aspect, the distal portion 208 of the second catheter 200 can define a distal end 210 of the second catheter 200. In an aspect, the distal end 210 can have a nominal outer diameter between 1 mm to 5 mm to accommodate a magnet assembly 220. In an aspect, the distal end 210 of the second catheter 200 can define an opening 212. In an aspect, the end of the proximal portion 206 is configured to be larger than the distal end 210 in order to facilitate the manipulation of the second catheter 200 through the use of a handle 240, discussed in more detail below.

In an additional aspect, the second catheter 200 can define at least one lumen 216, 218 extending from the opening 212 of the distal end 210 toward the proximal portion 206 of the second catheter 200 along at least a portion of the longitudinal length 204 of the second catheter 200. The lumen 216, 218 can be defined by an outer shaft 215 of the second catheter 200. In a further aspect, the second catheter 200 can comprise a second magnet assembly 220 positioned proximate the distal end 210 of the second catheter 200 and operatively coupled to the distal portion 208 of the second catheter 200.

In an exemplary aspect, the first catheter 100 and the second catheter 200 can have a nominal outer diameter of 1 to 5 mm and in other respects the geometry of catheter 100 and 200 will be similar to provide a symmetric and complementary magnetic coupling surface for the magnet assemblies 120, 220. However, in other aspects, the outer diameter of the catheters 100, 200 can vary. In an exemplary aspect, the first and second catheters 100, 200 can have an inner diameter configured to accommodate a needle tube 130 discussed in more details below. In an exemplary aspect, inner diameter of the first and second catheters 100, 200 can be configured to accommodate a needle tube 130 of approximately 1.473 mm in diameter. However, in other aspects, the inner diameter of the catheters 100, 200, as well as the diameter of the needle tube 130, can vary. In other aspects, when magnetic coupling and guide wire transfer are the only desired functions, the catheters 100/200 may not have a needle component.

In an exemplary aspect, the first magnetic assembly 120 of the first catheter 100 is configured for magnetic coupling to the second magnet assembly 220 of the second catheter 200. In this aspect, it is contemplated that the first magnetic assembly 120 can be configured for magnetic coupling to the second magnet assembly 220 such that the longitudinal axis 102 of the first catheter 100 is substantially axially aligned with the longitudinal axis 202 of the second catheter 200. It is further contemplated that the first magnet assembly 120 can be configured for magnetic coupling to the second magnet assembly 220 through a tissue structure within the body of the subject, discussed further below.

It is contemplated that the at least one lumen of the first catheter 100 can comprise a primary lumen 116. Similarly, it is contemplated that the at least one lumen of the second catheter 200 can comprise a primary lumen 216. Optionally, in another exemplary aspect, the at least one lumen of the first catheter 100 can further comprise one or more auxiliary lumens 118. Similarly, it is contemplated that the at least one lumen of the second catheter 200 optionally can further comprise one or more auxiliary lumens 218. In an aspect, the primary lumen 116, 216 and the auxiliary lumen 118, 218 can be separate by an inner shaft 117, 217 in each catheter 100, 200, with the primary lumen 116, 216 being contained within the inner shaft 117, 217, and the auxiliary lumen 118, 218 being contained between the inner shaft 117, 217 and the outer shaft 115, 215. The primary lumen 116, 216 can be configured to receive the needle tube 130. In some aspects, the inner shaft 117, 217 can move up and down the outer shaft 115, 215 of the catheters 100, 200 respectively.

Optionally, it is contemplated that the one or more auxiliary lumens 118 of the first catheter 100 can be configured for delivery of one or more fluids to the opening 112 of the distal end 110 of the first catheter 100, while the one or more auxiliary lumens 218 of the second catheter 200 can be configured for delivery of one or more fluids to the opening 212 of the distal end 210 of the second catheter 200. Optionally, it is further contemplated that the one or more auxiliary lumens 118 of the first catheter 100 can be configured for application of suction to the opening 112 of the distal end 110 of the first catheter 100, while the one or more auxiliary lumens 218 of the second catheter 200 can be configured for application of suction to the opening 212 of the distal end 210 of the second catheter 200.

In another aspect, the auxiliary lumens 118, 218 can perform the delivery of fluids and the application of suction through irrigation ports/side openings/side holes 119, 219 approximate the openings 112, 212 of the distal ends 110, 210 of the catheters 100, 200. In one optional exemplary aspect, the at least one lumen of the first catheter 100 and/or second catheter 200 can comprise a primary lumen 116, 216 and an auxiliary lumen 118, 218, with the auxiliary lumen 118, 218 radially surrounding the primary lumen 116, 216.

In one aspect, the first catheter 100 can further comprise a needle 130 operatively positioned within the primary lumen 116 of the first catheter 100, as shown in FIGS. 5*e*, 9-12 and 14. The needle 130 can further comprise a flexible tubular needle 130. In an exemplary aspect, the flexible tubular needle 130 can comprise a modified hypodermic needle spirally cut circumferentially around a shaft 132 of the needle 130. The needle 130 can have a progressive pitch to the coil providing increasing flexibility at a distal tip 134. The needle 130 can be made of materials that include, but are not limited to, metal, plastic, or other suitable compounds. In an aspect, the needle 130 can be a composite with a coating to improve mechanical and/or functional characteristics (examples include, but are not limited to, a lubricious polymer, insulator, electrical components, and/or biocompatible metals). A proximal portion of the needle 130 can connect to a mounting hub, the inner shaft 117, and/or other elements to provide a method of fixation within the catheter 100 and/or a deployment mechanism 146 in the catheter handle 140. In an exemplary aspect, the needle 130 is mounted to the inner shaft 117 of the first catheter 100. In other aspects, the needle 130 can extend the length of the catheter 100. In additional aspects, the needle 130 can be connected to the inner wall of the outer shaft 115 of the catheter 100.

In an exemplary embodiment, the tubular needle 130 can have a flexibility to accommodate a 1.5 cm turn radius. However, in other aspects, the flexibility of the needle 130 can vary depending on the needs of the application. In one exemplary aspect, it is contemplated that the needle 130 of the first catheter 100 can have a distal puncturing surface 134 and be configured for selective axial movement relative to the longitudinal axis 102 of the first catheter 100.

In an aspect, the distal tip 134 is configured to serve as a puncturing surface 134. In an exemplary aspect, the puncturing surface 134 can be flared at a 45° angle and OD 2.5 mm. However, in other aspects, the puncturing surface 134 can be configured differently. It is still further contemplated that the distal puncturing surface 134 of the needle 130 of the first catheter 100 can be configured to puncture through a tissue structure within the body of the subject positioned between the distal ends 110, 210 of the first and second catheters 100, 200 respectively when the ends 110, 210 are magnetically coupled, discussed below.

Figure 14:
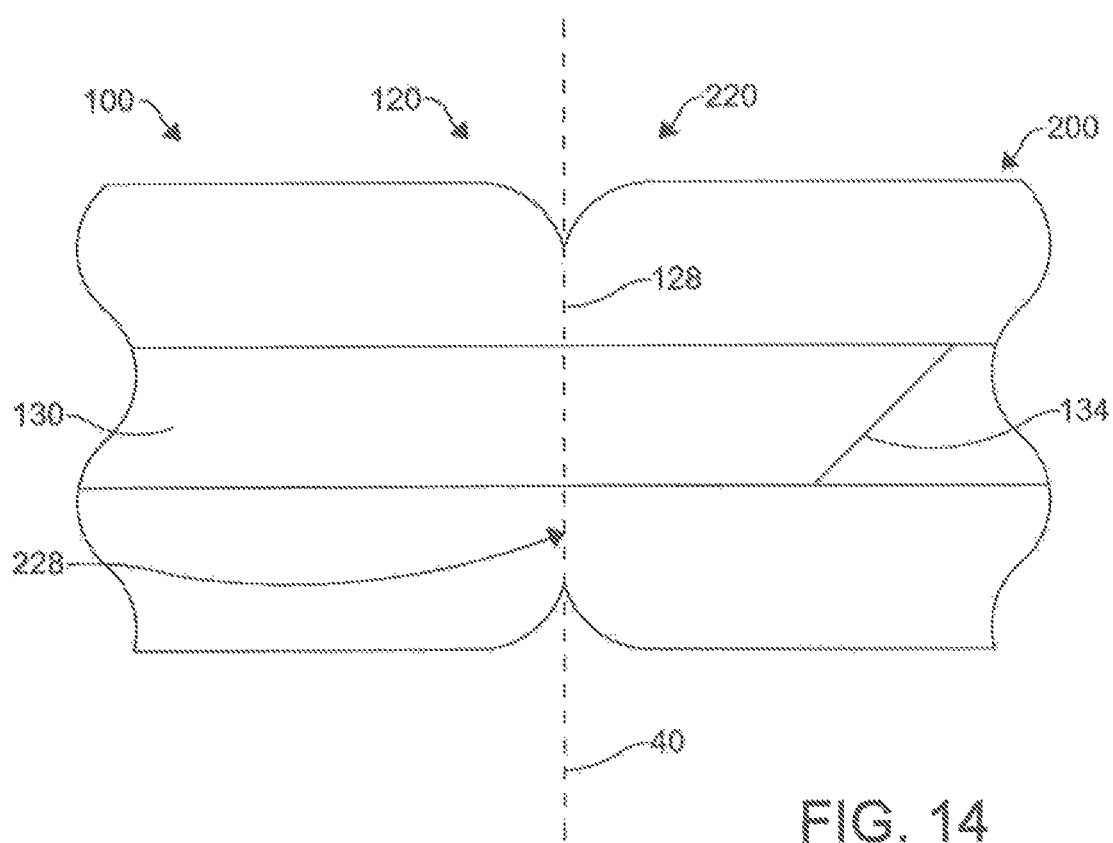
FIG. 14 is a cross-sectional schematic view of the "docked" catheter system of FIG. 13.
Figure 17:
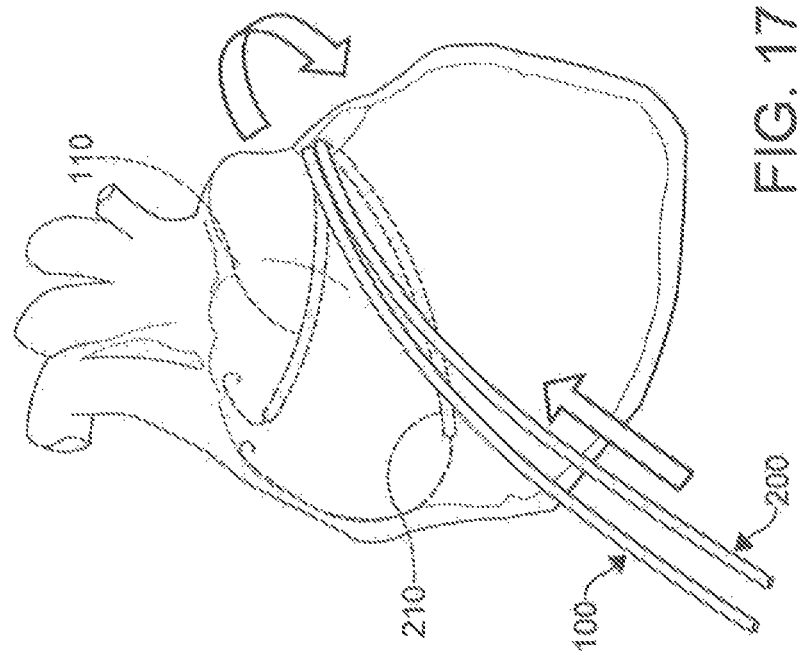
FIGS. 16-23 are illustrations of the placement and use of a percutaneous catheter system according to an aspect.

Optionally, in one aspect, the needle 130 of the first catheter 100 can be retractably secured within the primary lumen 116 of the first catheter 100. In this aspect, the needle 130 of the first catheter 100 can define a delivery lumen 138. In this aspect, the delivery lumen 138 of the needle 130 of the first catheter 100 can be configured to receive a guide wire 300 (shown in FIG. 3). The guide wire 300 can be utilized before and after the placement of the catheters 100, 200. In this aspect, upon receipt of at least a portion 134 of the needle 130 of the first catheter 100 within the opening 212 of the distal end 210 of the second catheter 200 (as shown in FIG. 14), the delivery lumen 138 of the needle 130 of the first catheter 100 can be configured to permit transfer of a guide wire 300 from the first catheter 100 to the second catheter 200.

Figure 3:
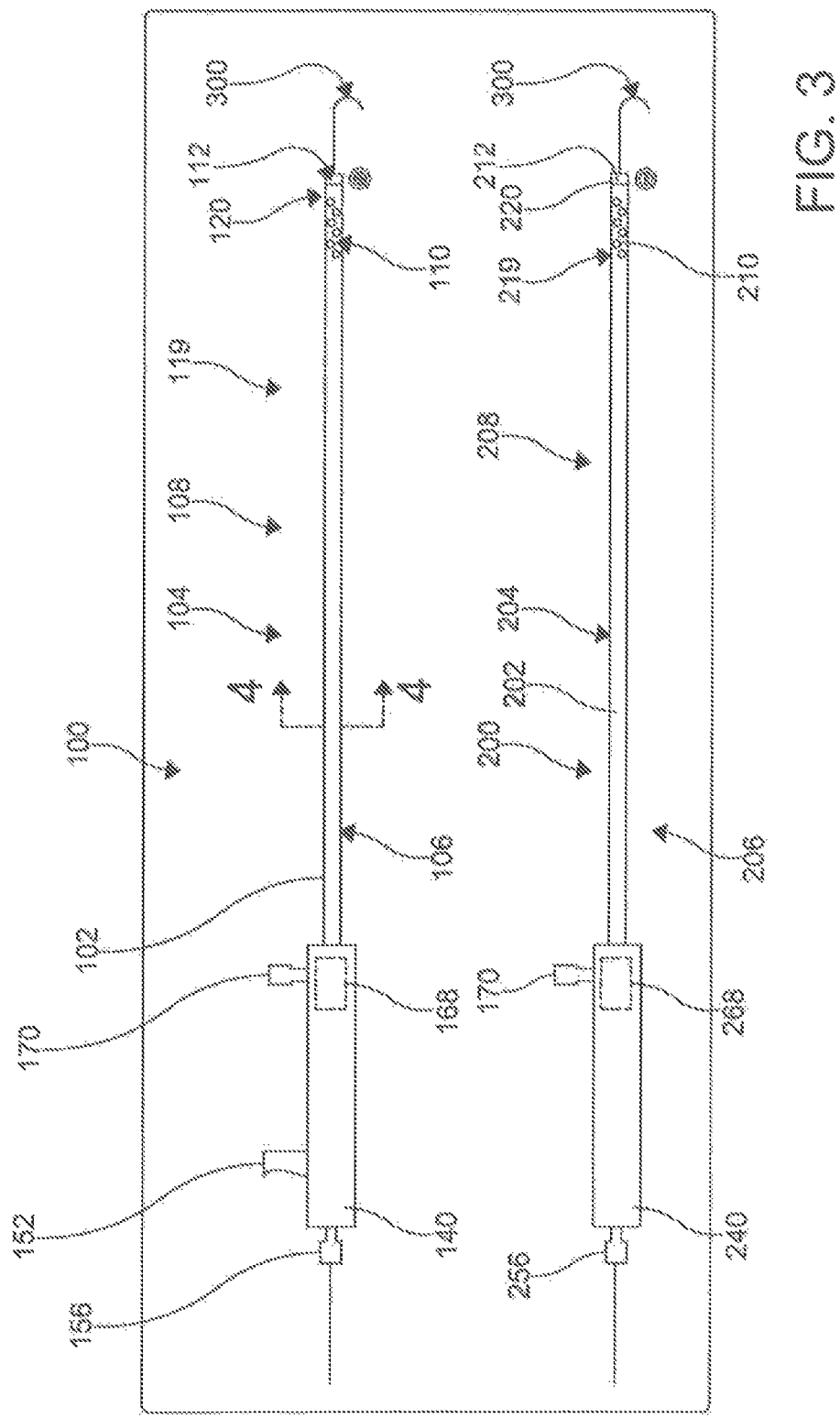
FIG. 3 is a schematic plane view of a percutaneous catheter system according to an aspect.
Figure 4:
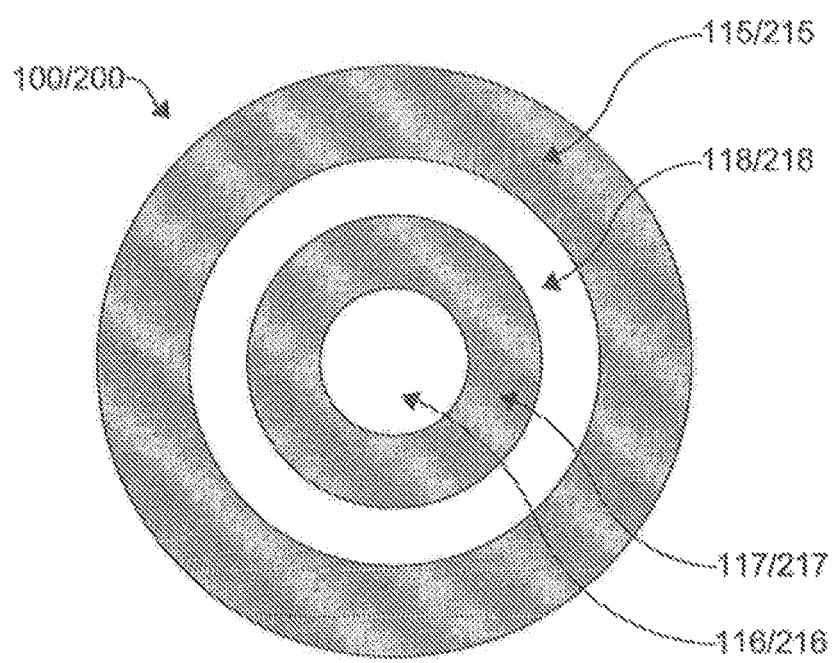
FIG. 4 is a cross sectional view of a catheter of the system of FIG. 3 along line 4-4.

In an aspect, as illustrated in FIGS. 3 and 6, the handles 140, 240 are found approximate the proximal ends 106, 206 of the catheters 100, 200. The handles 140, 240 can be made of a rigid material, such as, but not limited to, machined aluminum, carbon fiber, and the like. The handles 140, 240 provide the means of manual manipulation of the catheters 100, 200 when in use. The handles 140, 240 provide a place to apply force to advance, withdrawal, and apply rotational torsion to catheters 100, 200.

As shown in FIG. 6, the handle 140 of the male catheter 100 (i.e., the catheter 100 operating the needle 130) can include a proximal chamber 142 and a distal chamber 144. In an aspect, the proximal chamber 142 can contain a stylus/integrated lever 146 that is connected to the inner shaft 117 of the catheter 100. The stylus/integrated lever 146 allows for the independent manipulation of the needle 130 within the outer shaft 115 of the catheter 100. In an aspect, the stylus 146 allows for the independent manipulation of the inner catheter 117 to manipulate the needle 130 within the outer shaft 115 of the catheter 100. In a further aspect the control of the inner shaft 117 by the integrated lever 146 provides a means to transmit force distally and deploy the needle 130 through the central bore 122 of the magnetic assembly 120. The stylus/integrated lever 146 can include a compression spring 148 that ensures that the needle 130 is not deployed until actually called on by the user. In an aspect, the spring 148 prevents the stylus/integrated lever 146 from the inner shaft 117 from deploying the needle until called upon.

In an aspect, the integrated lever 146 includes a rigid tube 150 connected to the proximal end of the spring 148. The rigid tube 150 is hollow, and allows passage of the guidewire 300 and other components to the distal end 110 of the catheter 100. A projection 152 extends from the rigid tube 150 through a slot 154 found on the outer portion of the handle 140. The projection 152 allows the user to activate the integrated lever/stylus 146, compressing the spring 148 and pushing the needle 130 distally along the catheter 100. Lastly, the handle 140 can include a guidewire entry point 156. In an aspect, the inner shaft 117 passes through a fluid hub 168 found in the distal chamber 144.

In an aspect, the handle 240 of the female catheter 200 can include all of the same components of as described above for the male catheter 100, but it is not necessary. For example, when a female catheter 200 is used that does not employ a needle 230, the handle 240 does not need to have a integrated lever and the associated components to control the needle and inner shaft 217. In another aspect, the catheter pair 100/200 can be constructed without an inner needle 130/230, and be equipped to form magnetic coupling with central lumen for the passage of a guide wire. In other aspects, the female catheter 200 can have a proximal chamber 242 and a distal chamber 244, with the proximal chamber 242 providing a guidewire entry point 256 to receive a guide wire 300 to pass through to the primary lumen 216 and the distal chamber 244 including a fluid hub 268.

In an aspect, the handles 140, 240 can include a hemostasis/fluid management system. The fluid management systems include proximal valves (not shown) that prevent unwanted fluid leakage through the primary lumens 116, 216 of the respective male catheter 100 and female catheter 200. In addition, the proximal valves prevent the introduction of unwanted air through the centers lumen 116, 216. In an aspect, a second fluid valve (166 in FIG. 6) can be used to provide a seal of the auxiliary lumens 118, 218. Both the first and second fluid valves can include silicon o-rings and various other seal-creating mechanisms.

Fluid hubs 168, 268 can be found within the handles 140, 240 near the proximal ends 106, 206 of the male catheter 100 and female catheter 200 respectively. The fluid hub 168, 268 of each catheter 100, 200 can be in communication with their respective auxiliary lumen 118, 218. Fluid ports 170, 270 provide access to the fluid hubs 168, 268. In an aspect, the combination of the fluid ports 170, 270, fluid hubs 168, 268, auxiliary lumen 118, 218 and side openings 119, 219 create the fluid management system. The fluid management system provides for the delivery of radio contrast agents for intra-pericardial navigation under x-ray fluoroscopic guidance. In addition, the fluid management systems provide a means to inject and suck moderate volumes of fluid through the lumen 118, 218 quickly. This is specifically used to inject and withdraw radio contrast agents and/or other fluids (including but not limited to saline, medications, etc.) within the pericardial space; thus accentuating anatomic boundaries. The system, through the side openings 119, 219 can also be used to manage and/or drain a pericardial effusion.

Figure 5C:
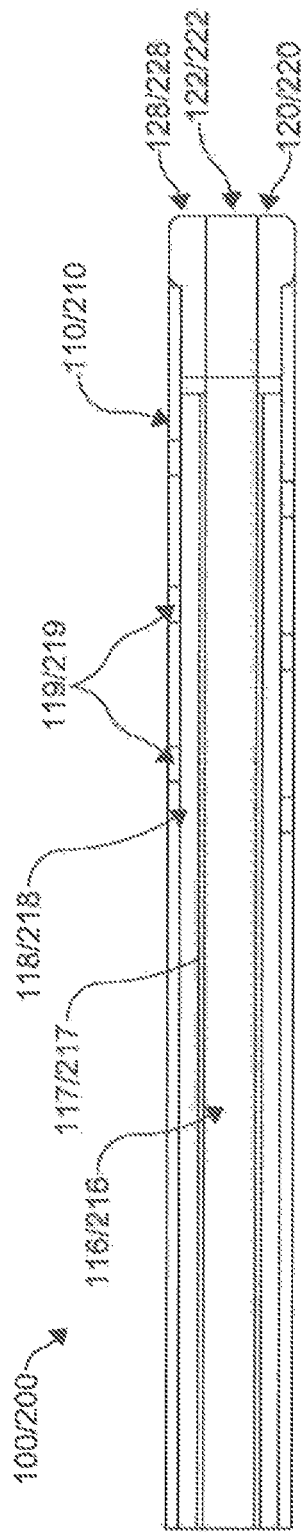
Figure 5D:
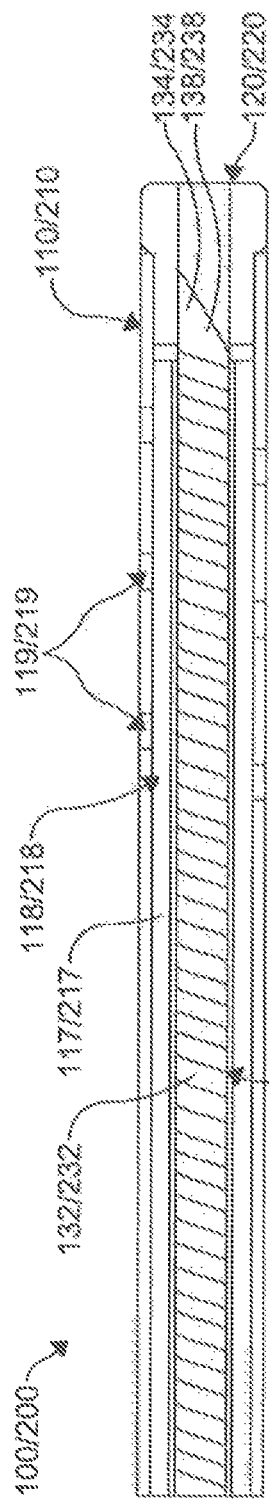
Figure 5E:
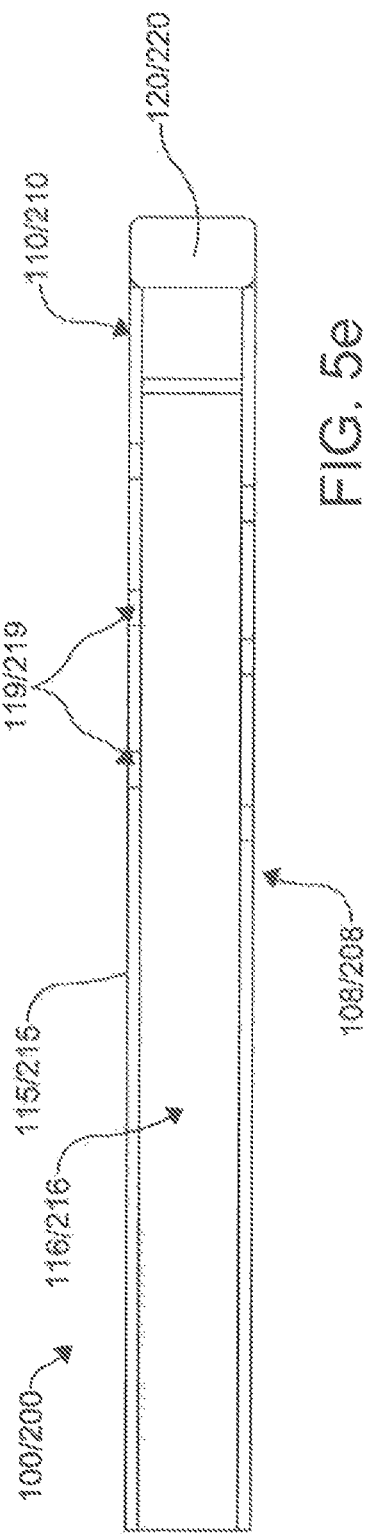
Figure 9:
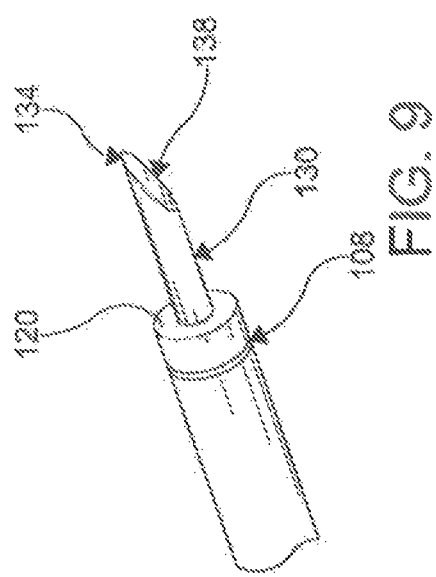
FIG. 9 is a perspective view of a needle of the percutaneous catheter system of FIG. 2.
Figure 10:
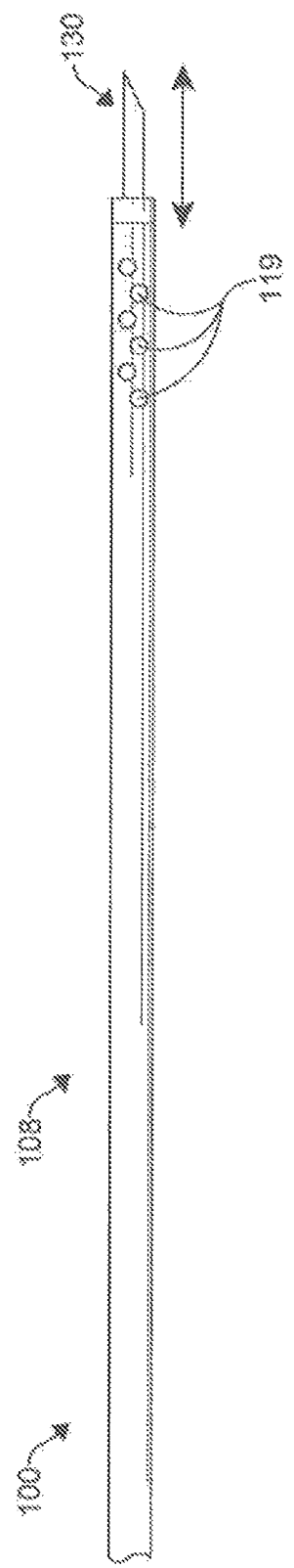
FIG. 10 is a schematic plane view of a needle of the percutaneous catheter system of FIG. 3.
Figure 11:
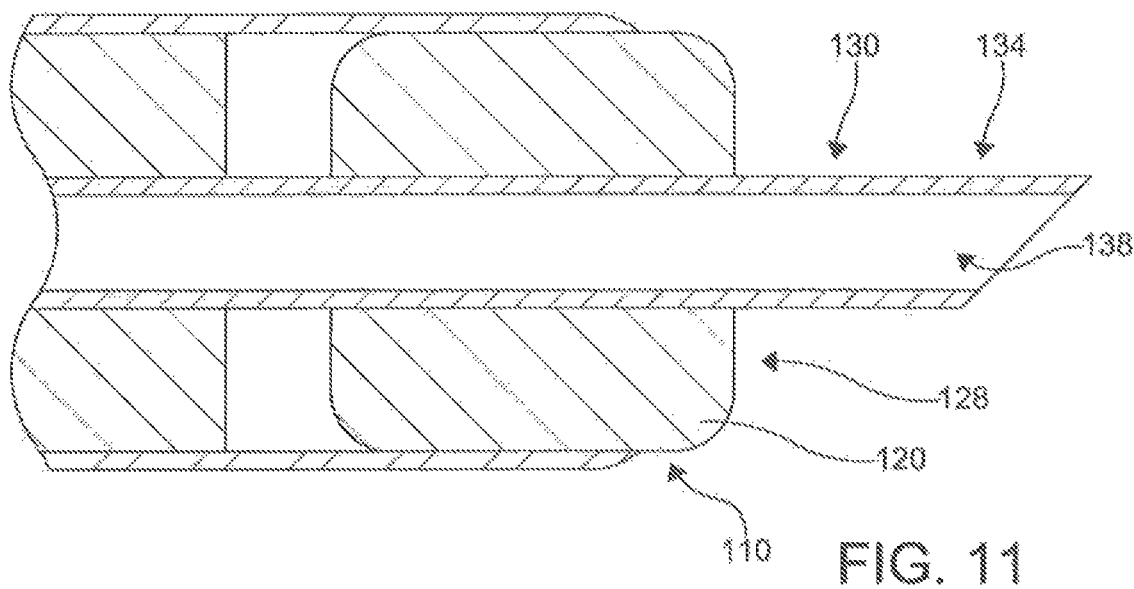
FIG. 11 is a cross sectional view of a portion of a catheter of the percutaneous catheter system of FIG. 3.
Figure 12:
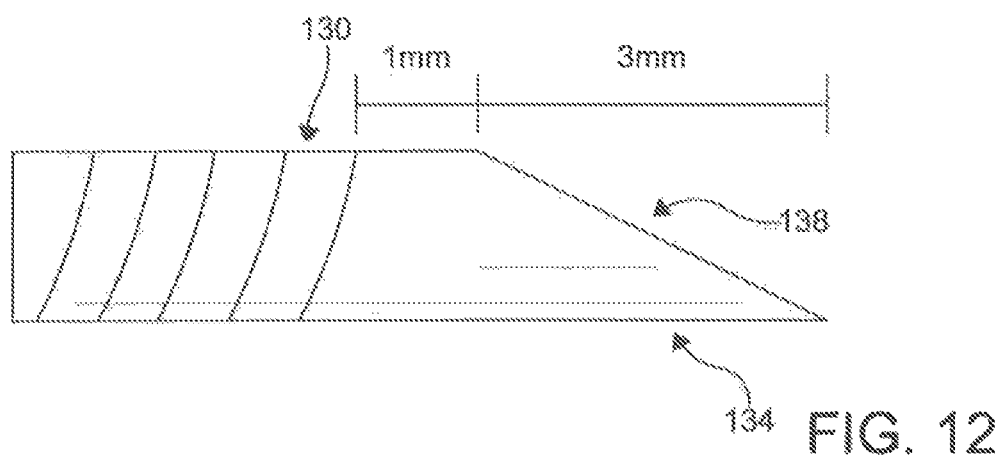
FIG. 12 is a schematic view of a needle of the percutaneous catheter system of FIG. 3.
Figure 13:
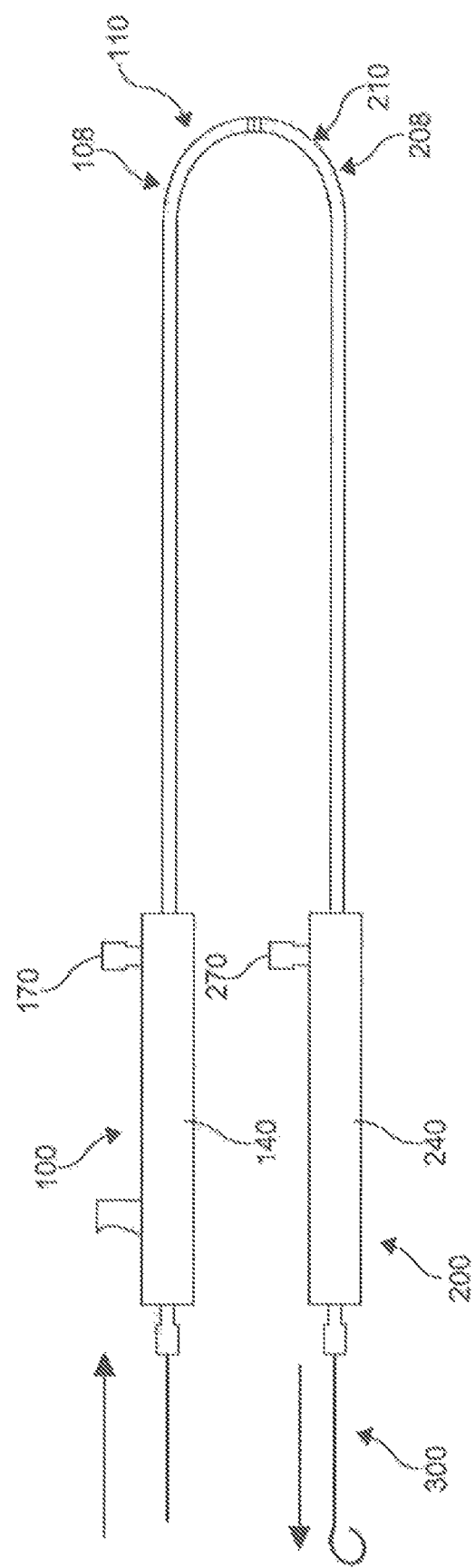
FIG. 13 is a schematic plane view of docked catheters of percutaneous catheter system of FIG. 3.

In another aspect, it is contemplated that the first magnet assemblyl 20 of the first catheter 100 can be positioned within the primary lumen 116 of the first catheter 100, as shown in FIG. 5. In this aspect, it is further contemplated that the second magnet assembly 220 can be positioned within the primary lumen 216 of the second catheter 200. It is still further contemplated that the first magnet assembly 120 of the first catheter 100 can define a central bore 122 configured to receive the needle 130 of the first catheter 100. Similarly, it is contemplated that the second magnet assembly 220 of the second catheter 200 can define a central bore 222 configured to receive the needle 130 of the first catheter 100.

In an aspect, as shown in FIGS. 7a-b and 8, the magnet assemblies 120, 220 can be coupled to the distal ends 110, 210 of respective catheters 100, 200 through the use of a flexible needle guide 124, 224. The flexible needle guides 124, 224 include a distal portion 125, 225 and a proximal portion 126, 226. The flexible needle guides 124, 224 can include central lumen 127, 227 that extend the length of the guides 124, 224 and are configured to receive the needle 130, 230. The distal portions 125, 225 of the needle guides 124, 224 are secured within central bores 122, 222 of the magnet assemblies 120, 220, with the proximal portions being secured within the primary lumens 116, 216 at the distal portions 108, 208 of the catheters 100, 200. The needle guide 124, 224 can be attached coaxially through adhesive or by mounting over a thin walled rigid tube that has been affixed to the magnetic assembly and extends proximally from the magnet 120, 220.

The needle guides 124, 224 provide a means to maintain central alignment of the inner and outer shafts of the catheters 100, 200 while allowing independent degrees of lengthwise movement. In an aspect, the flexible needle guides 124, 224 can provide a way to introduce a fixed and/or adjustable angle at the distal ends 110, 210 of the catheters 100, 200. In the cases where the distal portions 110, 210 and magnet assemblies 120, 220 of the catheters 100, 200 meet curved portions, the flexible needle guide 124, 224 provides a flexible curved angle between the most distal portion 125, 225 and proximal portions 126, 226, as shown in FIG. 8. Further, the guides 124, 224 prevent the needle 130 from exiting the opening 112, 212 when the distal end 110, 210 encounters a curve, preventing accidental punctures. In an aspect, a rigid tube guide 124, 224 can be utilized. In such an aspect, the segment of the needle guide 124, 224 extending proximally from the magnet may be aligned with the long axis 102, 202 of the inner lumen 116, 216 or the rigid component may bend providing a means to introduce a fixed curve into the tip of the assembled catheter. The variations in performance requirements and mounting techniques will influence magnet assembly 120, 220 and needle guide 124, 224 dimensions and shape.

It is still contemplated that the first magnet assembly 120 can have a distal surface 128 substantially flush with the distal end 110 of the first catheter 100. Similarly, it is contemplated that the second magnet assembly 220 of the second catheter 200 can have a distal surface 228 substantially flush with the distal end 210 of the second catheter 200. In exemplary aspects, the first magnet assembly 120 can be permanently fixedly secured to the first catheter 100. Similarly, it is contemplated that the second magnet assembly 220 can be permanently fixedly secured to the second catheter 200. However, in other aspects, the first and second magnet assemblies can be removably coupled to the first and second catheters 100, 200 respectively.

In an aspect, the magnet assembly 120 of the first catheter 100 and the magnet assembly 220 of the second catheter 200 are configured to be magnetically attracted to one another. In an exemplary aspect, it is desired that the magnet assemblies 120, 220 are strong enough to automatically magnetically couple to one another when the magnet assemblies 120, 220 come within approximately 1 cm of each other. In the exemplary catheter we found magnetic field strength between 0.5 kG to 1.5 kG was ample to provide the desired coupling characteristics. However, in all aspects, the strength of the magnetic attraction has to be strong enough to magnetically couple the magnet assemblies 120, 220 and hold them together magnetically on opposite sides of human tissue. In an aspect, the magnetic attraction can occur automatically. In another aspect, the magnetic attraction between the two magnet assemblies 120, 220 can be manually controlled.

It is contemplated that, upon magnetic coupling between the first magnet assembly 120 of the first catheter 100 and the second magnet 220 assembly of the second catheter 200 such that the longitudinal axis 102 of the first catheter 100 is substantially axially aligned with the longitudinal axis 202 of the second catheter 200, the needle 130 can be configured for axial movement relative to the longitudinal axis 102 of the first catheter 100 such that at least a portion 134 of the needle 130 exits the opening 112 of the distal end 110 of the first catheter 100 and is received within the opening 212 of the distal end 210 of the second catheter 200.

Similarly, in another optional aspect, the second catheter 200 can further comprise a needle 230 operatively positioned within the primary lumen 216 of the second catheter 200. In this aspect, the needle 230 of the second catheter 200 can be configured for selective axial movement relative to the longitudinal axis 202 of the second catheter 200. It is further contemplated that, upon magnetic coupling between the magnet assemblies 120, 220 of the first and second catheters 100, 200 such that the longitudinal axis 102 of the first catheter 100 is substantially axially aligned with the longitudinal axis 202 of the second catheter 200, the needle 230 of the second catheter 200 can be configured for axial movement relative to the longitudinal axis 202 of the second catheter 200 such that at least a portion 232 of the needle 230 exits the opening 212 of the distal end 210 of the second catheter 200 and is received within the opening 212 of the distal end 210 of the first catheter 100. The needle 230 can also include a delivery lumen 238.

In use, the disclosed percutaneous catheter system 10 can be incorporated into methods of puncturing through a tissue structure within the body of a subject (method 1000), as shown in FIG. 15. In one aspect, an exemplary method of puncturing through a tissue structure within the body of a subject can comprise positioning the distal end 110 of the first catheter 100 proximate a first side of the tissue structure (step 1100). In another aspect, the exemplary method can comprise positioning a distal end 210 of a second catheter 200 proximate a second side of the tissue structure (step 1200). In an additional aspect, the exemplary method can comprise magnetically coupling the first magnet assembly 120 of the first catheter 100 to the second magnet assembly 220 of the second catheter 200 through the tissue structure such that the longitudinal axis 102 of the first catheter 100 is substantially axially aligned with the longitudinal axis 202 of the second catheter 202 (step 1300). In a further aspect, the exemplary method can comprise selectively advancing a needle 130 through the at least one lumen 114 (e.g., the primary lumen 116 in the exemplary aspect) of the first catheter 100 such that at least a portion 132 of the needle 130 exits the opening 112 of the distal end 110 of the first catheter 100 and is received within the opening 212 of the distal end 210 of the second catheter 200, piercing the tissue structure 40 (step 1400), as shown in FIG. 14. In exemplary aspects, the tissue structure can comprise an anatomical pericardial reflection adjacent to the heart of the subject. In these aspects and others, both catheters 100, 200 can employ a guide wire 300 to reach their positions incrementally, with the operator using standard over-the-wire maneuvering techniques to advance the catheters 100, 200.

Figure 16:
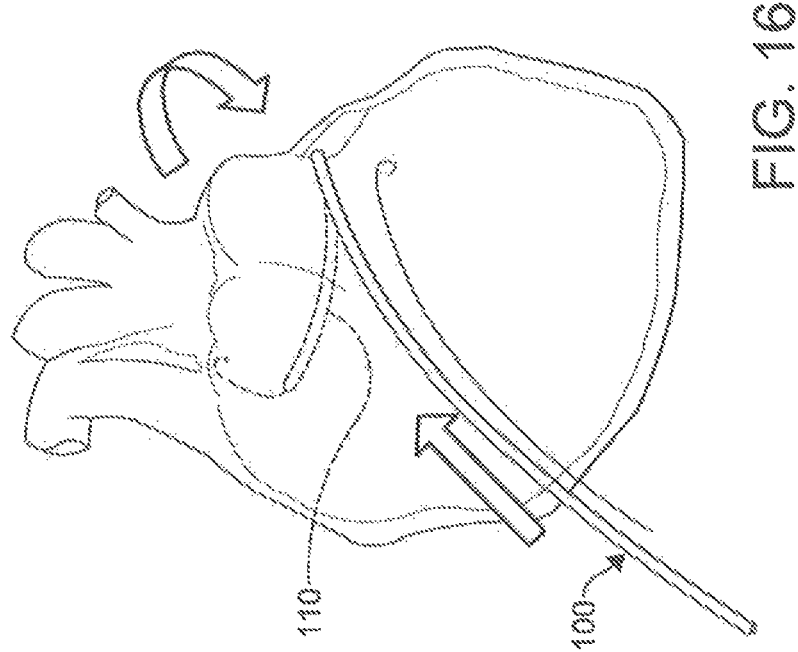
Figure 19:
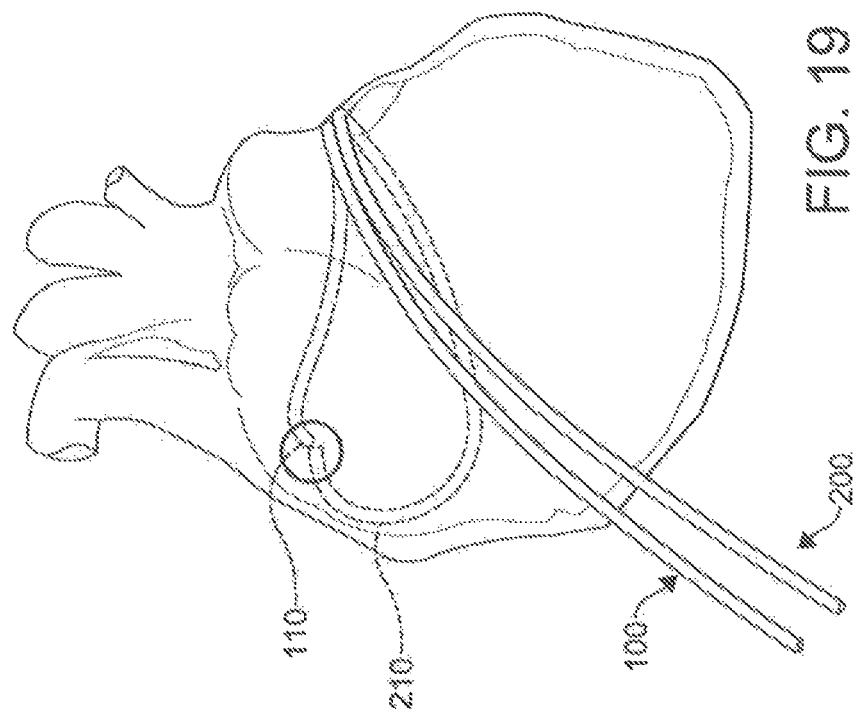
Figure 18:
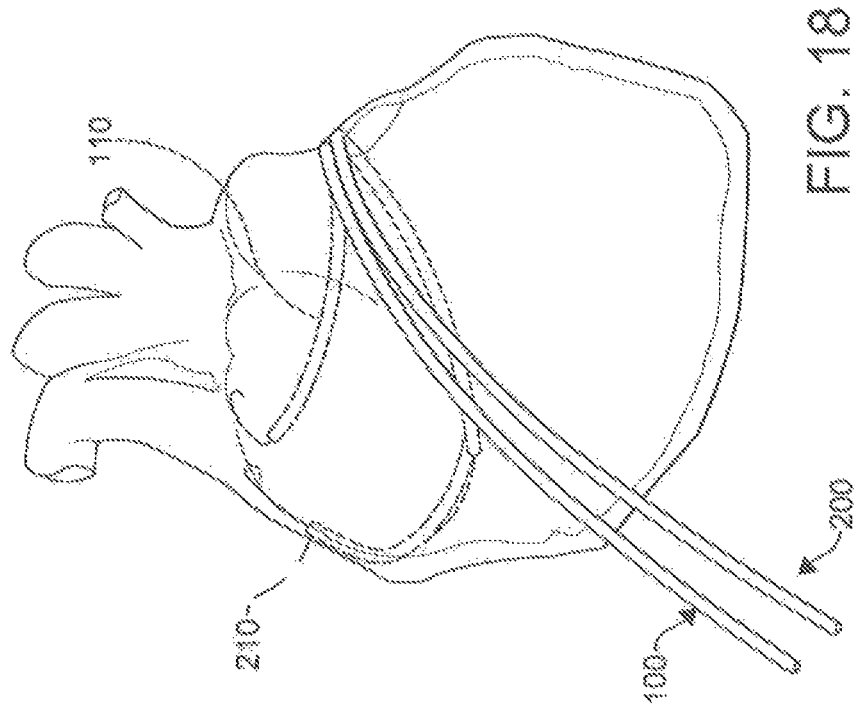
Figure 21:
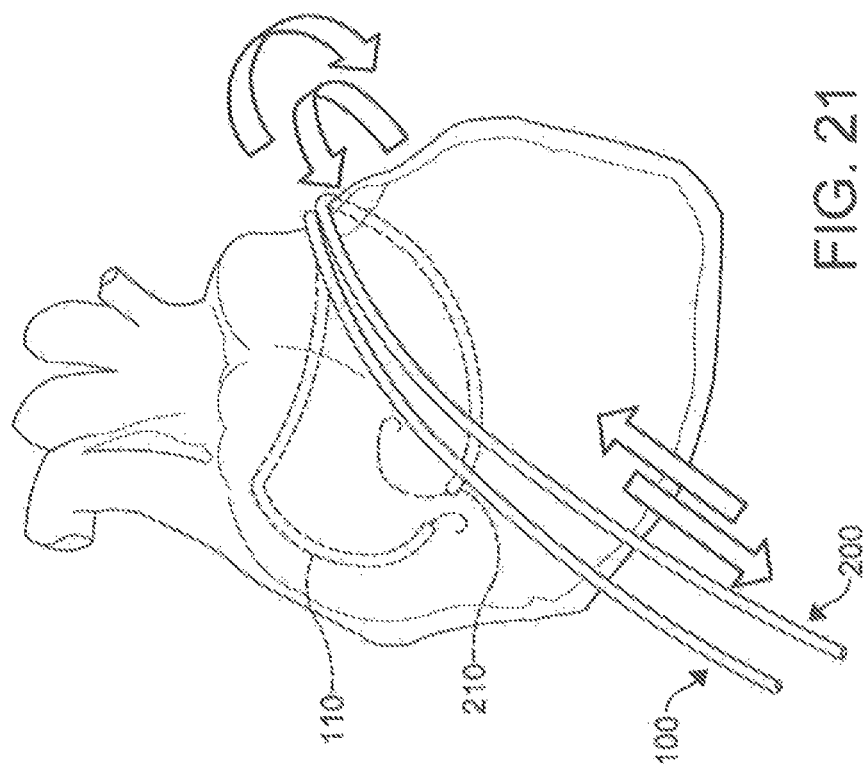

In an exemplary aspect of the method (1000) discussed above, the distal end 110 of the first catheter 100 being positioned in the transverse sinus (step 1100), as illustrated in FIG. 16. The distal end 210 of the female catheter 200 can be introduced over the anterior/superior aspect of the ventricle (FIG. 17), and then advanced toward the right pericardial "gutter" by way of the posterior/inferior cardiac border (FIG. 18) to be proximate the first catheter 100 (step 1200). When in place, the magnet assemblies 120, 220 of the male and female catheters 100, 200 can then be magnetically coupled (Step 1300), as illustrated in FIG. 19. The needle 130 can then exit the distal end 110 of the male catheter 100 to be received within the bore 222 of the magnet assembly 220 of the female catheter (step 1400), as shown in FIG. 14.

Figure 20:
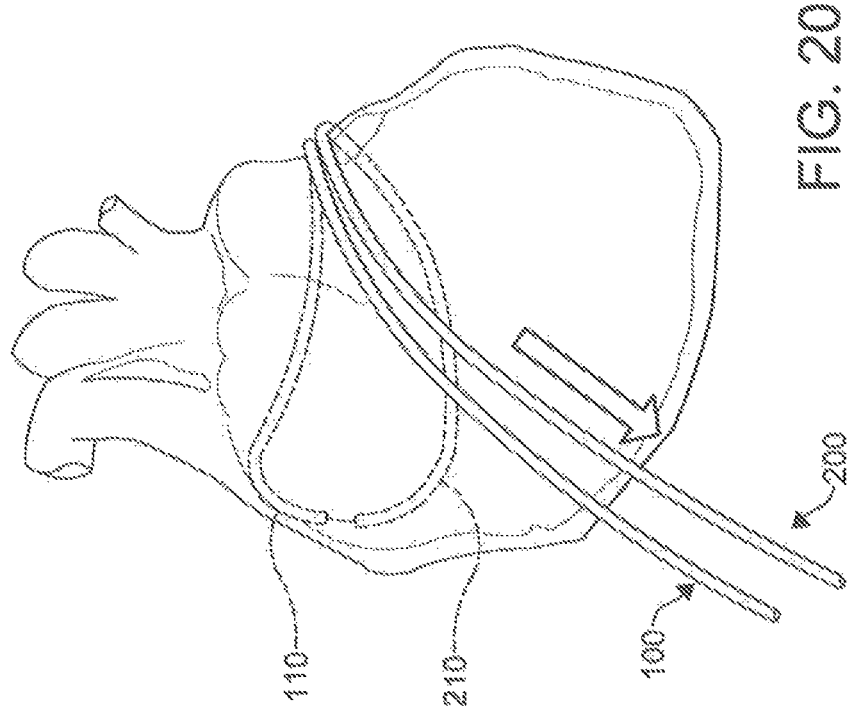
Figure 23:
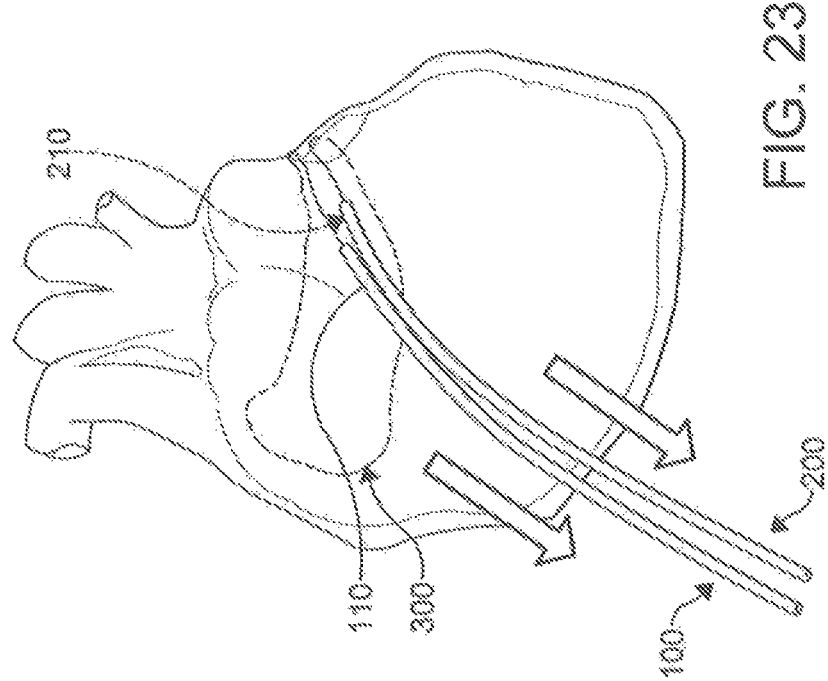
Figure 22:
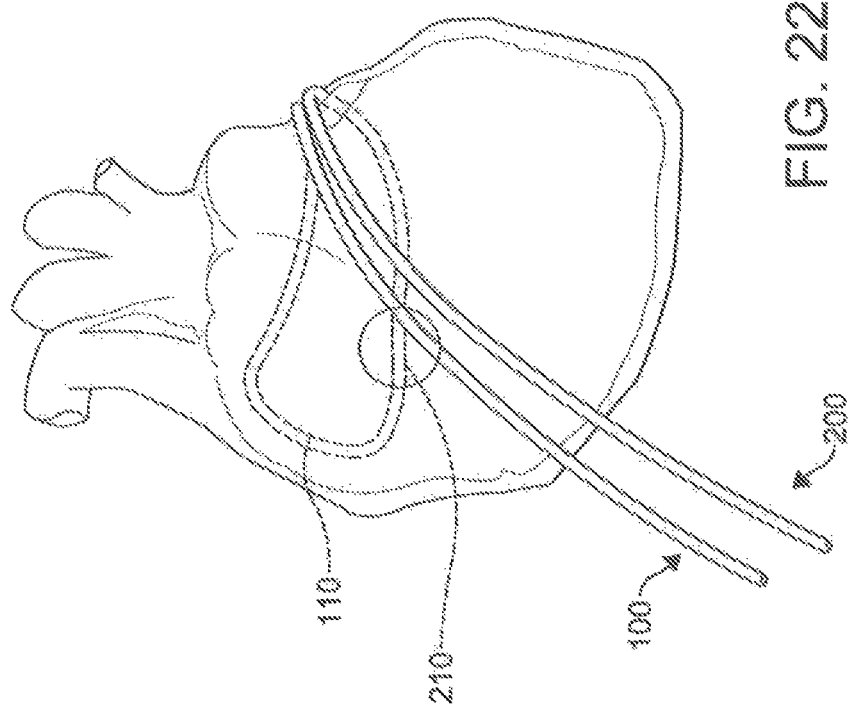

In addition, steps of the method as discussed above can be repeated during certain procedures. Referring back to the exemplary aspect discuss above, after step 1400 has been completed, the second catheter 200 can be withdrawn into the obtuse sinus (step 1100), as shown in FIG. 20. The male catheter 100 can be positioned adjacent the second catheter 200 (step 1200)(FIG. 21) and couple the targeted pericardial reflection sandwiched in between (steps 1300), as shown in FIG. 22. The needle 130 can then puncture the tissue (step 1400). After the needle 130 has punctured the tissue, the guidewire 300 can be advanced from the proximal male catheter across the magnetic coupled ends and out the proximal end of the female catheter 200. The catheters 100, 200 can be removed, leaving the guidewire 300 in place, as shown in FIG. 23. In additional aspects, it is contemplated that the percutaneous catheter system 10 can be used to cross and/or puncture through other anatomic boundaries within the body of a subject. For example, it is contemplated that the percutaneous catheter system 10 can be used to cross and/or puncture through the pericardium and plural space (to create a pericardial window). In another exemplary aspect, it is contemplated that the percutaneous catheter system 10 can be used to create access between various organ structures in a controlled manner (e.g., between the bladder and the perineum or between ventricles in a brain (for drainage or placement of electrodes)). In yet another exemplary aspect, it is contemplated that the percutaneous catheter system can be used intravascularly to create an AV fistula in a dialysis patient. In still another exemplary aspect, it is contemplated that the percutaneous catheter system 10 can be used to accomplish trans-venous delivery of electrodes, such as electrodes used in pacemakers and/or nerve stimulators, when an electrical generator is positioned remotely from an electrode target and surgical tunneling is not a desirable option.

In exemplary applications, it is contemplated that the percutaneous catheter system 10 can safely perform punctures across membranous pericardial reflections. The catheter system 10 can be introduced into the pericardium by one of several common transcutaneous techniques.

Figure 25:
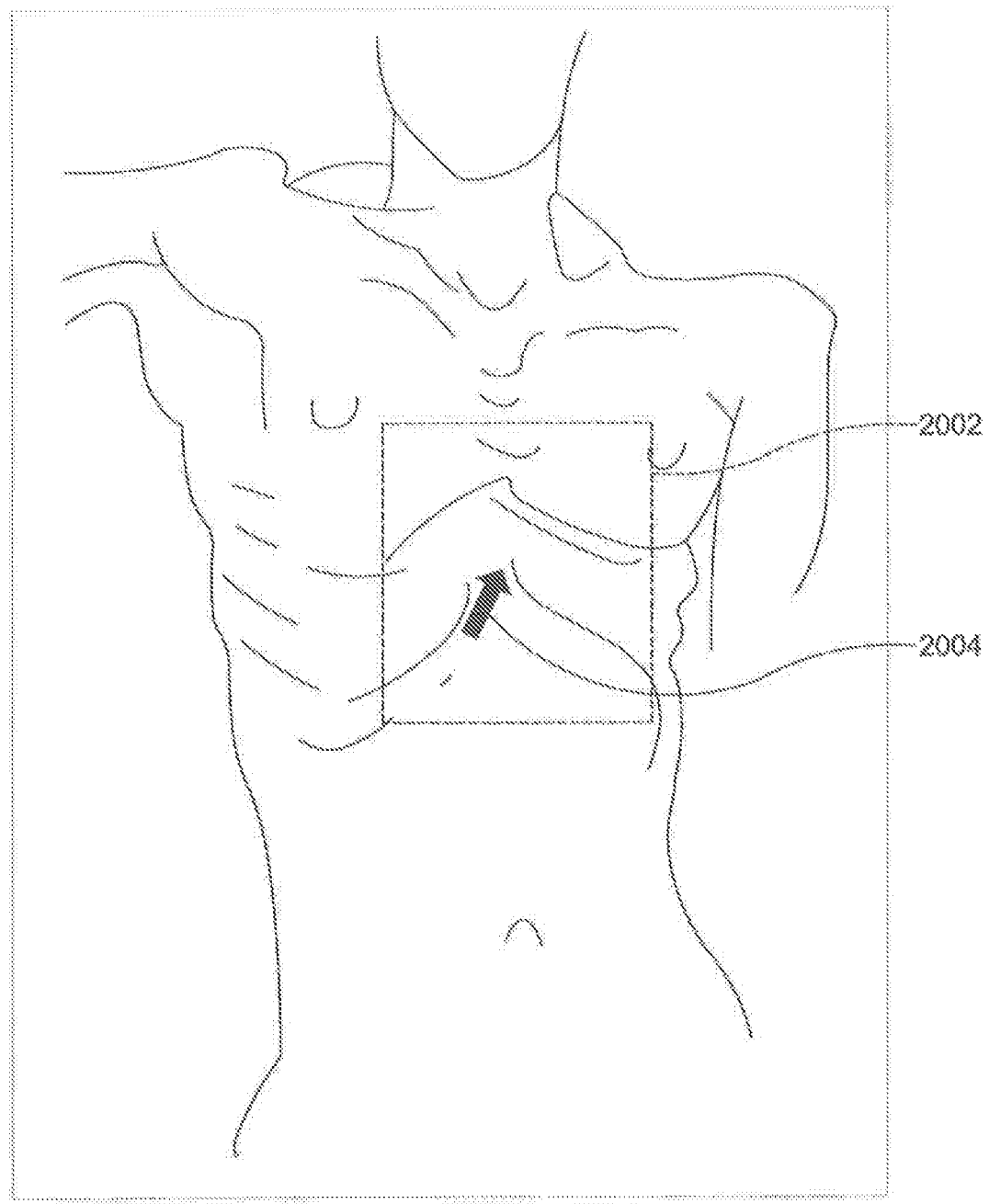
FIG. 25 is a schematic representation of the entry site for the process shown in FIG. 15.

The following exemplary method (2000) can be employed following access to the pericardial space via a subxiphoid approach (step 2100) as shown in FIG. 24; however, it is understood that the method described below can also be employed following other conventional approaches. FIG. 25 illustrates the sterile field 2002 for percutaneous access into the pericardial space. The entry site 2004 is also shown. It is contemplated that the respective longitudinal lengths 104, 204 of the first and second catheters 100, 200 of the percutaneous catheter system 10 can be sufficiently long to permit advancement of the first and second catheters 100, 200 into the transverse sinus of the pericardium from the subxiphoid approach. Thus, it is contemplated that the longitudinal length 102, 202 of each respective catheter 100, 200 can range from about 20 cm to about 50 cm.

In exemplary aspects, the first and second catheters 100, 200 can be introduced into the pericardial space over a guide wire 300 (step 2200). The catheters 100, 200 can then be directed to opposite sides of the target pericardial reflection using standard over-the-wire steering techniques and/or fluoroscopic guidance (step 2300). When the distal ends 110, 210 of the catheters 100, 200 respectively are within close proximity, the magnet assemblies 120, 130 of the catheters will be drawn together magnetically, magnetically coupling the distal ends 110, 210 of the first and second catheters 100, 200 together (step 2400). Under conditions where there is a thin intervening tissue membrane, it is contemplated that the distal ends 110, 210 of the catheters 100, 200 can "sandwich" the membrane orthogonally to the primary lumens 116, 216, of the two catheters 100, 200. It is further contemplated that the magnetic field created by the magnet assemblies 120, 220 of the catheters 100, 200 can align the primary lumen 116 of the first catheter 100 with the corresponding primary lumen 216 of the second catheter 200, thereby facilitating longitudinal continuity. It is still further contemplated that the strength of the magnet assemblies 120, 220 and the size and flexibility of the catheters 100, 200 can allow the distal ends 110, 210 of the catheters 100, 200 to align when in close proximity.

Figure 26:
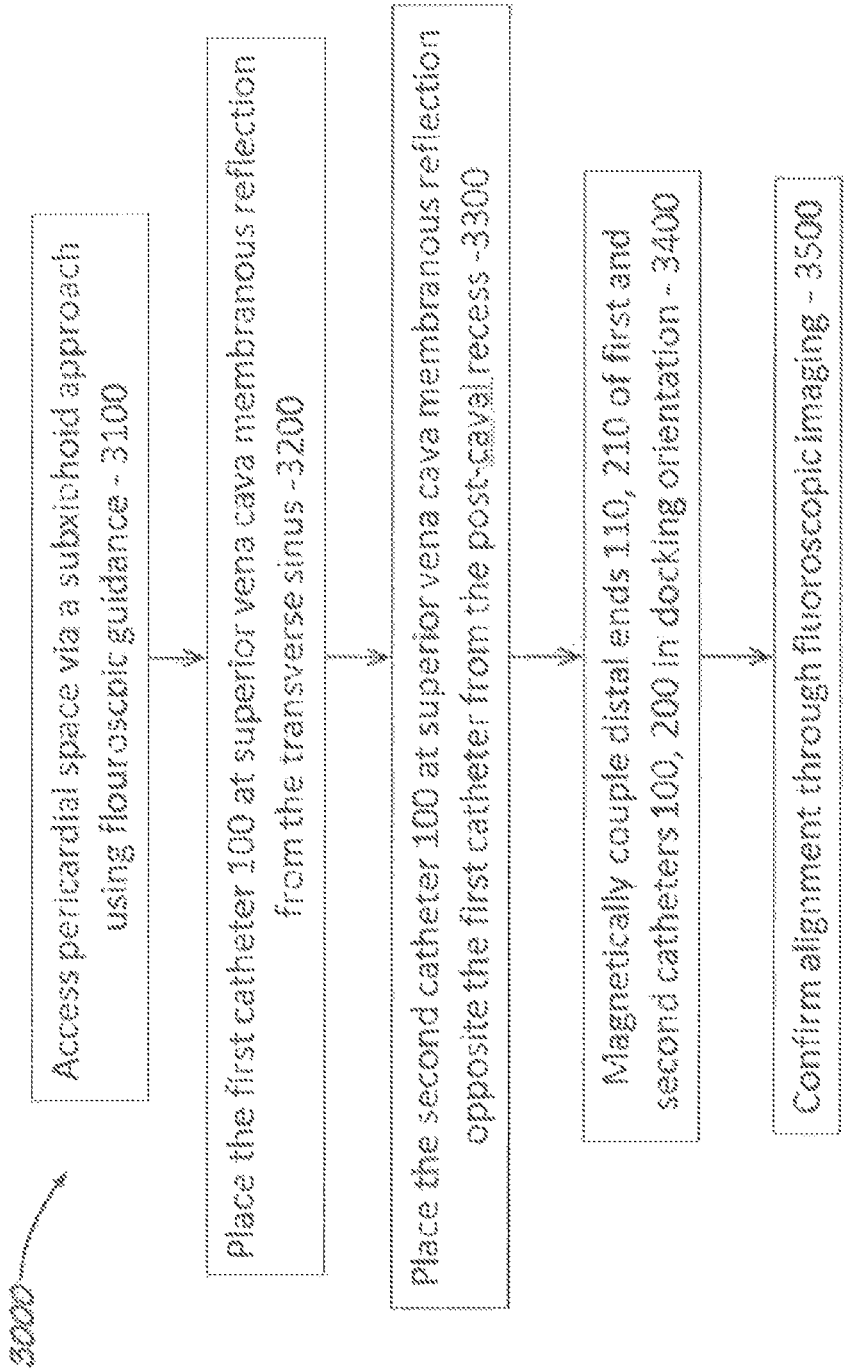
FIG. 26 is a depiction of a process to position a percutaneous catheter system according to an aspect.

Using fluoroscopic guidance, the operator can position the two complementary catheters 100, 200 on opposite sides of a target pericardial reflection (method 3000), as shown in FIG. 26. Visualization of key pericardial and cardiac landmarks can be facilitated by varying concentrations of radiopaque contrast injected and withdrawn through the irrigation ports 119, 219 of the catheters 100, 200. The catheters 100, 200 can access the pericardial space via a subxiphoid approach (step 3100). Referring to the exemplary pericardial reflection depicted in FIG. 1, it is contemplated that the male catheter 100 (i.e., the catheter of the two in which the needle is advanced) can be placed at the membranous reflection of the superior vena cava from the transverse sinus (step 3200), while the female catheter 200 (i.e., the catheter receiving the needle) can be advanced to the same membranous reflection via the post-caval recess (step 3300). Fluoroscopic navigation can be facilitated by delivery of 5-10 cc of one or more known radio-contrast agents that are injected into the pericardial space. It is contemplated that the first and second catheters 100, 200 can have a plurality of irrigation ports/side openings 119, 219 located at their distal ends 110, 910 to permit injection and suction of fluids, including, for example and without limitation, radio-contrast agents, saline, medications, and body fluids. It is further contemplated that the membranous reflection at this location can have a thickness ranging from about 0.25 mm to about 1 mm. After the catheters 100, 200 are positioned in near proximity (e.g., within about 1-2 cm of one another), the magnet assemblies attract and align the distal ends of the catheters in a "docking" orientation (step 3400). Proper "docking" orientation can be confirmed by fluoroscopic imaging (step 3500).

In exemplary aspects, both male and female catheters 100, 200 can have a central lumen 116, 216 to accommodate a standard guide wire 300. In these aspects, it is contemplated that the standard guide wire 400 can be withdrawn once the catheters 100, 200 are positioned at a desired site and orientation. It is further contemplated that, through the use of fluoroscopic guidance, the position of the male and female catheters 100, 200 can be confirmed by injection and/or suction of one or more radio-contrast agents into or from the pericardial space. It is still further contemplated that the male catheter 100 can have a retractable puncture needle 130 that can extend and "dock" with the female catheter 200 when the two distal ends 110, 210 are aligned.

Once the catheters 100, 200 are magnetically attached and aligned, with the target membrane sandwiched in between the distal ends 110, 210 of the catheters 100, 200, the operator can advance a stylus 146 (i.e., the elongate member) of the male catheter 100 until the needle 130 punctures through the target membrane and "docks" with the female catheter 200. The operator can then advance the guide wire 300 from the male catheter 100 into the primary lumen 216 of the female catheter 200. The needle 130 can then be retracted, and the catheters 100, 200 can be withdrawn, leaving the guide wire 300 in place. It is contemplated that the previously described steps can be repeated as necessary to create a path for circumnavigating the left atrial target structures. For example, it is contemplated that the above-described method can be used to create a puncture across the pericardial reflection between the superior vena cava and the right superior pulmonary vein located at the rightward terminus of the transverse sinus and a second pericardial reflection puncture located between the inferior vena cava and the right inferior pulmonary vein traversing from the rightward aspect of the pericardial space into the oblique sinus. Following removal of the catheters 100, 200 from the body of the subject, one or more ablation catheters 20 can be delivered and positioned over the guide wire 300.

It is contemplated that the percutaneous catheter system 10 can perform the puncture methods described herein without the need for direct visualization and/or mechanically advantageous positioning, as is required for more conventional puncture techniques. Typically, the restrictions of space and geometric boundaries of the pericardial space constrain over-the-wire catheter design. However, the disclosed catheters 100, 200 of the percutaneous catheter system 10 can be flexible enough to navigate multiple turns while maintaining rotational rigidity for "steer-ability" and direct of the guide wire. Additionally, the distal ends 110, 210 of the catheters 100, 200 can be blunt and/or rounded, thereby reducing the risk of inadvertent puncture of surrounding vascular structures. With the magnetic "docking" capabilities of the catheters 100, 200 through their respective magnetic assemblies 120, 220 it is contemplated that the needle 130 can be deployed when the target membrane is the only structure in jeopardy; otherwise, the needle 130 will be housed within a lumen 116 of the catheter system 10 such that there is no risk of inadvertent puncture. While the exemplary aspects of the percutaneous catheter system 10 have been disclosed in relation to first catheter 100 as being the male catheter, and the second catheter 200 being the female catheter, either assignments can differ based upon which ever catheter is configured to control the advancement of the needle. For example, in an exemplary aspect, the second catheter 200 can include a need 230 with a lumen 238 and a sharp edge 234 that is longitudinally controlled along the primary lumen 216 by a stylus 246.

In additional exemplary applications, it is contemplated that the percutaneous catheter system 10 can be applied anywhere precision catheter-based puncture between two adjacent anatomic spaces (as described above) is desired. For example, it is contemplated that a dialysis fistula can be performed by advancing opposing catheters of a percutaneous catheter system 10 to a site of adjacent artery and vein to make a controlled perforation and shunt. In another exemplary application, it is contemplated that a controlled trans-cardiac puncture can be performed across the atrial wall into the pericardial space of a subject to accomplish epicardial pacemaker lead implantation. Where a transvascular puncture site is remote, it is contemplated that other biosensor and/or stimulator lead placement could be performed using the disclosed percutaneous catheter system 10. In still further exemplary aspects, it is contemplated that the percutaneous catheter system 10 can be used for shunt placement between internal cavities, such as the plural space and parental space, for chronic plural effusions, or for creating a fistula between the bladder and a drain. It is further contemplated that the disclosed percutaneous catheter system 10 can be modified as necessary to permit usage of the catheter system in percutaneous procedures where special and anatomic restrictions do not facilitate precise puncture of a tissue structure and/or guide-wire manipulation.

Ablation Catheter

With reference to FIGS. 27-34, described herein is an ablation catheter 20 for ablating a selected tissue region within the body of a subject. In exemplary aspects, the ablation catheter 20 is an over-the-wire multi-electrode ablation catheter 20 that can create a linear circumferential ablation lesion using one or more of radiofrequency (RF) energy, irreversible electroporation (IE) impulses, and other hybrid electro cautery techniques. The ablation catheter 20 is designed to apply high-voltage, ultra-short direct current pulses to tissue that causes tissue injury, cell death, and in some instances, only cell function disruption.

However, it is contemplated that other ablative techniques such as cooling, microwave, ultrasound, light, and/or chemical ablation techniques could also be used as alternative and/or as adjuvant to the ablation approaches described herein. For example, aspects of the ablation catheter 20 can apply HVUS-DCI, RF, cryoablation, electroporation, microwave, laser, biologics, radiation, and small molecule chemicals. These impulses produce brief but extremely strong electric fields within the tissue leading to irreversible electroporation (IE), cell death, and injury. However, in an aspect, the total energy applied is relatively low averaging (estimated range 0.025 J to 45 J per pulse).

In additional exemplary aspects, the ablation catheter 20 can be used in conjunction with the percutaneous catheter system 10 described above. In these aspects, the percutaneous catheter system 10 can be used to place a guide wire 300 within the heart of a subject, and the ablation catheter 20 can be advanced within the heart over the guide wire. Following placement of the ablation catheter 20, ablative energy can be selectively applied within the heart of the subject. In exemplary aspects, the entire ablation procedure can be performed without administration of anesthesia.

In one aspect, as illustrated in FIGS. 27-32, the ablation catheter 20 comprises a flexible elongate shaft 500 having a longitudinal axis 502, a longitudinal length 504, a proximal portion 506, a central portion 508, and a distal portion 510. In this aspect, the elongate shaft 500 can define a primary lumen 512. In this aspect, it is contemplated that the primary lumen 512 can be configured to receive the guide wire 300. While the ablation catheter 20 can be comprised of many different materials, the material should flexible. In exemplary aspects, the ablation catheter 20 can be highly flexible such that, upon deployment, the flexible elongate shaft 500 of the catheter 20 can conform to the natural contours of the anatomy. In these aspects, the flexibility of the ablation catheter 20 can facilitate positioning of electrodes 530 around the outside of asymmetric and/or complex contours.

In another aspect, the ablation catheter 20 further comprises a plurality of electrodes 530 spaced along the longitudinal length 504 of the central portion 508 of the flexible elongate shaft 500. In this aspect, it is contemplated that the plurality of electrodes 530 can be integrally formed with the elongate shaft 500. Each of the electrodes 530 is configured to be connected to a signal source through an independent wire 518 (shown in FIG. 28) that is connected by pins 519 to the signal source. The electrodes 530 are configured to apply a signal to the targeted area to perform an ablation. Individual electrodes 530 can be assigned polarity and function in real time to optimize direction of current vectors during ablation. In an aspect, the electrodes 530 can be capable of monitoring and/or delivering RF energy, electroporation impulses, and programmed cardiac pacing and/or neuro-stimulus. Unlike other known ablation catheters, the electrodes 530 of the described ablation catheter 20 also can have the capability of delivering extended bipolar high voltage, ultra-short impulses.

In an aspect, in addition to being configured to apply a signal, the electrodes 530 are configured to be capable to selectively record signals. In this aspect, the signals can be described by an impulse strength, a duration, a duty cycle, and a timing. When the electrode 530 is configured to record the signals, the electrode 530 can record the above described characteristics of the signal(s) applied. The electrode 530 can capture this information, and send it to a console, described in more detail below. In an aspect, an electrode 530 that is not applying a signal can act as a recording electrode 530. In another aspect, the electrodes 530 of the ablation catheter 20 can be configured to act as a recording electrode and signal delivering electrode 530 at the same time.

In another aspect, the electrodes 530 can be configured to monitor the vital signals of the subject. For example, the electrodes 530 can receive the electronic signals produce by the subject's heart to which the electrode 530 is in contact. In an aspect, the electrode 530 can act like an EKG. In another aspect, the electrode 530 can monitor the atrial pacing (including the atria refractory period), the ventricular pacing (including the ventricular refractory period), the cycle length, the QT interval, and the QRS interval of the subject's heart. The information can be passed along to other components discussed in more detail below.

In exemplary aspects, the plurality of electrodes 530 can be spaced to provide adequate coverage for creating a contiguous linear ablation lesion 40. In these aspects, it is contemplated that the ratio of the spacing 532 between consecutive electrodes 530 to the longitudinal length of each electrode can be less than about 3:1 and, more preferably, less than about 2:1. In additional exemplary aspects, it is contemplated that the plurality of electrodes 530 can comprise between about 20 to about 40 independent electrodes 530. In an example, the ablation catheter 200 can have 30 independent electrodes (e.g., FIG. 34). In further exemplary aspects, it is contemplated that the plurality of electrodes 530 can be spaced along a sufficient length of the elongate shaft 500 (e.g., ranging from about 15 cm to about 30 cm) to create a circumscribing lesion 30 around a left atrial target and pulmonary veins. It is contemplated that the plurality of electrodes 530 can be positioned centrally along the longitudinal length 504 of the ablation catheter 20 so that the proximal portion 504 and distal portion 510 of the elongate shaft 500 are of sufficient length such that at least a portion of the proximal portion 504 and the distal portion 510 are positioned external to the body when the central portion 506 of the elongate shaft 500 (including the plurality of electrodes 530) is deployed around the left atrial target structures. It is contemplated that the ratio between the longitudinal length of the proximal portion 506 to the longitudinal length of the central portion 508 and the ratio between the longitudinal length of the distal portion 510 and the longitudinal length of the central portion 508 can each range from about 1.5:1 to about 2:1. It is further contemplated that the proximal portion 506 and the distal portion 510 of the elongate shaft 500 can each have a longitudinal length ranging from about 40 cm to about 60 cm.

In exemplary aspects, the flexible elongate shaft 500 can be configured for selective positioning within the body of the subject such that the central portion 508 of the elongate shaft 500 at least partially surrounds the selected tissue region (shown in FIGS. 33-34) and the proximal 506 and distal portions 510 of the elongate shaft 500 are positioned external to the body of the subject. In these aspects, it is contemplated that, upon positioning of the elongate shaft 500 such that the central portion 508 of the elongate shaft 500 at least partially surrounds the selected tissue region, each electrode 530 of the plurality of electrodes 530 is configured for selective, independent activation to apply ablative energy to the selected tissue region.

Optionally, in one aspect, the flexible elongate shaft 500 can further comprise one or more secondary lumens 514 defined by the flexible elongate shaft 500 and/or positioned within the primary lumen 512. In an aspect, at least one secondary lumen 514 of the one or more secondary lumens 514 or the primary lumen 512 of the flexible elongate shaft 500 can be configured to receive the guide wire 300. In such an aspect, the other lumen 512, 514 that are not for use with the guide wire 300 can be configured to receive a flexible stylus and/or other mechanical support. Further, such lumens can be configured to carry and/or deliver a cooling fluid, an irrigation fluid, small molecules, peptides, and/or DNA/RNA to improve ablation characteristics. It is further contemplated that the elongate shaft 500 can be configured for deployment within the body of the subject over the guide wire 300. However, it is contemplated that the ablation catheter 20 can optionally be deployed within the body of a subject in a manual fashion (without a guide wire).

Figure 30:
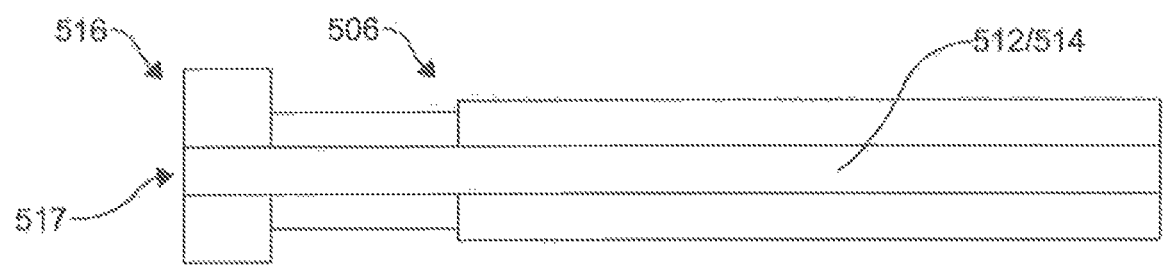
FIG. 30 is a schematic cross-sectional view of a proximal end of an ablation catheter according to an aspect.
Figure 31:
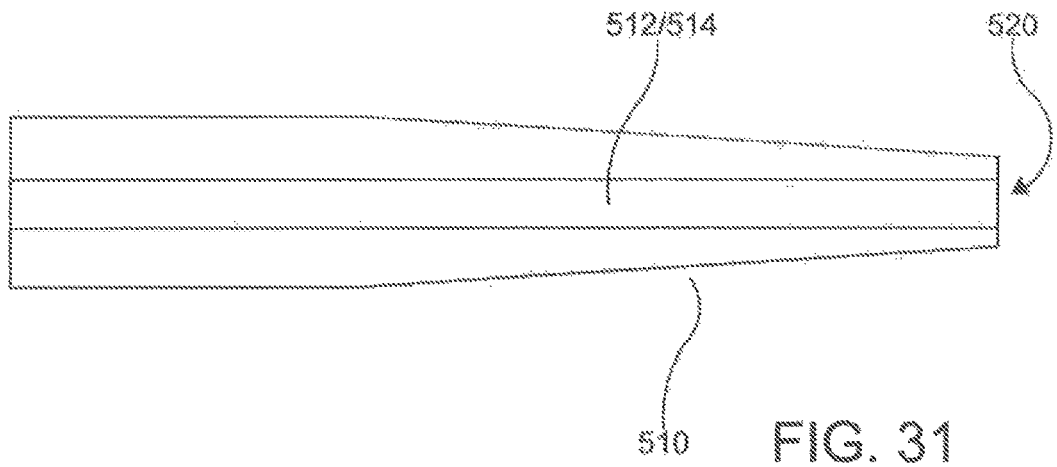
FIG. 31 is a schematic cross-sectional view of a distal end of an ablation catheter according to an aspect.

In an aspect, the proximal end 506 of the catheter 20 can include a luer lock 516 and opening 518 to receive a guidewire 300 in the primary lumen 512 or secondary lumen 514, as shown in FIG. 30. The distal end 510 can include an opening 520 that continues to the secondary lumen 514, allowing a guidewire 300 to exit, as shown in FIG. 31. Further, the distal end 510 can have a tapered shape as well.

Figure 27:
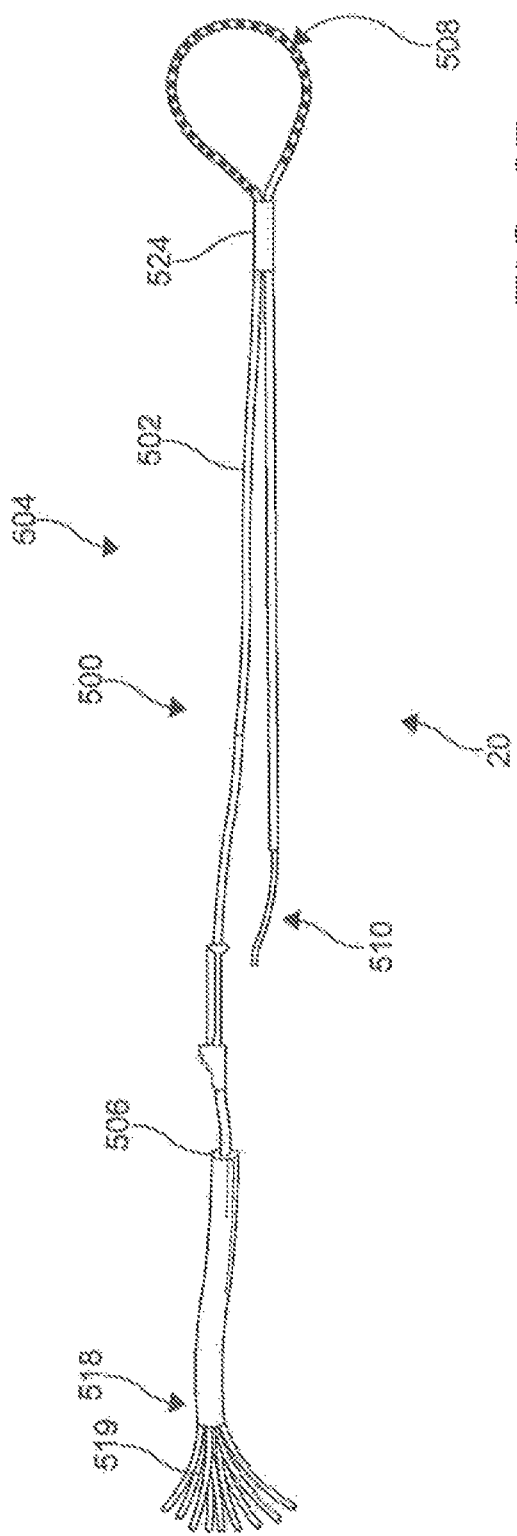
FIG. 27 depicts an exemplary ablation catheter according to an aspect.
Figure 28:
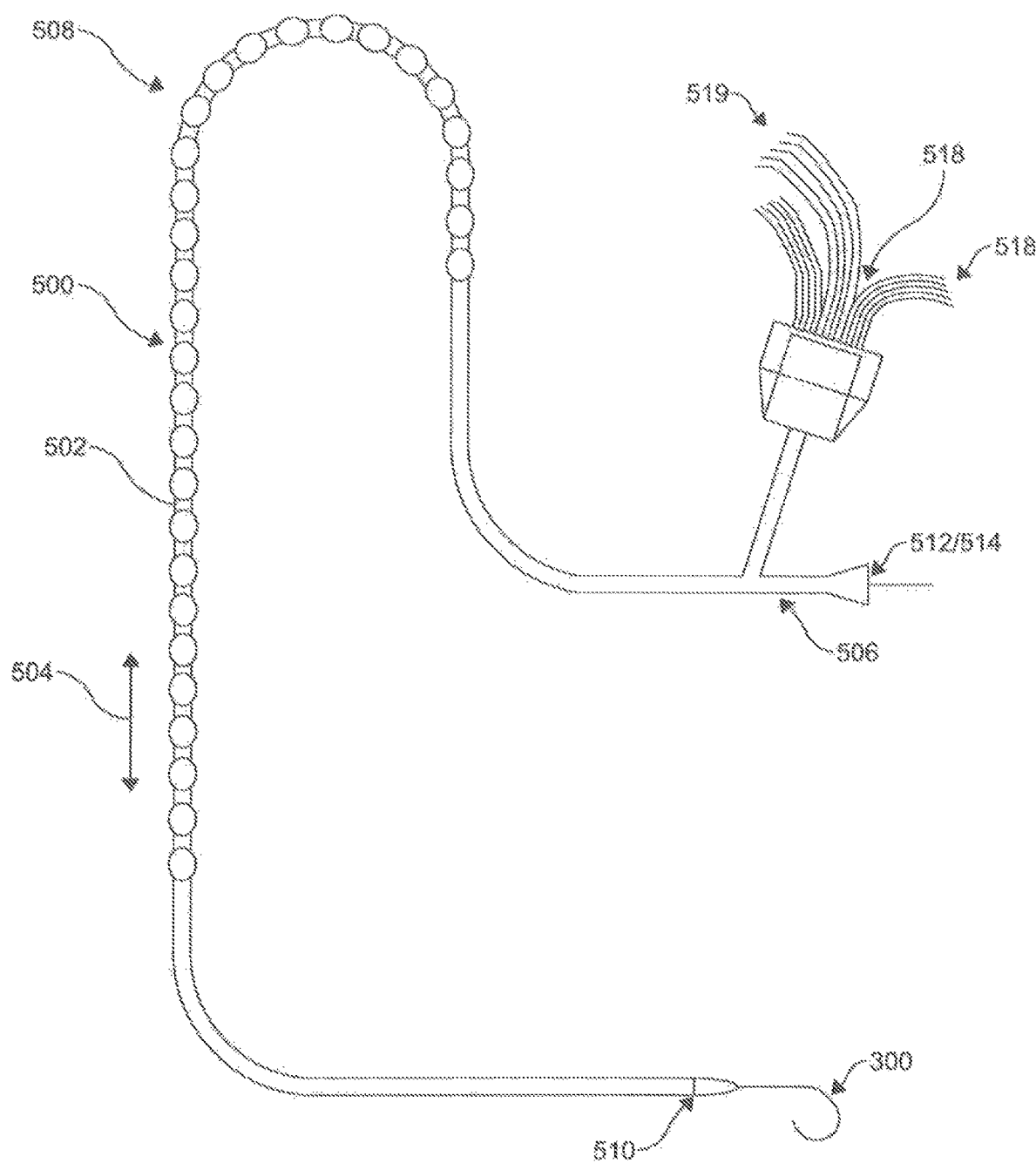
FIG. 28 is a schematic representation of an ablation catheter according to an aspect.
Figure 29:
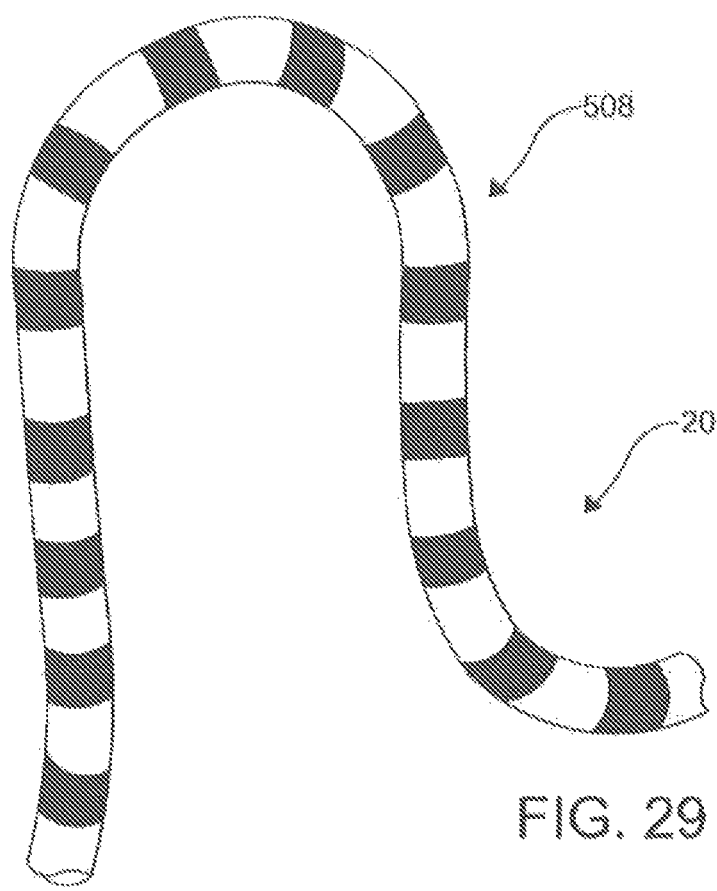
FIG. 29 is a partial close-up view of a central portion the ablation catheter of FIG. 27.
Figure 32:
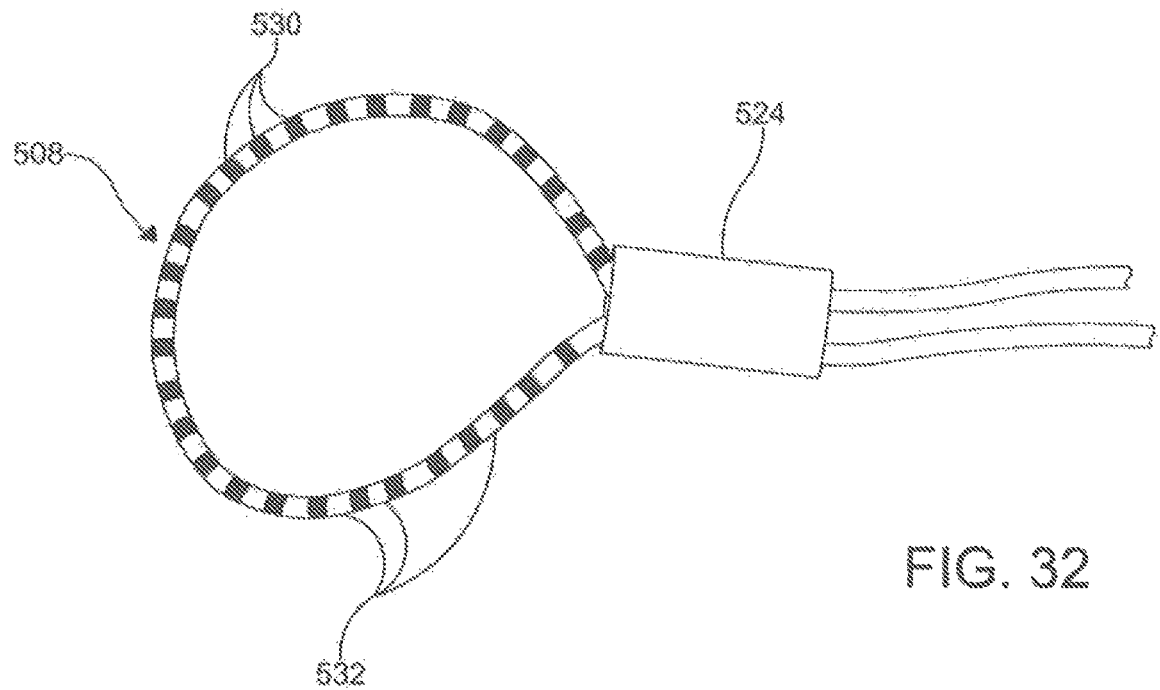
FIG. 32 is a partial close-up view of the central portion of the ablation catheter of FIG. 27.
Figure 33:
FIG. 33 depicts the positioning of an ablation catheter during an exemplary ablation procedure as described herein.
Figure 34:
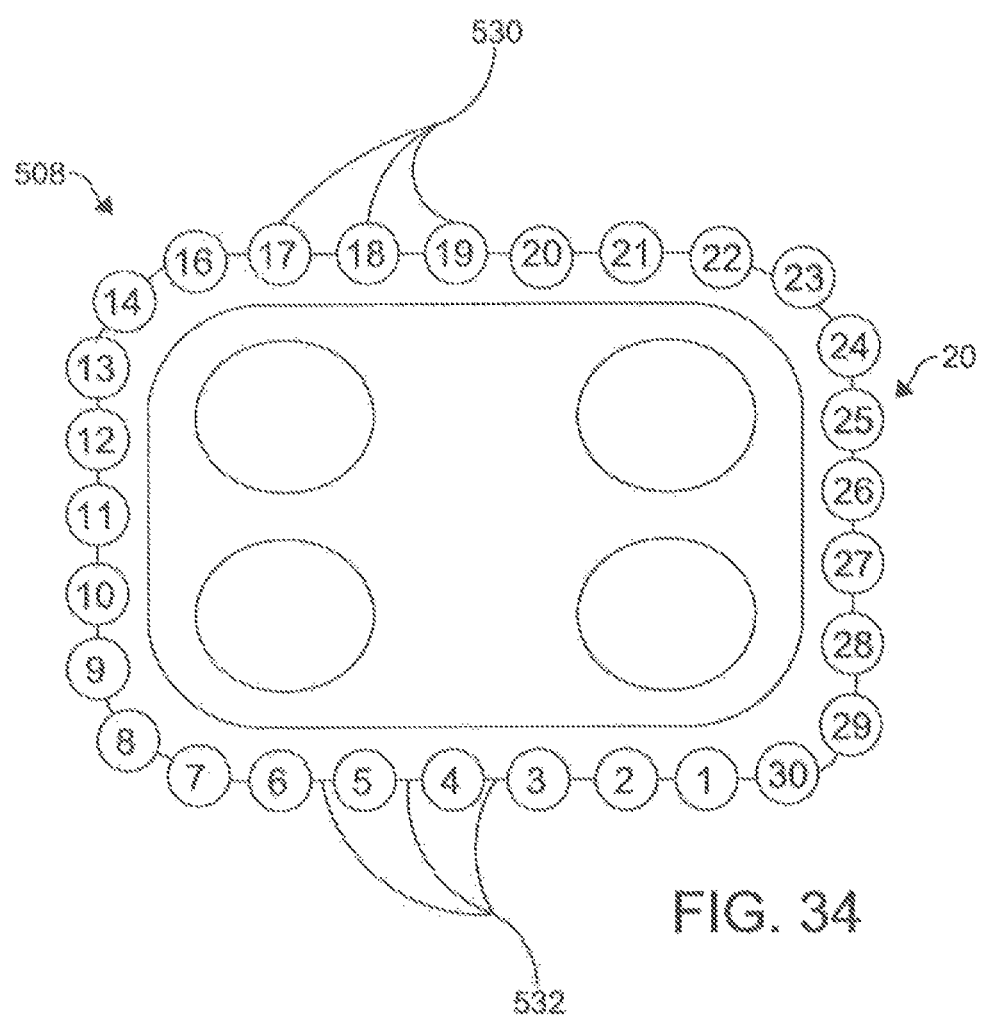
FIG. 34 is a schematic representation of an ablation catheter positioned around the heart according to an aspect.

In an aspect, the ablation catheter 20 can include a catheter noose 524, as shown in FIGS. 27 and 32. The catheter noose 524 is configured to apply tension to the elongated body 500 of the catheter 20 when the catheter 20 is positioned around the targeted sight. In an aspect, and discussed in further details below, the central portion 508 of the catheter 20 is positioned around the targeted area within the body, with the proximal 506 and distal 510 ends positioned outside of the body. The catheter noose 524 is then used to tighten the loop formed by the center portion 508 of the catheter 20 around the targeted area. In an aspect, the catheter noose 524 can include two lumens (not shown). The first lumen can be configured to receive the proximal end 506 of the catheter 20. The second lumen can be configured to receive the distal end 510 of the catheter 20 after the catheter 20, and more specifically the central portion 508, has been positioned around the targeted area within the body and the distal end 510 and proximal end 506 are positioned outside the body. The catheter noose 524 can then be advanced along the proximal and distal portions 506, 510 until the central portion 508 is fully secured, as shown in FIGS. 33-34.

Figure 35:
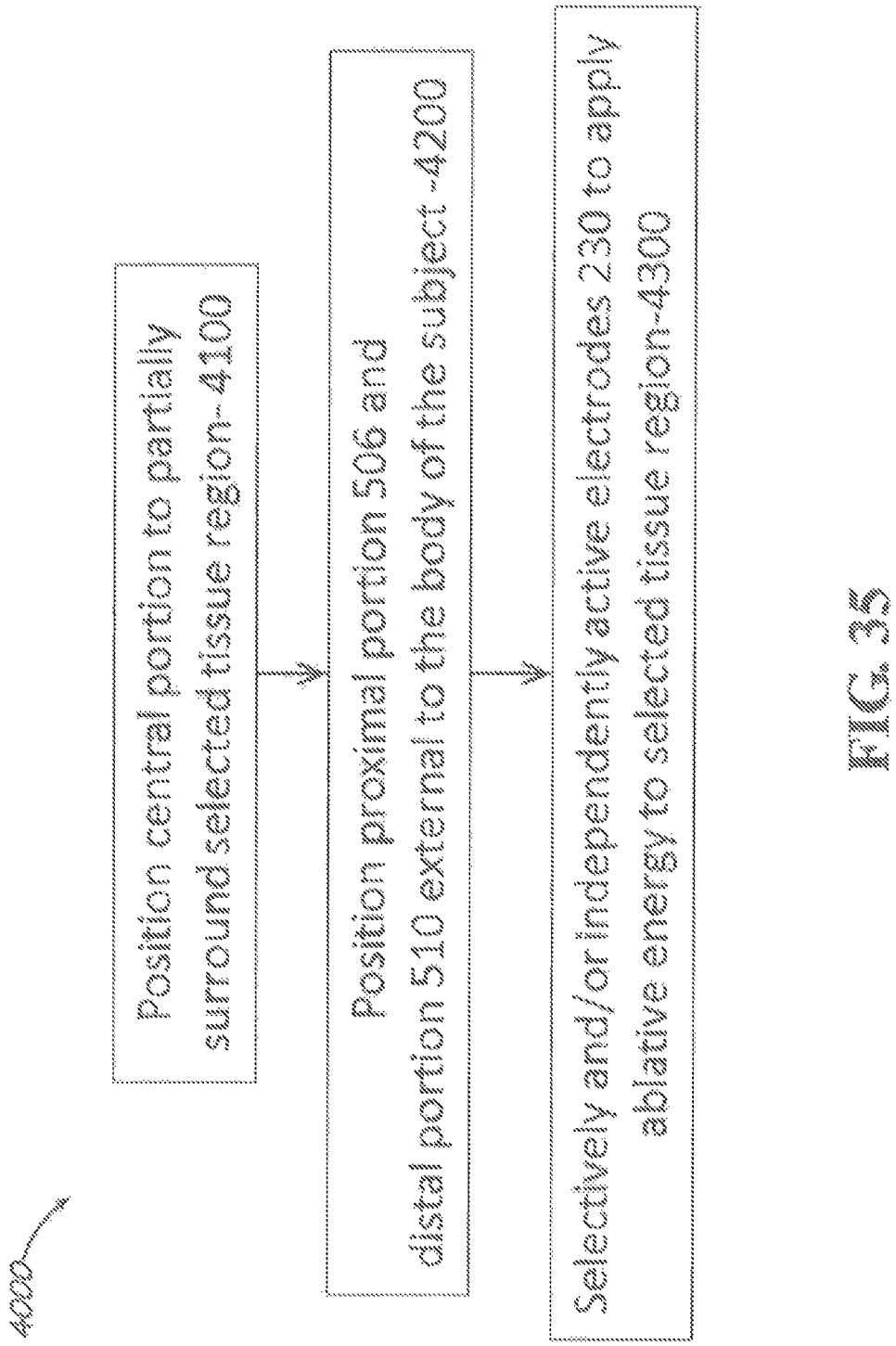
FIG. 35 is a depiction of a process to position and use an ablation catheter according to an aspect.

In use, the ablation catheter 20 can be employed in a method for ablating a selected tissue region within the body of a subject. In one aspect, the method for ablating the selected tissue region (4000), as shown in FIG. 35, can comprise selectively positioning the flexible elongate shaft of the ablation catheter within the body of the subject such that the central portion of the elongate shaft at least partially surrounds the selected tissue region (step 4100). In this aspect, the proximal portion 506 and the distal portion 510 of the elongate shaft 500 of the ablation catheter 20 can optionally be positioned external to the body of the subject (step 4200). In another aspect, the method for ablating the selected tissue region can comprise selectively, independently activating each electrode 530 of the plurality of electrodes 530 of the ablation catheter 20 to apply ablative energy to the selected tissue region (step 4300).

Figure 37:
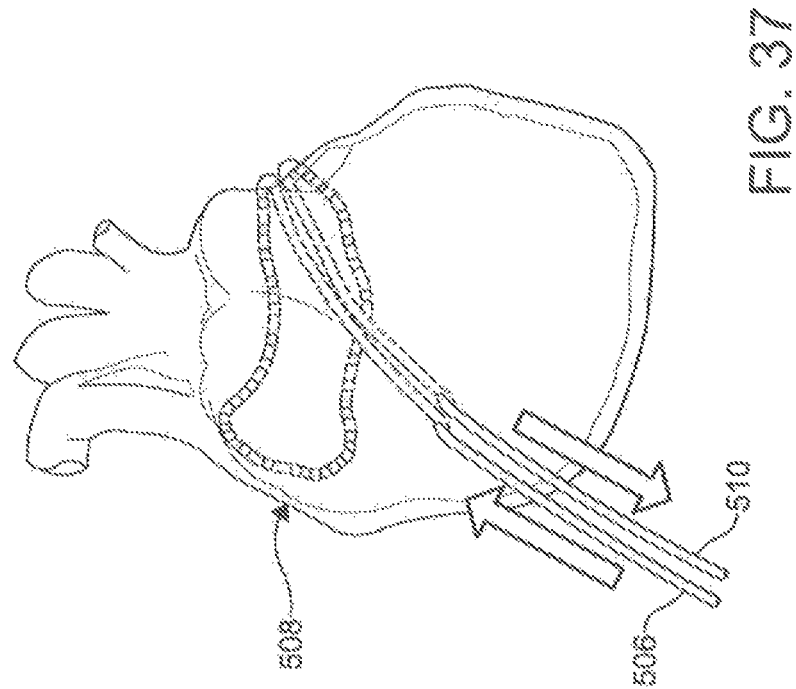
FIGS. 36-38 are illustrations of the placement and use of an ablation catheter according to an aspect.
Figure 36:
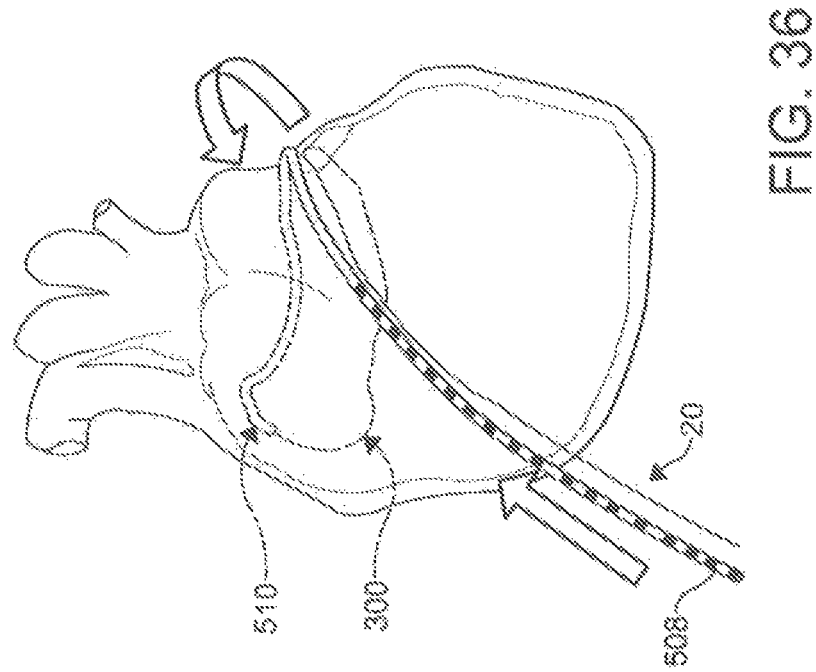
Figure 38:
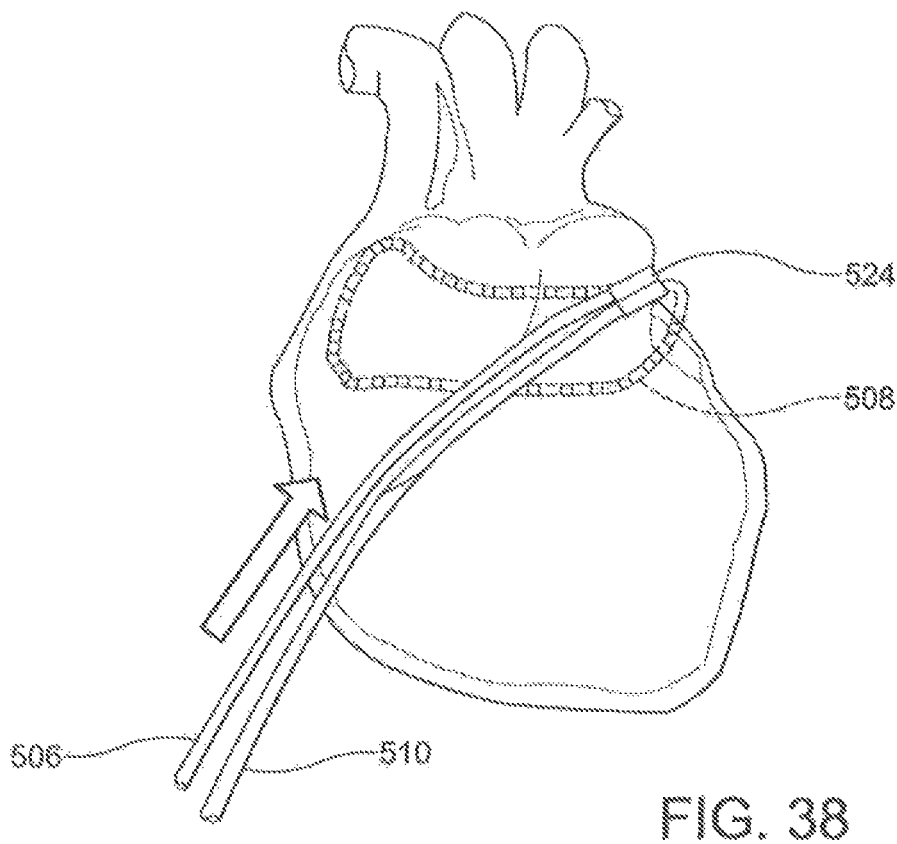
Figure 39:
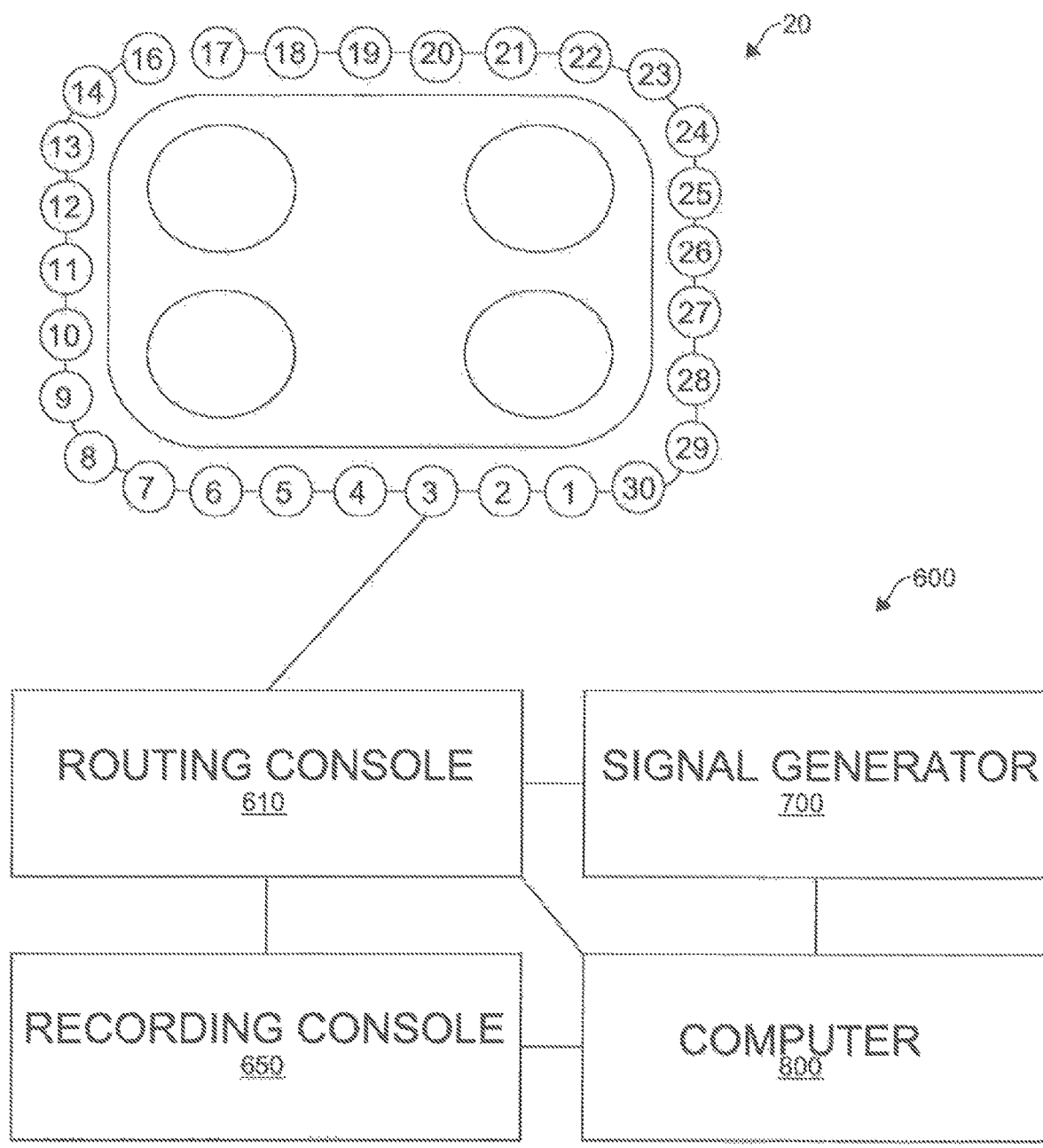
FIG. 39 is a block diagram of an exemplary ablation catheter system according to an aspect.

In an exemplary aspect of the method 4000 described above, the distal end 510 of the catheter 20 can be advanced along the guidewire 300 to be positioned around the left atrial target structures, with the distal end 510 being deployed to cross the pericardial reflection into the transverse sinus and through until the central portion 508 is positioned correctly (step 4100), as shown in FIGS. 36-37. The proximal portion 506 and distal portion 510 can be placed outside of body (step 4200), as shown in FIG. 37. Once in place, the catheter noose 524 can be advanced to cinch the loop, as shown in FIG. 38. In cases where the circumference is less than the length 504 of the catheter 20 along the central portion 508 (i.e., the multi-electrode 530 array), excess proximal electrodes 530 are deactivated and pulled proximally into the catheter noose 524 before applying ablative energy (step 4300). If the circumference of the targeted area is greater than the length 504 along the central portion 508, the central portion 508 will require an additional repositioning after applying the ablative energy (step 4300).

In exemplary aspects, it is contemplated that the ablation catheter 20 can be included in an ablation catheter system 600 for ablating a selected tissue region within the body of a subject, as shown in FIGS. 39-44. In an aspect, the ablation catheter system 600 can include a routing console 610, a recording console 650, a signal generator 700, and a computer 800. The routing console 610 is electrically coupled to the plurality of electrodes 530 of the ablation catheter 20. More specifically, the routing console 610 is connected to each pin 519 of each independent wire 518 from each electrode 530. The routing console 610 can carry signals from the signal generator 700 to the electrodes 530, as well as assign polarity and function in real time to optimize the direction of current vectors during ablation, discussed in more detail below.

Figure 40:
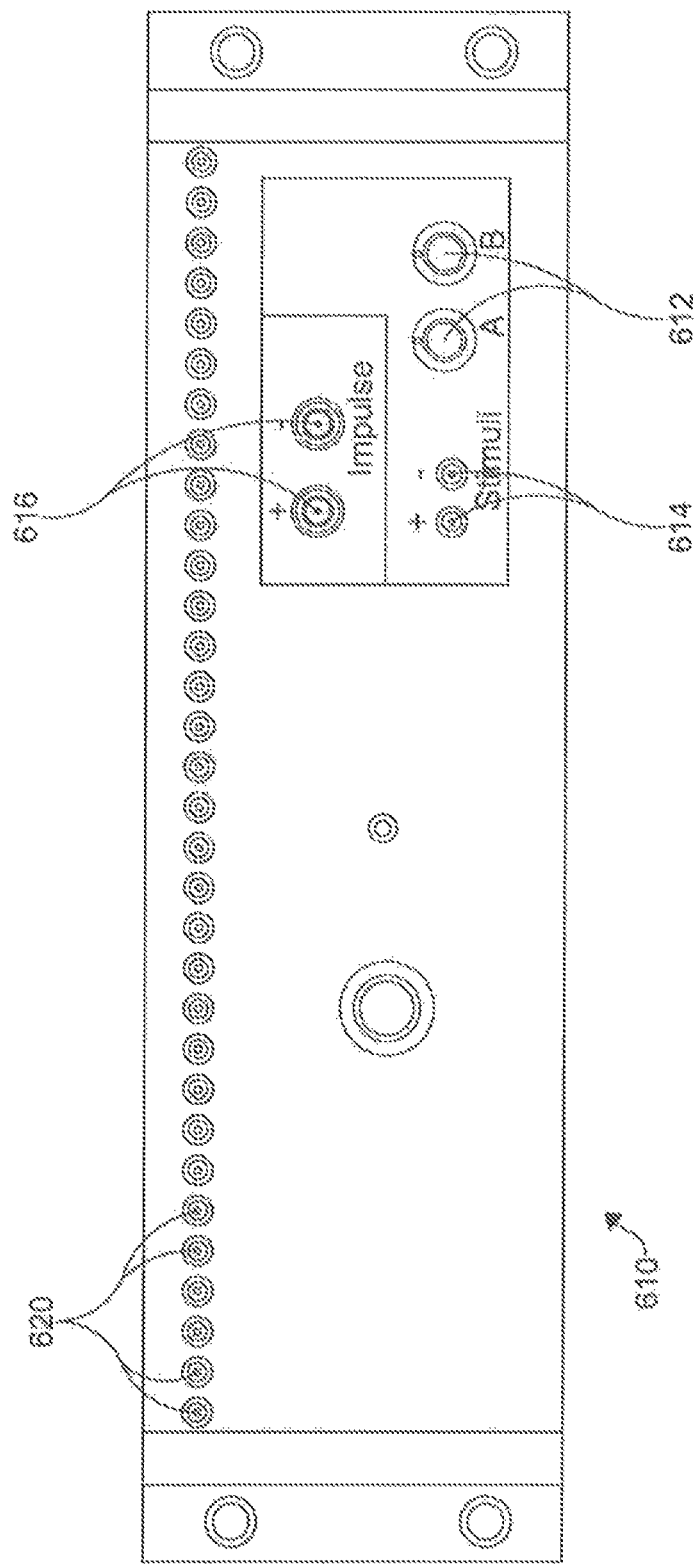
FIG. 40 is a schematic front plane view of a routing console according to an aspect.
Figure 41:
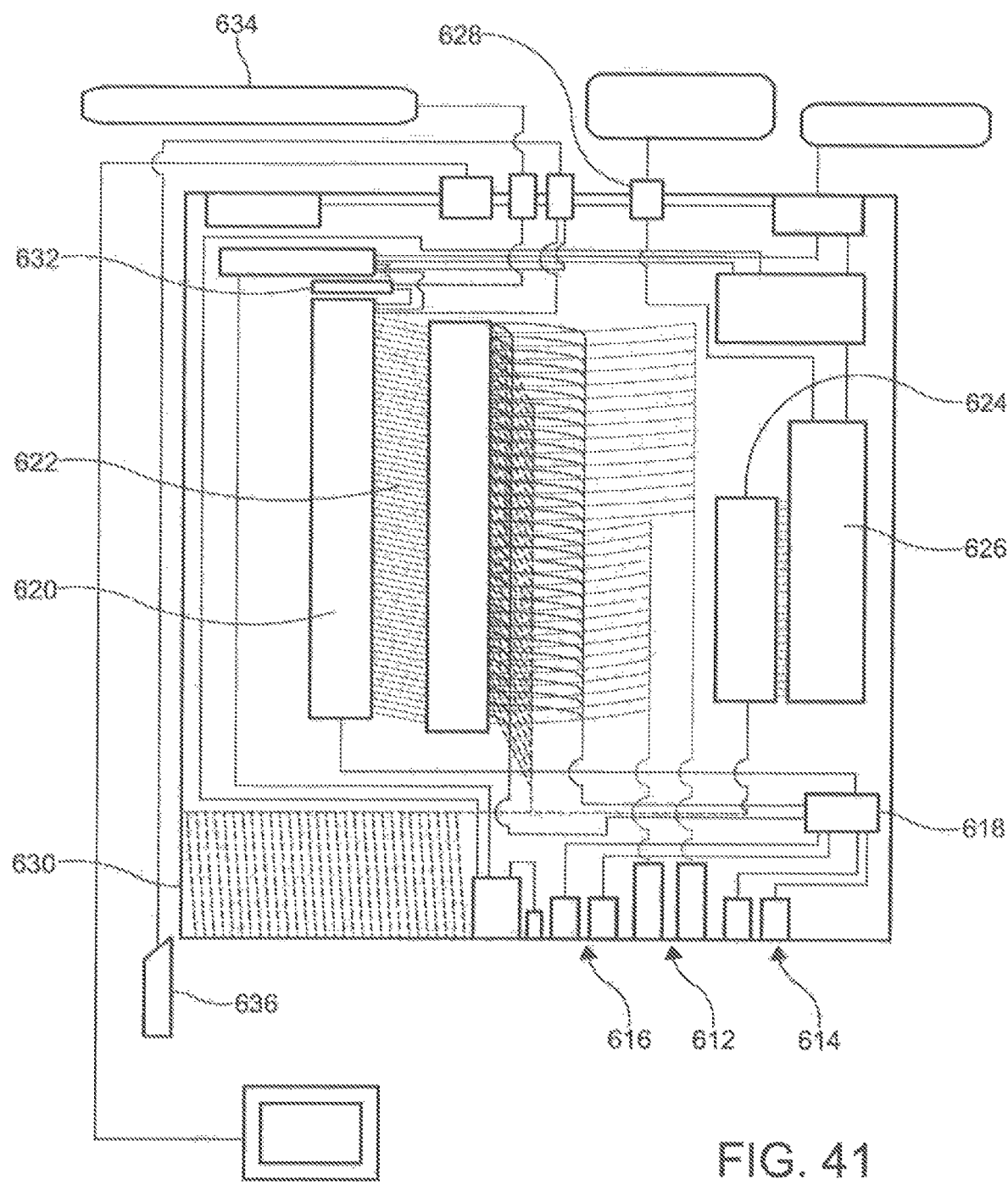
FIG. 41 is a block diagram of a routing console of FIG. 40.

As shown in FIGS. 40-41, the routing console 610 includes catheter connectors 612 to receive the pins 519 of the ablation catheter 20. An exemplary routing console 610 can include two 16 pin connecters used to accommodate thirty (30) independent electrodes 230 on the exemplary ablation catheter 200. However, the total number of catheter connectors can be adjusted to accommodate any range of electrode arrays. The routing console also includes pacing inputs 614, which can receive monitoring information from devices (EKG, etc.) used to monitor the function of the subjects' vital parts, including the heart. The routing console 610 can include signal inputs 616. The signal inputs 616 receive the signal(s) from the signal generator 700. In an aspect, the signal inputs 616 can include high voltage inputs 616. In other aspects, the signal inputs can accept RF and/or any electrical ablation energy source generated by the signal generator 700. The pacing inputs 614 and signal inputs 616 feed into the input signal relay 618, which passes along all the information and signals to the various other components of the ablation catheter system 600, including the signal generator 700, recording console 650 and computer 800, as well as other components of the routing console 610.

The input signal relay 618 is connected to logic controllers 620 and a relay bank 622. The logic controllers 620 and relay bank 622 work in tandem to send signals to a specific electrode 530 based upon the information and commands received from other components, including the signal generator 700, the computer 800, and the pacing inputs 612. The relay bank 622 can pass signal information, as well as other information, to another relay bank 624 which is connected to an I/O interface 626. The I/O interface 626 can be in communication with the signal generator 700 through a signal generator output 628. The first relay bank 622 can also pass along any information related to the signals that are being monitored by an electrode 530 to sensing outputs 630, which can be connected to the recording console 650. The routing console can also include a timing relay 632 which works with the controllers 620 to control the delivery of the signals to the electrodes 530. The timing relay 632 is connected to a synchronization trigger 634, which is in communication with the signal generator 700.

Figure 45:
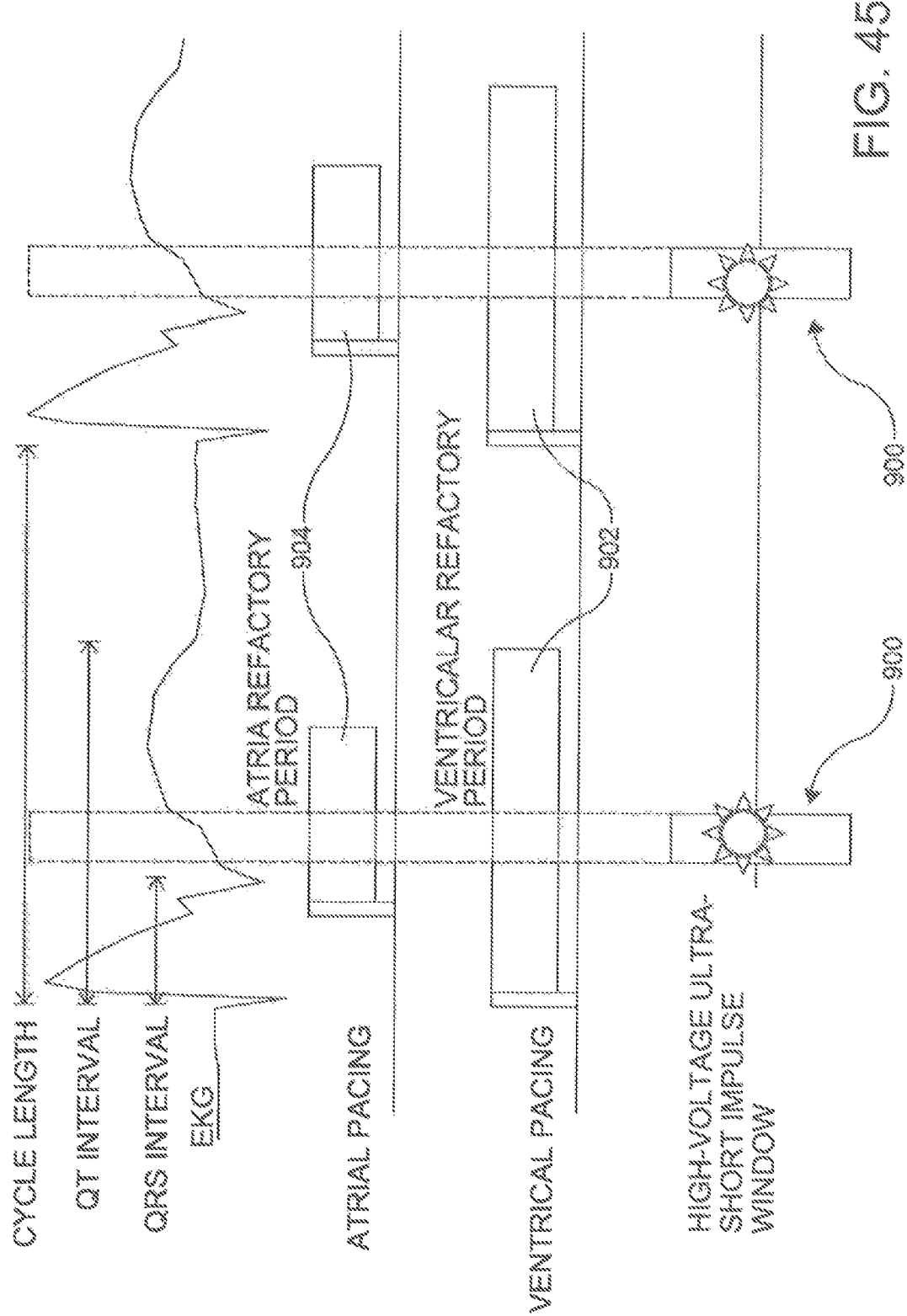
FIG. 45 is an illustration of a graphic representation of a high-voltage impulse window according to an aspect.

In an aspect, the synchronization trigger 634 ensures that when signals are sent to the electrodes 530 for ablation, the signals are applied in synchronization with the cardiac cycle, discussed in more detail below. The synchronization trigger 634 can receive monitoring information monitoring devices through the pacing inputs 614 or through electrodes 530 that are assigned to a monitoring function. The synchronization trigger 634 can monitor the EKG results, the atrial pacing (including the atria refractory period), the ventricular pacing (including the ventricular refractory period), the cycle length, the QT interval, and the QRS interval of the subject's heart to indicate when a signal should be delivered to the electrodes 530. For example, as shown in FIG. 45, the synchronization trigger 634 can determine the impulse window 900 (i.e., when to apply the signal) by identifying when the ventricular refractory period 902 and the atria refractory period 904 overlap. The synchronization trigger 634 can then alert the routing console 610 and the signal generator 700 of the window 900 to apply the signal.

31 The routing console 610 includes a fire button 636. The fire button activates the signal generator 700 to generate a signal to deliver a signal to the routing console 610. The routing console 610 will then deliver the signal to the desired electrodes 530. The computer 800 can direct the routing console 610 as to which electrodes 230 to deliver the signal.

The routing console 610 is electrically coupled to the signal generator 700. In an aspect, the signal generator 700 can comprise one or more signal generators 700. It is contemplated that each signal generator 700 of the one or more signal generators 700 can be configured to selectively generate one or more electrical signals. The signal generator 700 can create several types of signals, including, but not limited to, radio-frequency (RF), high voltage ultra-short direct current (DC) impulses (as used in electroporation), stimulus range impulses, and/or hybrid electrical impulses. In addition, the signal generator 700 can vary at least one of the impulse strength, duration, duty cycle, and timing of the signals that the signal generator 700 generates.

Figure 42:
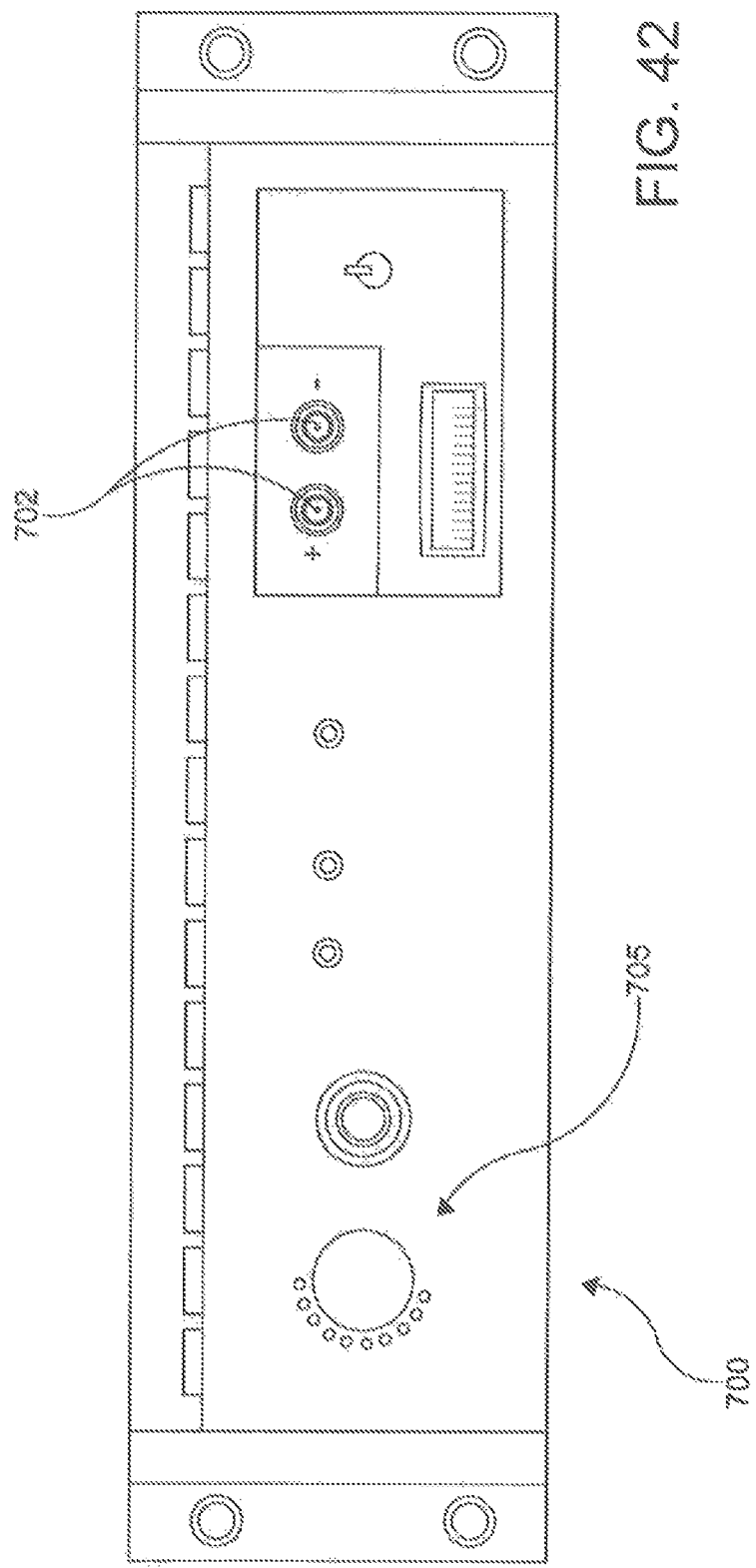
FIG. 42 is a schematic front plane view of a signal generator according to an aspect.
Figure 43:
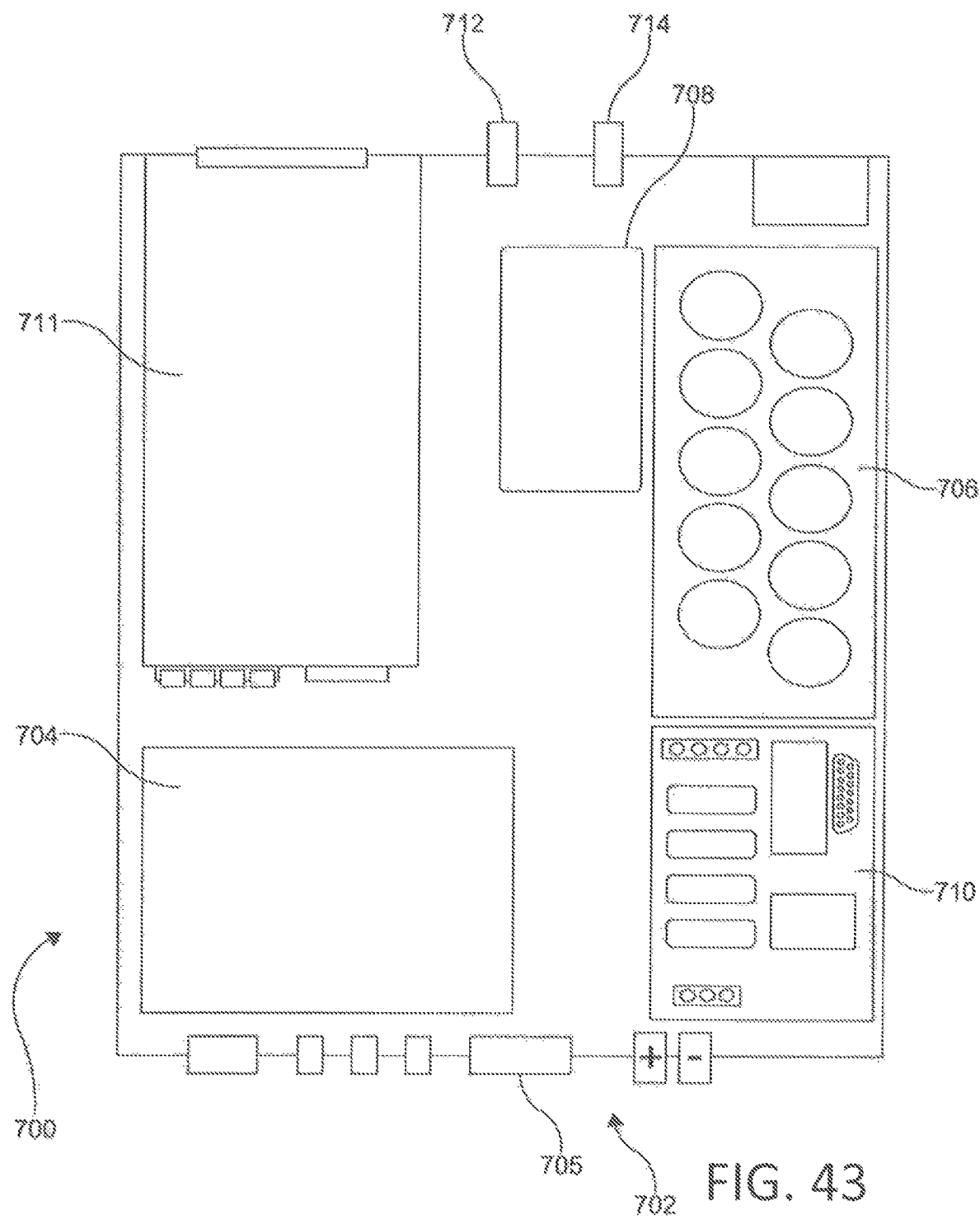
FIG. 43 is a block diagram of a signal generator of FIG. 42.

In an aspect, as illustrated in FIGS. 42-43, the signal generator 700 includes pulse/high voltage outputs 702 that are configured to connect with the pulse/high voltage inputs 616 of the routing console 610. The outputs 702 deliver the signal to the routing console 610. The signal generator 700 can include a control circuit 704 that controls the characteristics of the signal that it generates, discussed in more detail below. The control circuit 704 can also be connected to a voltage level controller 705. The pulse outputs 702 receive the signal from a capacitor 706. In an aspect, the capacitor 706 can comprise a bank of capacitors 706. A power supply 708 can provide the power needed to the capacitor(s) 706 to generate a signal. In an aspect, the capacitor 706 can pass along the signal to a transistor 710. In an aspect the transistor 708 can include an insulated-gate bi-polar transistor 710. The signal generator 700 also includes a commercially available pulse capacitor charger 711 which provides a high voltage source for the capacitor bank and a feedback control to adjust peak voltage charge.

In an aspect, the signal generator 700 can also include various inputs to reference information and commands. For example, the signal generator 700 can be connected to the computer 800 and the routing console 610 through an input/output connection 712. The input/output connection can comprise a plurality of input/output connections 712. In addition, the signal generator can be connected to the fire button through a separate input 714. Parameters/commands from the computer 800 and information from the routing console 610, including the synchronization trigger 634 and activation of the fire button 636, are received by the control circuit 704. Based upon the information received, the control circuit 704 controls the generation of the signal. For example, the control circuit 704 can control the pulse duration, the number of pulses within a burst, the burst pulse spacing, the voltage of the signal, and other signal parameters. In another aspect, the control circuit 704 can initiate the signal upon receiving a response from the fire button. In another aspect, the control circuit 704 can control when the signal is generated based upon information received from the synchronization trigger 634 in order to deliver a signal within the pulse window 900.

In an aspect, the recording console 650 can receive and record all the information that is collected by the various other components of the system 600. For example, the recording console 650 can record the pacing information that the routing console 610 receives from monitoring devices associated with the subject. In addition, the recording console 650 can receive monitoring information from the electrodes 530 monitoring the subject. In an aspect, the recording console 650 can also receive the signal information from the recording electrodes 530. In another aspect, the recording console 650 can receive other information from the signal generator 700 regarding the timing and strength of the signals generated, as well as other information. In an aspect, the recording console 650 can be a separate component from the computer 800 and routing console 610. It can be a display device that immediately displays conditions to the users of the system 600. In other aspects, the recording console 650 can be an application within the computer 800. The physical characteristics of the recording console 650 are not important, nor whether it is a separate entity from the other components of the ablation system 600.

In an aspect, the computer (shown in FIG. 44) can include ablation control software 806 that controls the overall function of the ablation system 600. The ablation control software 806 can use the other components of the system 600 to retrieve information (gathering signal information from the signal generator 700/electrodes 230, and pacing information from the routing console 610/electrodes 530) in order to initiate and maintain the ablation treatment. In other aspects, the ablation control software 806 can also control the synchronization trigger 634, or supply the synchronization trigger 634 with the needed information to apply the signal during the window 900.

In these aspects, the routing console 610 can be configured to receive the one or more electrical signals from the one or more signal generators 700. It is contemplated that the routing console 610 can be further configured to selectively activate the plurality of electrodes 530 by delivery of the one or more electrical signals from the signal generators 700. In an aspect, the routing console 610 can be configured to selectively activate at least one electrode 530 of the plurality of electrodes 530 of the ablation catheter 20 such that the at least one electrode 530 has a first polarity that is different from a polarity of at least one other electrode 530 of the plurality of electrodes 530, which, in turn, can provide means for customizing the ablation vector for each electrode 530 individually and/or delivering pacing and/or ablation impulses in quick succession.

Figure 46:
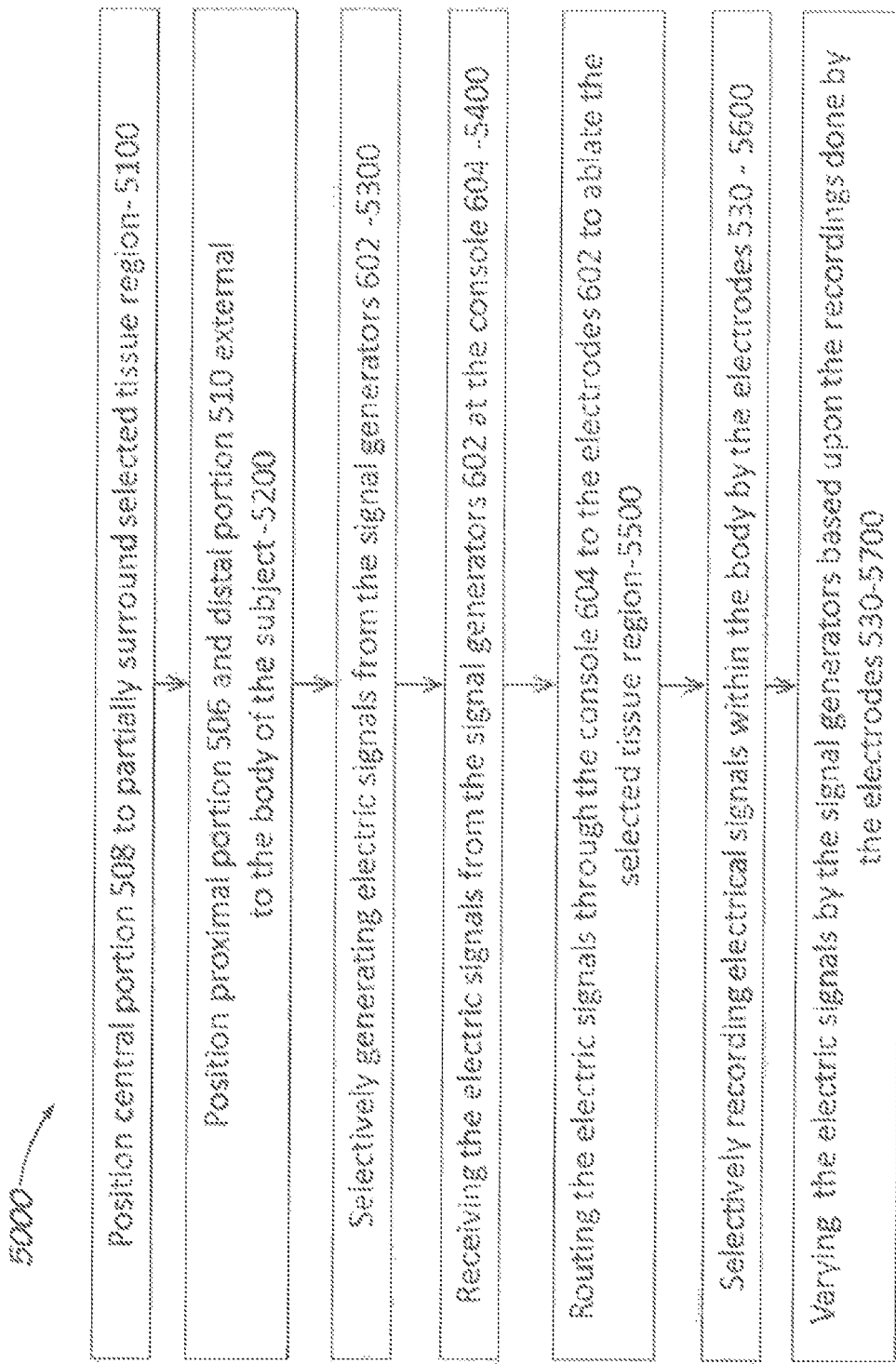
FIG. 46 is a depiction of a process to position and use an ablation catheter according to an aspect.

In exemplary aspects, the ablation catheter system 600 can be employed in a method for ablating a selected tissue region within the body of a subject 5000, as shown in FIG. 46. In one aspect, the method 5000 for ablating a selected tissue region can comprise selectively positioning the flexible elongate shaft 500 of the ablation catheter 20 within the body of the subject such that a central portion 508 of the elongate shaft 500 at least partially surrounds the selected tissue region (step 5100) and a proximal portion 506 and a distal portion 510 of the elongate shaft 500 are positioned external to the body of the subject (step 5200). In another aspect, the method for ablating the selected tissue region can comprise selectively generating one or more electrical signals using the one or more signal generators 610 (step 5300). In an additional aspect, the method for ablating the selected tissue region can comprise, through the routing console 620, receiving the one or more electrical signals from the one or more signal generators 610 (step 5400). In a further aspect, the method for ablating the selected tissue region can comprise, through the routing console 620, delivering the one or more electrical signals to the plurality of electrodes 530 of the ablation catheter 20 such that each electrode 530 of the plurality of electrodes 530 is selectively, independently activated to apply ablative energy to the selected tissue region (step 5500). In an exemplary aspect, the method for ablating the selected tissue region can further comprise, through the plurality of electrodes 530, selectively recording one or more electrical signals within the body of the subject (step 5600). In another exemplary aspect, the method for ablating the selected tissue region can further comprise, through the one or more signal generators 610, selectively varying at least one of the impulse strength, the duration, the duty cycle, and the timing of the one or more electrical signals generated by the one or more signal generators 610 based upon the one or more electrical signals recorded by the plurality of electrodes 530 (step 5700). In a further exemplary aspect, it is contemplated that the step of, through the routing console, delivering the one or more electrical signals to the plurality of electrodes 530 can comprise selectively activating at least one electrode 530 of the plurality of electrodes 530 such that the at least one electrode 530 has a first polarity that is different from a polarity of at least one other electrode of the plurality of electrodes 530, as discussed above.

In exemplary aspects, the ablation catheter 20 can be highly flexible such that, upon deployment, the flexible elongate shaft 500 of the catheter 20 can conform to the natural contours of the anatomy. In these aspects, the flexibility of the ablation catheter 20 can facilitate positioning of electrodes 530 around the outside of asymmetric and/or complex contours.

It is contemplated that the ablation catheter 20 can be configured to deliver both radio frequency (RF) and/or high intensity ultra short duration electrical impulses/irreversible electroporation (IE) to ablate adjacent tissue. RF ablation in the closed pericardial space has some important limitations. First, RF ablation can produce tissue injury through resistive heating. The lesion depth resulting from RF ablation can be limited by the energy and thermodynamics of the tissue environment. For example, a unipolar RF lesion created from the epicardium can require greater energy to create a transmural lesion than the same lesion delivered form an endocardial approach; this is because the endocardium is cooled by the blood pool and there is often a layer of epicardial fat that adds thickness. (See FIG. 47.) Using an extended bipolar electrode arrangement, it is contemplated that approximately 50% more directional penetration can be achieved (using RF techniques).

Figure 47:
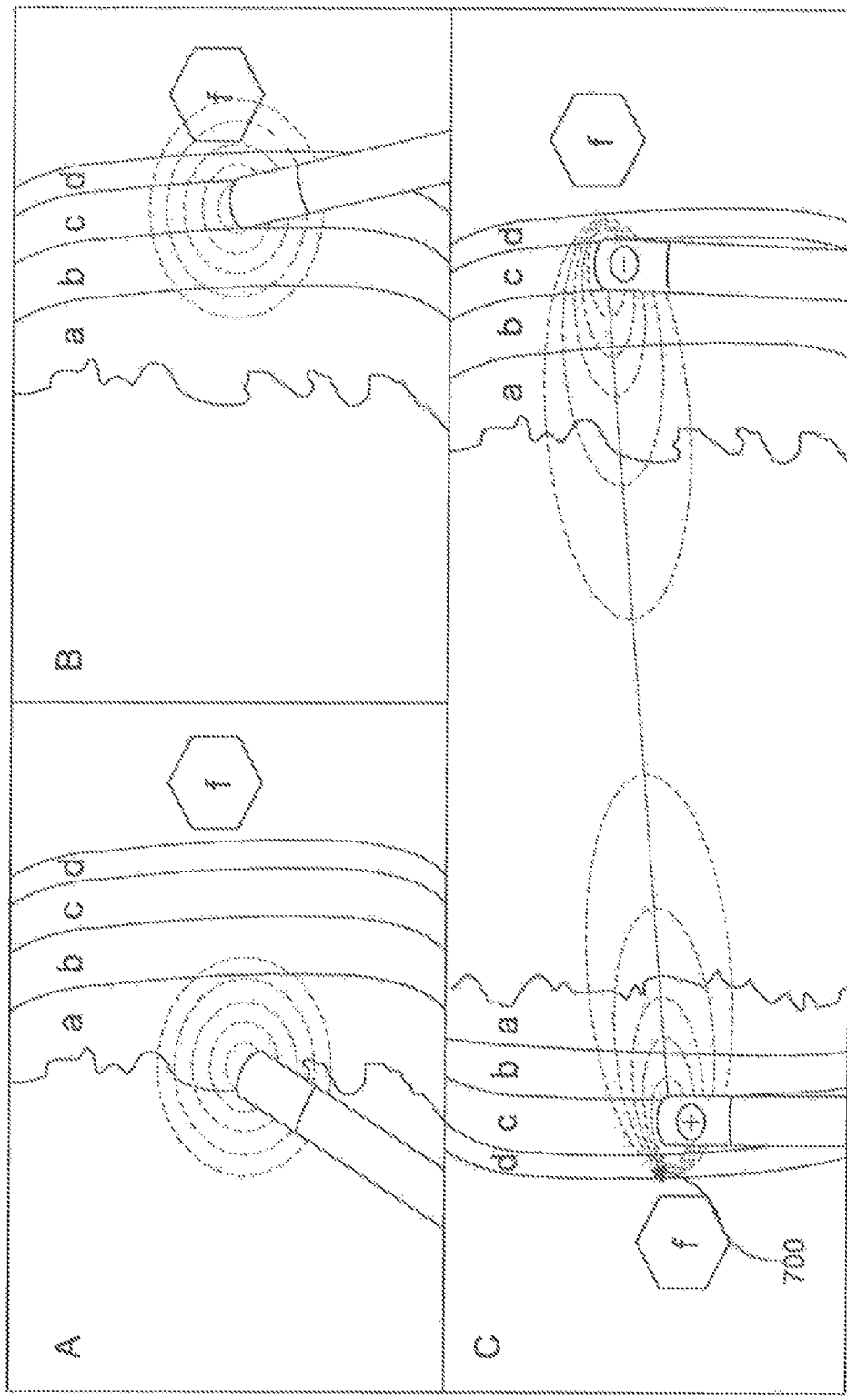
FIG. 47 are schematic representations of epicardial ablation techniques.

FIG. 47 shows the potential advantages of an extended bipolar ablation arrangement for epicardial ablation techniques. Panel (A) depicts a virtual electrode from a standard unipolar RF ablation on an endocardial surface. As shown, the field of the unipolar signal extends substantially only along the myocardium (a) and epicardial fat (b). Panel (B) shows unipolar RF ablation from an epicardial approach, with the field of the unipolar signal extends into the epicardial fat (b), pericardial space (c), and parietal pericardium (d). However, the field also extends to a bystander vulnerable structure (f). Panel (C) illustrates the distortion of the virtual electrode by using an extended bipolar orientation. As shown, the bipolar orientation leads the field to extend into the ventricular myocardium (a), epicardial fat (b), pericardial space (c), and parietal pericardium (d) without impacting the bystander vulnerable structure (f).

It is contemplated that the use of high-voltage, ultra-short impulses (irreversible elecroporation) can substantially increase the directionality of the ablation vector. In a closed pericardial space, the thermal conduction can continue to be problematic, causing undesirable collateral damage and/or accumulation of proteinaceous material on the electrodes, which can require device removal, cleaning, and/or reinsertion. However, despite these limitations, it is contemplated that RF techniques may be preferred for ablation targets that are epicardial structures, such as autonomic ganglia.

The selected polarity of each electrode 530 of the plurality of electrodes 530 can be assigned based upon the geometric orientation of each respective electrode 530 toward the ablation target. Optionally, the assignment of polarity to each respective electrode 530 can be performed in real time using the routing console 610 attached to the catheter 530 outside the body. In an aspect, the polarity assignment for each respective electrode 530 can be adjusted to tailor the intended vectors of ablation current. It another aspect, the polarity assignment can optionally be performed in connection with a remote electrode located within or external to the body. In these aspects, the vector of current between any two electrodes of the plurality of electrodes can be directed toward the intended ablation target by choosing an electrode 530 combination that optimizes the intended vector and away from bystander structures (see FIG. 47). In another aspect, the electrode combination can comprise two or more electrodes 530 of the central portion 508 of the ablation catheter 50.

Figure 48:
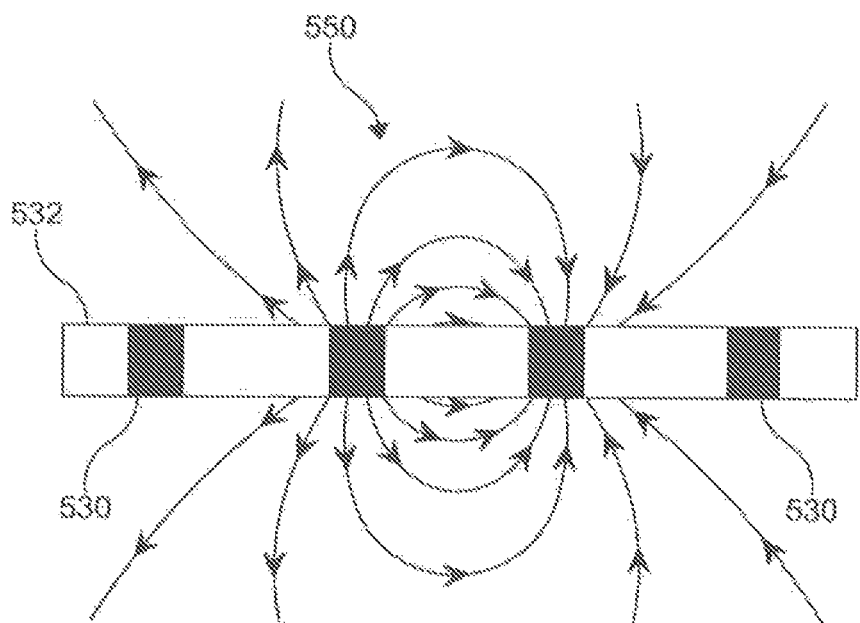
FIG. 48 is a schematic representation of an ablation catheter with electrodes according to an aspect.
Figure 49:
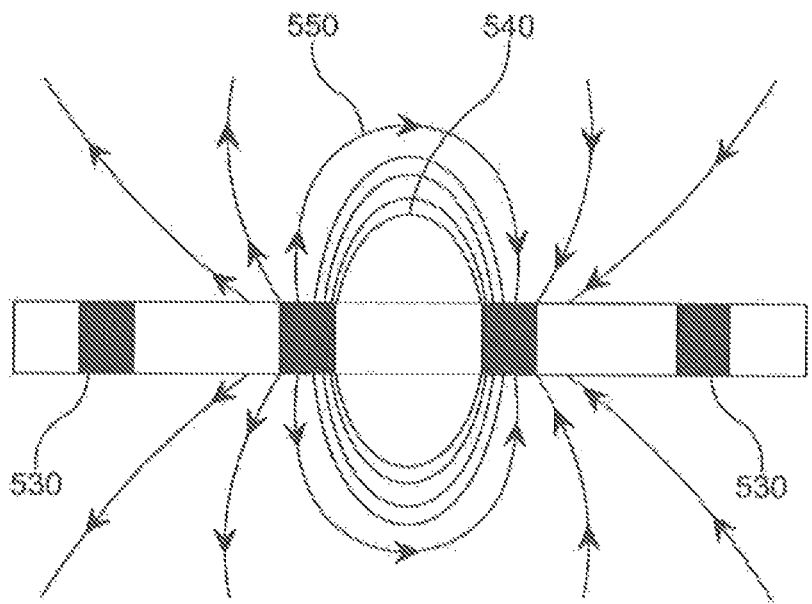
FIG. 49 is a schematic representation of an ablation catheter with electrodes and a high impedance structure according to an aspect.
Figure 50:
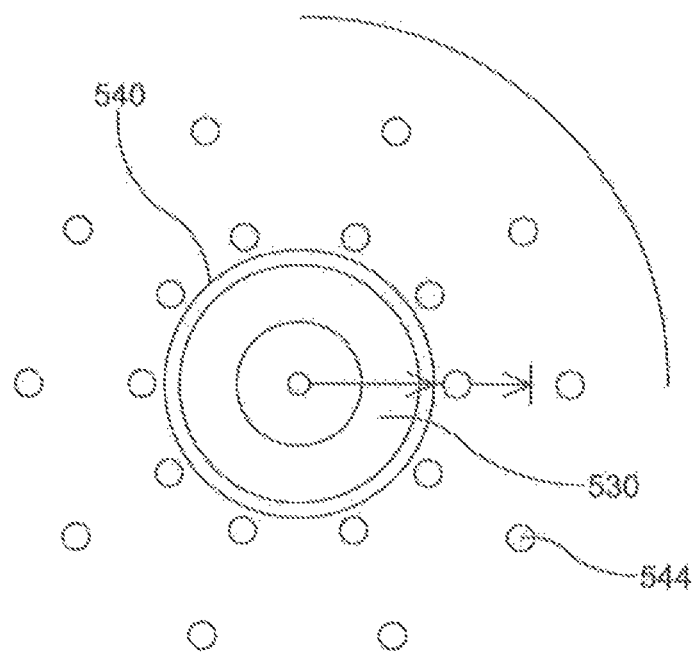
FIGS. 50-51 are schematic representations of a cross section of the ablation catheter according to an aspect.
Figure 51:
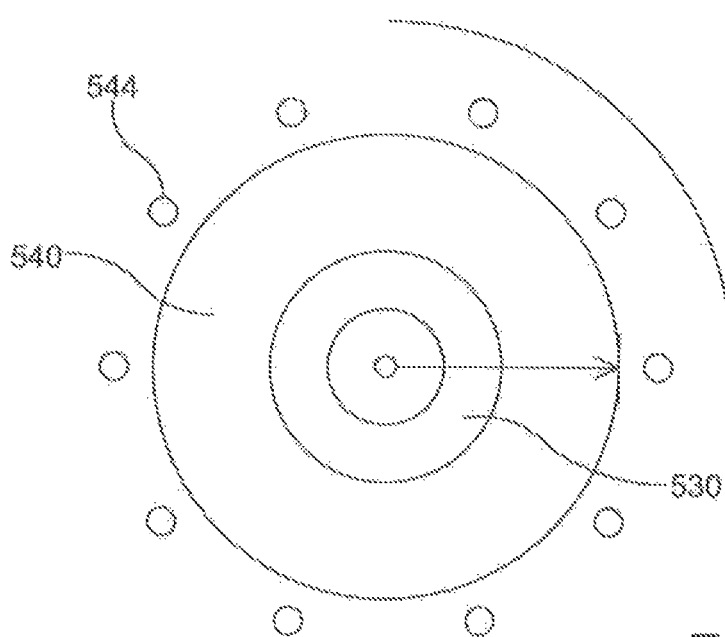

In another aspect, a high impedance structure 540 can be positioned between the electrodes 530. The high impedance structure 540 is configured to change and/or direct the current path between selected electrodes 530, as illustrated in FIGS. 48-52(a-c). In an aspect, the ablation catheter 20 can use a plurality of high impedance structures 540. The high impedance structures 540 are configured to intersect the theoretic field lines 550 (see FIGS. 48-49) created by two bipolar electrodes 530 by creating an obstacle to a baseline current flow. For example, in a homogeneous conductor such as seawater or blood plasma, the predicted current path will follow the shortest path (i.e., the current will follow the path of least resistance), as shown in FIG. 48. By placing a high impedance structure 540 between adjacent electrodes 530, the current contour 550, as shown in FIG. 49, can be distorted by the contours of the high impedance structure 540, with the current density decreasing linearly between the electrodes 530 but increasing orthogonally along the surface of the high impedance structure 540. FIGS. 50-51 show an axial perspective of the change of the location of the current density 544 of a coaxially cylindrical insulator 540 relative to the insulator circumference. As shown in FIG. 50, when the circumference of the insulator/high impedance structure 540 is small, the current density 544 is approximate the surface of the electrode 530. However, as the high impedance structure 540 expands, the current density 544 becomes located further from the surface of the electrode 530.

Figure 52A:
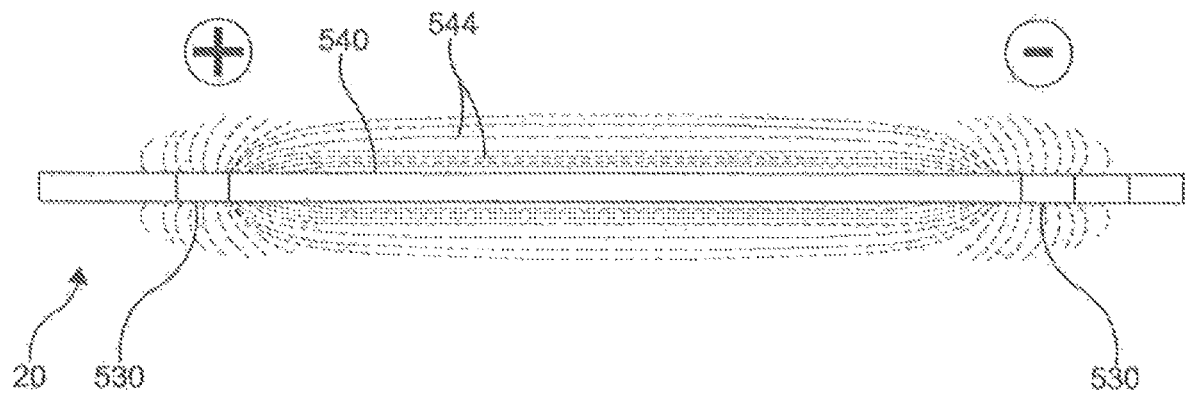
FIGS. 52a-c is a schematic representation of an ablation catheter with electrodes and a high impedance structure according to an aspect.
Figure 52B:
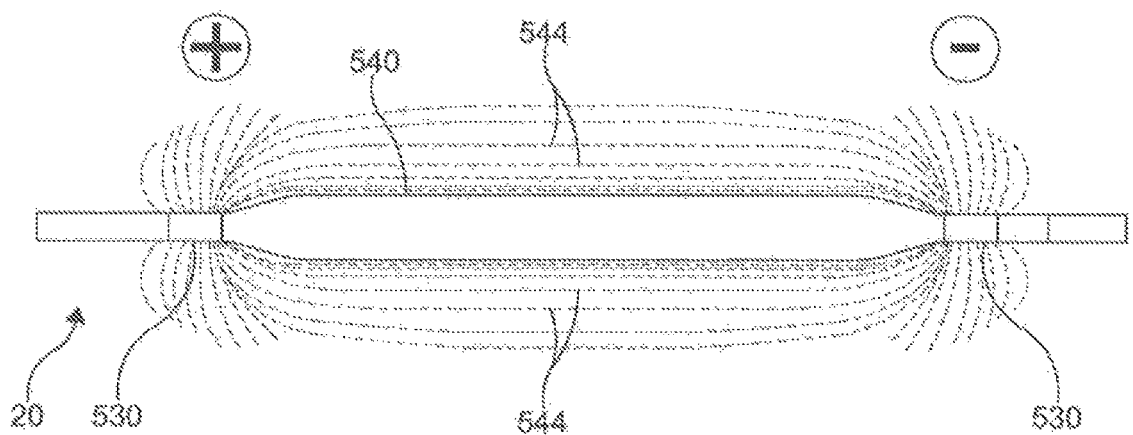
Figure 52C:
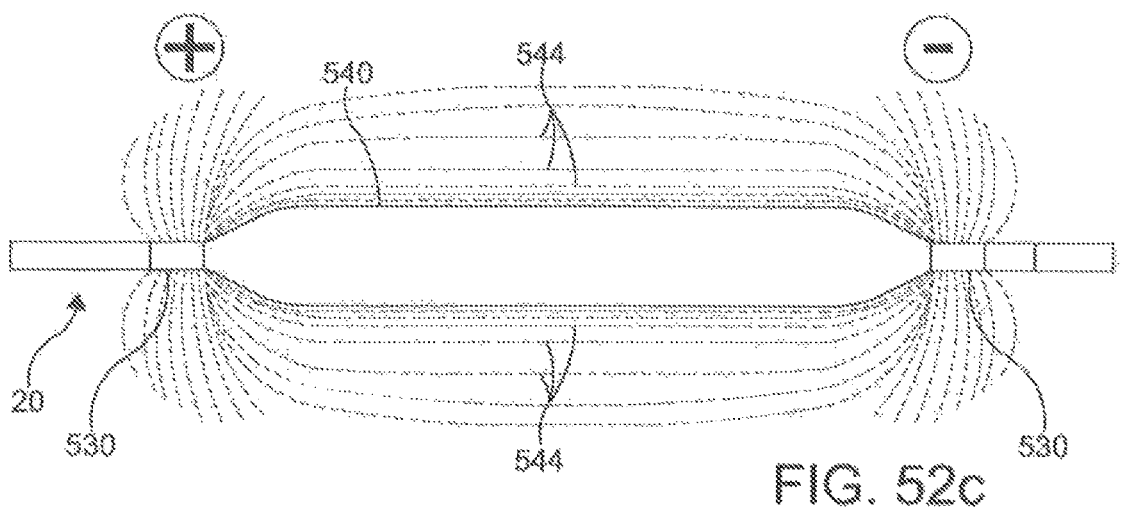

In exemplary aspects, the shape, and more specifically the height of the high impedance structure 540 relative to the axis 502 of the ablation catheter 20, is adjustable. For example, the high impedance structure 540 comprises an inflatable balloon 540 made of a suitable nonporous material with high dielectric constantan (i.e., effectively an electric insulator). The inflatable balloon 540 is coaxially situated between two electrodes 530, as shown in FIG. 52a-c. As the inflatable balloon 540 is inflated, the current density 544 along the surface of the balloon will decrease linearly while the relative current density 544 at an arbitrary point between the electrodes 510 and orthogonally remote from the axis 502 of the ablation catheter 20 increases. The adjustment of the inflatable balloon 540 provides a way to project and or direct the electric field along an orthogonal/radial vector to increase the current density 544. While the exemplary aspect utilizes a balloon 540 to provide low profile delivery, other articulated, fixed and/or mechanical high impedance structures 540, including a wide variety of insulators, can be employed. Further, it is preferable that the high impedance structures 540 are controllably adjustable, for the reasons discussed below.

The current density at the surface of the cylindrical insulator symmetrical positioned between two ring electrodes is geometrically related to the radius of the cylinder. In such an exemplary aspect can be determined by the following formula:

$$J=J_i(\Pi r^2 * 1_{ii})i/((\Pi r^2 * 1_i)_2-(\Pi r^2 * 1_i)_i)$$

where J is the resulting density, $J_i$ is the initial density, $(\Pi r^2 * 1_i)_i$ is the initial area of the high impedance structure before activation, and $(\Pi r^2 * 1_i)_2$ is the area of the high impedance structure after activation.

In our exemplary aspect, the electrical conductivity ranges 50-100 S/M (conductivity σ is defined as the ratio of the current density J to the electric field strength E). (J=Sigma.E). The predicted electric field strength at the surface of the insulator balloon 540 (represented by A in FIGS. 48-49) will be related to the current density/conductivity of the environment.

Positioning of the high impedance structure or insulator 540 between the dipole formed from adjacent electrodes 530 will change the contour of the current path and increase the relative electric field strength at point A, as shown in FIGS. 48-49. The shape of the high impedance structure 540 can be varied to project/amplify the relative the current orthogonal to the axis 502 of the ablation catheter 20. Other shapes and materials can be uses as high in combination with high impedance structures/insulators 540 to focus the current asymmetrically or to isolate the current source form the target tissue. In an aspect, the high impedance structure or insulator 540 can comprise an insulator balloon 540 configured to expand off center to provide a preferential path for current ipsilateral to the shorter axis's.

In other aspects, the high impedance structure or insulator 540 can be constructed to geometrically isolate current from one source electrode 530 from untargeted nearby structures but allow the current to travel through a fenestration or other geometrically oriented opening, there by changing the current density. In a simple example, a balloon when expanded would partially cover the electrodes 530 while creating a prescribed tunnel for the current to travel through. In an aspect, an asymmetrical balloon 530 can focus current along the path of least resistance (generally the shortest linear distance). In another aspect, an expanding mesh high impedance structure 530 can surround the electrode 530 to safely increase current at that electrode 530 with less risk of unwanted collateral damage by simply maintaining a prescribed distance from soft tissues. Such a high impedance structure allows an increase current density at one end of a bipole near an ablation target while protecting structures at the counterpoint. The use of geometric high impedance structures or insulators 540 to contour the current path of a current created between dipole electrodes 530 within a conductive media such as tissue could be used to precisely deliver electrical ablation or stimulus energy to targeted tissues adjacent to the high impedance structure 540.

While the combination of the electrodes 530 and the high impedance structures 540 are directed to deliver high voltage ultra short ablation impulses in the pericardial/epicardial space for the purpose of treating cardiac arrhythmia, there is an immediate implication for other ablation procedures using the electrode 530/high impedance structures 540 for contouring ablation energy to vascular walls (in stent restenosis) and/or contour the virtual electrode 530 in ablation procedures targeting solid tumors and/or prostatic hypertrophy. While balloon catheters are known in the art for the purpose of providing mechanical force, geometric stabilization, and or the delivery of ablation energy such a laser light or ultrasound, the combination of electrodes 530 and high impedance structures 540 oriented on a ablation catheter 20 is fundamentally distinct as the ablation catheter 20 uses the high impedance structures 540 to shape the electric current used in an in vivo therapy.

It is contemplated that the independent electrodes 530 can be assigned polarity individually or in groups. Depending on these polarity assignments, it is contemplated that the relative orientation of the electrical impulses and the virtual electrode properties (e.g., the surface area and thus control current density) of the electrodes 530 can be selectively adjusted. In exemplary aspects, the plurality of electrodes 530 of the ablation catheter 20 can be connected to a routing console/switchboard 610 outside the body where the electrodes 530 can be assigned a role as a recording electrode, an active pacing, and/or an ablation electrode, as discussed above. The console 610, in turn, can be operatively coupled to a computer-controlled signal generator 700 and recording console 650. In an aspect, the electrode polarity assignments can be changed as needed to achieve one or more desired effects. By changing the relative polarity assignments of the electrodes 530, at least one of the virtual electrode shape and the current density can be selectively varied.

Figure 53A:
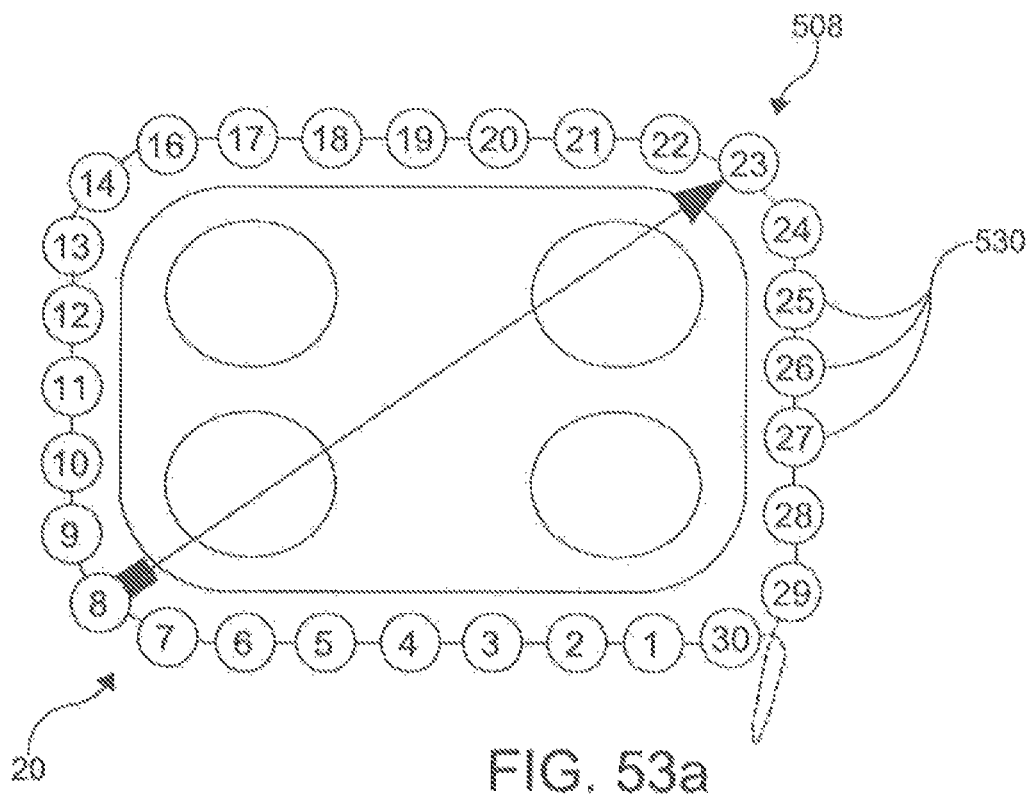
FIGS. 53a-d display exemplary electrode assignments according to an embodiment.

In another aspect, the ablation energy can be delivered to a single electrode 530 or to multiple electrodes 530 simultaneously. In an aspect, FIGS. 53a-d display an array of d exemplary electrode 530 assignments. FIG. 53a illustrates an extended bipolar arrangement with equal current density between electrodes 8 and 23. The selected electrodes 8 and 23 can deliver an ablation impulse for every cardiac cycle, changing the active bipoles with every cardiac cycle in a step-wise manner. In an example, if the heart is paced at a 500 ms cycle length the circumferential linear lesion will be delivered in 7.5 seconds.

Figure 53B:
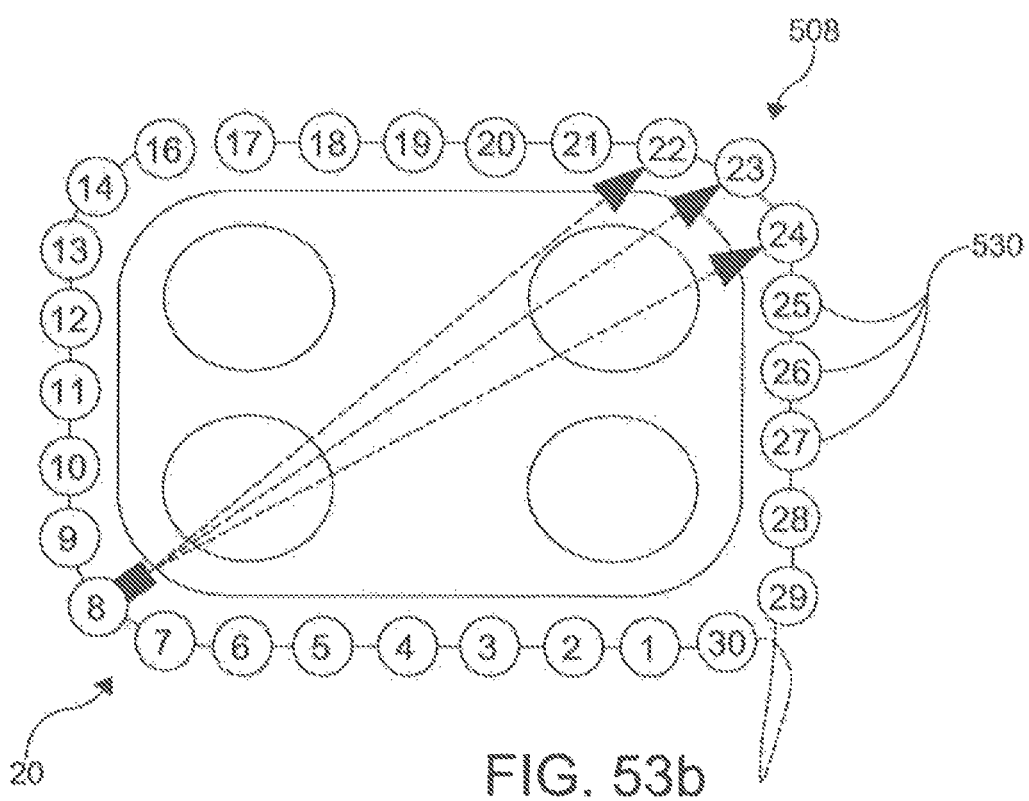

FIG. 53b illustrates an extended bipolar arrangement with asymmetric current density, wherein electrode 8 is assigned a different polarity than electrodes 22, 23, and 24. This assignment decreases the current density at one of the bipoles to reduce injury to bystander structures near the pole.

Figure 53C:
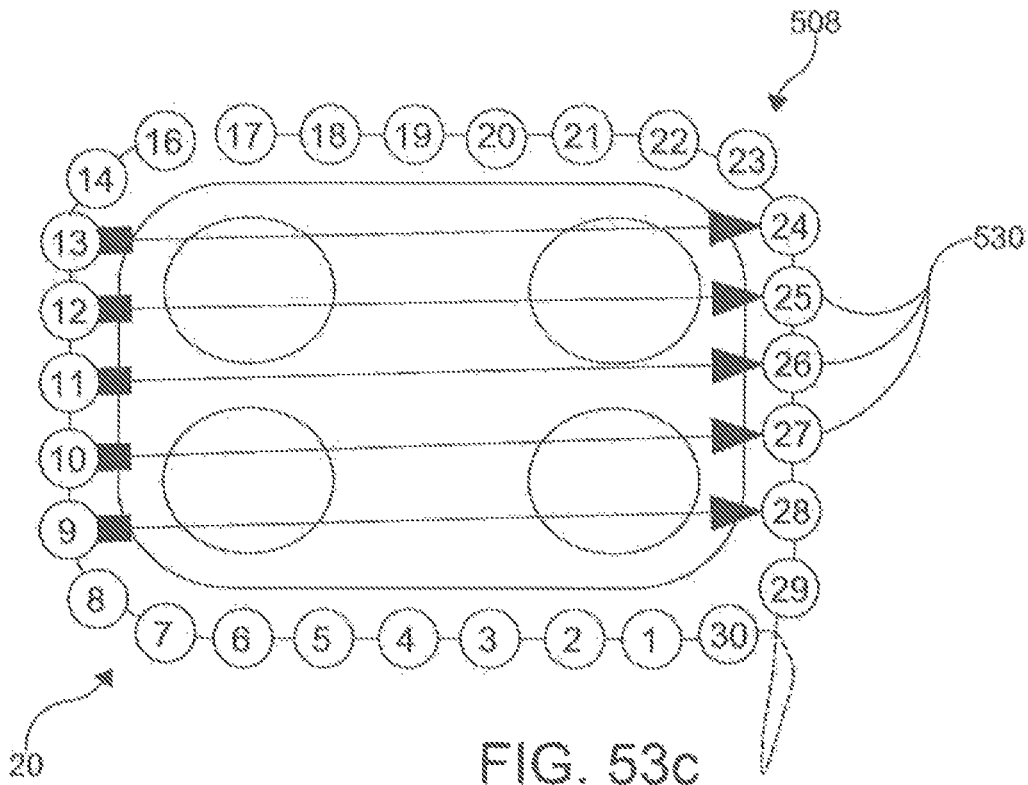

FIG. 53c illustrates an extended bipolar arrangement with equal current density but activated as a simultaneous array. As illustrated, electrodes 9-13 are assigned one polarity, whereas electrodes 24-28 are assigned another. The electrodes 530 are activated simultaneously to form complimentary arrays. This could be employed in cases where sub straight accommodated more rapid ablation sequencing (2-3 cycle lengths).

Figure 53D:
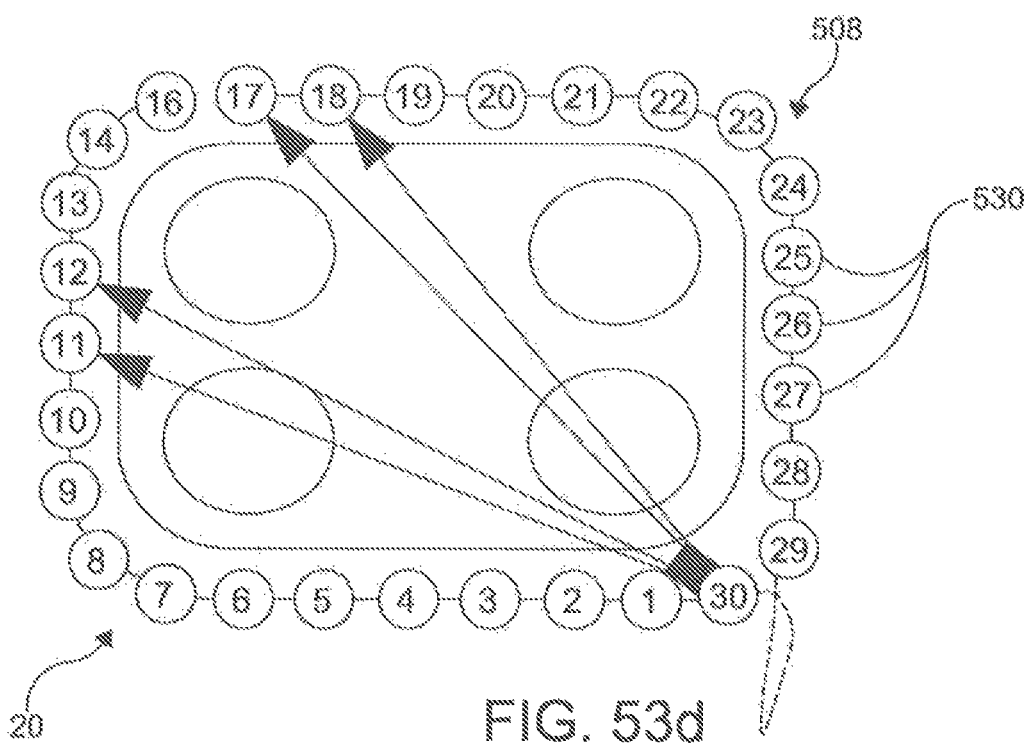

An extended bipolar arrangement with asymmetric current density is illustrated in FIG. 53d. As shown, electrodes 11, 12, 17, and 18 are assigned a polarity different from electrode 30, which creates an extended bipolar arrangement with a gap in the complementary electrode array. Such an arrangement can be used to avoid inadvertent ablation of a vulnerable bystander structures, including the phrenic nerve.

It is still further contemplated that the impulses can be delivered in a programmed manner, triggered by feedback from a bio-potential or physiologic signal (such as respirations, nerve impulses, fluctuations in blood pressure, and/or the cardiac action potential) or an outside event.

In exemplary applications, as described above, the ablation catheter 20 can be deployed such that both the proximal portion 506 and distal portion 510 of the elongate shaft 500 are external to the body (the central portion 508 of the catheter with the multi-electrode array remains internal). However, in additional applications, it is contemplated that the ablation catheter 20 can be customized to take advantage of target anatomy; in some cases, the distal portion 510 of the ablation catheter 20 can remain in the body, and a remote electrode can be used to complete the ablation procedure.

In exemplary applications, the ablation catheter 20 can be employed in a catheter-based epicardial atrial fibrillation ablation procedure performed in a closed pericardium. In this atrial fibrillation ablation procedure, the ablation catheter 20 can be advanced over a guide wire 300 that has already been positioned around the epicardial left atrial structures. Thus, the ablation catheter 20 can be deployed into the pericardial space from a subxiphoid or apical percutaneous approach, as discussed above.

It is contemplated that the guide wire 300 can be delivered around the left atrium by using the percutaneous catheter system 10 described herein to puncture through two key anatomic obstacles (pericardial reflections near the vena cava and the right pulmonary veins). Using this method, the guide wire 300 can enter the pericardium and then travel under the inferior-lateral left ventricle, along the lateral left atria, into the transvers sinus, along the roof of the left atria, between the right superior pulmonary vein and superior vena cava (SVC) through a pericardial puncture site. Then, the guide wire 300 can travel along the right lateral aspect of the left ventricle, between the right inferior pulmonary vein and inferior vena cava (IVC), traveling through the second pericardial puncture into the obtuse sinus under the posterior left atria. The guide wire 300 can then extend under the ventricle and out of the pericardium such that both ends of the guide wire 300 are outside the body. Once the guide wire 300 has been positioned, the ablation catheter 20 can be advanced along the guide wire 300. From this advantageous position, the ablation energy can be delivered directly to the key left atrial ablation targets, thereby creating a circumferential lesion without the need for repositioning the ablation catheter 20 or entering the left atrial blood pool. However, the ablation catheter 20 can be repositioned to perform other targeted epicardial ablations, including, for example and without limitation, ablation of autonomic ganglia or creation of additional linear ablation lesions.

In an aspect a goal of the disclosed ablation procedure can be the electrophysiological isolation/decoupling of key segments of the heart (e.g., the left atrium and the ostia of the pulmonary veins) that are thought to be involved in the genesis and/or maintenance of atrial fibrillation. The disclosed percutaneous catheter system 10 and ablation catheter 20, and the associated ablation catheter system 600, can provide means for creating a "box" lesion around ostia of the pulmonary veins without the need to enter the arterial blood pool. In use, after the ablation catheter 20 is deployed over the guide wire 300, one or more electrodes 530 of the plurality of electrodes 530 of the ablation catheter 20 can be used to measure local electrograms and/or deliver mapping stimuli. Using an extended bipolar arrangement of the electrodes 530, the directional electrograms adjacent to the electrodes 530 can be assessed to permit identification of changes in the substrate and local conduction block. As further described herein, the ablation catheter 20 can be connected to one or more impulse generators 700 and a routing console 610. It is contemplated that the operator can select an electrode configuration to optimize the vector of current for each segment of the lesion. In exemplary aspects, the procedure can be at least partially computer-automated while requiring at least some input from the operator to identify a preferred current vector. The impulse generator 700 can then deliver ablative energy to the electrodes 530 of the ablation catheter.

In exemplary applications, the ablation catheter 20 can be configured to deliver high intensity ultra-short duration impulses/IE to produce a transmural lesion. In an aspect, the IE impulses can be delivered by the electrodes 530 in synchrony with the cardiac cycle (e.g., from about 200 ms to about 300 ms after detection of a QRS complex) to reduce the chance of inducing arrhythmias. In an aspect, the impulse strength, duration, duty cycle and timing of the IE impulses can be selectively adjusted to tailor the ablation characteristics in real time. In such an aspect, the real-time adjustments can be required to address changes in tissue conductance as the lesion evolves. In exemplary aspects, the power can be adjusted to maintain a constant current density in the virtual electrode, thereby reducing the tissue conductance. In such aspects, the tissue conductance can be measured between impulses and integrated into an automated feedback circuit. In such aspects, the impulse strength can be adjusted to electroporation impulses using a standard unipolar configuration or an extended bipolar configuration.

Irreversible electroporation (IE) is a non-thermal ablation technique that can be advantageously used within the pericardial space. IE works by delivery on ultra-short (nanoseconds) high voltage (100-10,000V) impulses that cause very brief disruption in the membrane of cells. The disruption in the lipid bilayer leads to cell death through necrosis or apoptosis, depending on the field strength involved. In exemplary aspects, the ablation catheter 20 can permit customization of the direction of ablation energy within the pericardium. When compared to RF ablation, IE ablation can produce a lesion that follows a geometric pattern more closely approximating the contours of the virtual electrode 530. In such an aspect, the ablation catheter 20 can take advantage of these electrophysiologic properties to create a more focal lesion that directs the vector of current toward the target and also reduces the risk of unintended collateral injury. Although RF ablation using the same extended bipolar technique shows directionality, local tissue heating can reduce the current vector effect. (See FIG. 26). Additionally, the IE ablation can leave the intracellular matrix of tissue relatively undistorted, thereby reducing the risk of structural tissue instability, rupture, and fistula formation; there is typically limited or no opportunity for "char" formation on the electrode, so it generally will not need to be removed, cleaned, or redeployed. Because nerve fibers are particularly resistant to injury from IE techniques, IE ablation can reduce the risk of damage to nearby phrenic nerves. IE ablation can produce effective lesions in a fraction of the time required to create a transmural lesion by RF techniques. In exemplary aspects, IE impulses can be delivered via the ablation catheter 20 through the electrodes 530 in an automated fashion in a variety of extended bipolar orientations to create the complete linear circumscribing lesion in less than 1/10th the time it would take to produce the same lesion set using RF ablation techniques. IE ablation techniques are not dependent on tissue thermodynamics, thereby improving the chance of creating a full thickness lesion. Thermal techniques such as resistive heating from RF energy can be less effective because conductive cooling properties of the blood pool can protect the endocardium. In an aspect, IE ablation techniques can be selectively tuned to create lesions by apoptosis (as opposed to necrosis), leaving a very clean scar with less local inflammation.

In exemplary configurations, the ablation catheter system 600 can comprise the ablation catheter 20 and a routing console 610 that is linked to a commercially available signal generator 700 which is capable of arbitrary electrical waveform generation, including simple DC stimulus, radiofrequency monophasic and biphasic impulse generation, and high voltage ultra short impulse generation.

In use, after an operator has positioned a guide wire 300 around the left atrium, the ablation catheter 20 can be advanced over the guide wire 300 so that the array of electrodes 530 (located at the central portion 508 of the elongate shaft 500) now surrounds the left atrium. The distal portion 510 of the ablation catheter 20 can extend outside the body of the subject and be passed through the means for applying tension 524 (e.g., a loop tensioner 524), as further described herein. The loop tensioner 524 can then be advanced over the proximate portion 506 and distal portion 510 of the ablation catheter 500 to provide lateral tension and create a closed loop around the left atrial target structures. The guide wire 300 can then be removed to provide more flexibility and improved tissue contact along the left atrial contours. Small adjustments can be made using the loop tensioner 524 and/or a variety of custom styluses 524 that can be inserted into the catheter wire lumen 512/514. Once a desired position of the electrodes 530 of the ablation catheter 20 around the targeted tissue region is achieved, it is contemplated that the ablation catheter 20 will not need to be repositioned.

The operator can then conduct a limited electrophysiologic study, checking left atrial pacing thresholds and local electrocardiograms. The operator can then evaluate the radiographic orientation of the electrodes 530 around the left atrium and assign a polarity to the each respective electrode 530. Optionally, this assignment procedure can be partially automated to reduce the total steps needed to create and optimal extended bipolar vector. The tissue conductance and impedance can be measured at each electrode 530 at baseline. In an aspect, these measurements can be performed in an automated procedure performed by an automated recorder and potentially integrated into the control algorithm to make voltage adjustments, and/or can be performed manually by the operator. These baseline measurements can be periodically re-measured to assess local ablation effects. The data can be used to adjust the applied ablation energy in an automated fashion when such automated functions are available. It is contemplated that each electrode 530 of the plurality of electrodes 530 of the ablation catheter 20 can be used to monitor, pace and/or deliver energy for ablation. In exemplary aspects, the ablation energy can be delivered to the plurality of electrodes 530 using a programed computerized protocol synchronized with the cardiac cycle of the subject. In exemplary applications, the operator can selectively initiate a sequence activating each electrode 530 individually and/or in series.

It is contemplated that the linear ablation should be completed in less than about 60 seconds (depending on the baseline heart rate and total length of the linear lesion being created). In the exemplary system we will overdrive pace the heart at a rate between 100 and 120 beats per minute. In order to deliver ablation pulses or train of pulses to each electrode we will discharge the device n*½ times the number of electrodes in the array. In our example we use 30 electrodes therefor a completed cycle will take 7.5 seconds. Conceivably the entire procedure could be performed in 7.5 milliseconds with commercially available solid-state high voltage relays.

In an aspect, an electrophysiologic study of conduction block can be performed without any repositioning of the ablation catheter 20. The operator can perform a programed stimulus protocol to identify gaps in the linear lesion. In the example the operator would perform an electrophysiologic study prior to the ablation. The principal maneuver would be to measure the pacing threshold at each point along the ablation catheter 20. The electrodes 530 of the ablation catheter 20 can be used for measuring the pacing threshold, or other pacing measuring devices can be used. After the ablation is delivered the operator could retest the capture threshold. The anticipated results would be an increase in the local pacing threshold. Furthermore a more standard electrophysiologic study can be performed using pacing electrodes in the pericardial space and/or standard diagnostic electrophysiologic catheters in the right atria, coronary sinus and right ventricle. Conformation that the pulmonary veins are electrically uncoupled from the rest of the left atria is a standard clinical practice. Atrial pacing form inside the lesion boundary can be performed using a remote stimulus electrode, which can optionally be a part of the loop tensioner 524. When there is evidence of conduction outside the lesion (as evidenced by capture of the atria), the operator can evaluate the local electrograms to identify potential gaps in the lesion. It is contemplated that the extended bipolar arrangement of the electrodes 530 can be useful in determining timing and direction of local depolarization. Electrodes overlaying these potential incomplete ablation sites can be identified and additional energy can be delivered as needed.

Once complete electrophysiologic block around the pulmonary veins is verified, it is further contemplated that the ablation catheter 20 can also be used to evaluate autonomic ganglia that are common along this path. These potential targets can be identified with neuro-stimulus techniques and evaluation of epicardial signals. The operator can choose to deliver RF ablation to these select sites, if desired. After the ablation is complete, it is contemplated that the ablation catheter 20 can be removed or repositioned to create lesions at additional ablation target sites.

As described herein, the ablation catheter 20 is an over-the-wire ablation catheter with an array of multiple electrodes 530 located on its mid (central) portion 508. The ablation catheter 20 can be more flexible than other clinically available catheter-based ablation devices to permit tissue contact around the left atrial structures. The electrodes 530 can be capable of monitoring and/or delivering RF energy, electroporation impulses, and programed cardiac pacing and/or neuro-stimulus. The ability of the disclosed ablation catheter 20 to individualize the as-extended bipolar electrode 530 can take advantage of the natural geometry inside the pericardial space to deliver energy to a series of electrodes arranged around the target structure.

In use, once the ablation catheter 20 is deployed, it is contemplated that a linear lesion can be created without need to reposition the catheter 20. It is further contemplated that the ablation catheter 20 can provide a stable and contiguous array of electrodes 530 along the target path that can deliver ablation energy and can also be used to confirm electrophysiologic block using an extended bipolar electrocardiographic technique. It is contemplated that the use of high impedance structures 540 positioned along the bipolarly aligned electrodes can further adjust the density of the current applied. It is contemplated that the ability to perform the entire procedure without repositioning of the ablation catheter 20 can save time and potentially make this approach more effective than standard point-by-point techniques, which often require frequent repositioning and/or advanced noncontact mapping techniques to identify incomplete segments in the ablation lesion. For epicardial techniques performed from the pericardial space, such manipulation is fraught with danger and technical limitations. The disclosed ablation catheter 20 takes advantage of the natural contours of the left atrial epicardial surface to provide reliable and stable electrode contact.

As will be appreciated by one skilled in the art, the methods and systems described above in relation to the ablation catheter system 600 may take the form of an entirely hardware embodiment, an entirely software embodiment, or an embodiment combining software and hardware aspects. Furthermore, the methods and systems may take the form of a computer program product on a computer-readable storage medium having computer-readable program instructions (e.g., computer software) embodied in the storage medium. More particularly, the present methods and systems may take the form of web-implemented computer software. Any suitable computer-readable storage medium may be utilized including hard disks, CD-ROMs, optical storage devices, or magnetic storage devices.

Some embodiments of the methods and systems discussed above and below can be described with reference to block diagrams and flowchart illustrations of methods, systems, apparatuses and computer program products. It will be understood that each block of the block diagrams and flowchart illustrations, and combinations of blocks in the block diagrams and flowchart illustrations, respectively, can be implemented by computer program instructions. These computer program instructions may be loaded onto a general purpose computer, special purpose computer, or other programmable data processing apparatus to produce a machine, such that the instructions which execute on the computer or other programmable data processing apparatus create a means for implementing the functions specified in the flowchart block or blocks.

These computer program instructions may also be stored in a computer readable memory that can direct a computer or other programmable data processing apparatus to function in a particular manner, such that the instructions stored in the computer-readable memory produce an article of manufacture including computer-readable instructions for implementing the function specified in the flowchart block or blocks. The computer program instructions may also be loaded onto a computer or other programmable data processing apparatus to cause a series of operational steps to be performed on the computer or other programmable apparatus to produce a computer-implemented process such that the instructions that execute on the computer or other programmable apparatus provide steps for implementing the functions specified in the flowchart block or blocks.

Accordingly, blocks of the block diagrams and flowchart illustrations support combinations of means for performing the specified functions, combinations of steps for performing the specified functions and program instruction means for performing the specified functions. It will also be understood that each block of the block diagrams and flowchart illustrations, and combinations of blocks in the block diagrams and flowchart illustrations, can be implemented by special purpose hardware-based computer systems Thal perform the specified functions or steps, or combinations of special purpose hardware and computer instructions.

Figure 44:
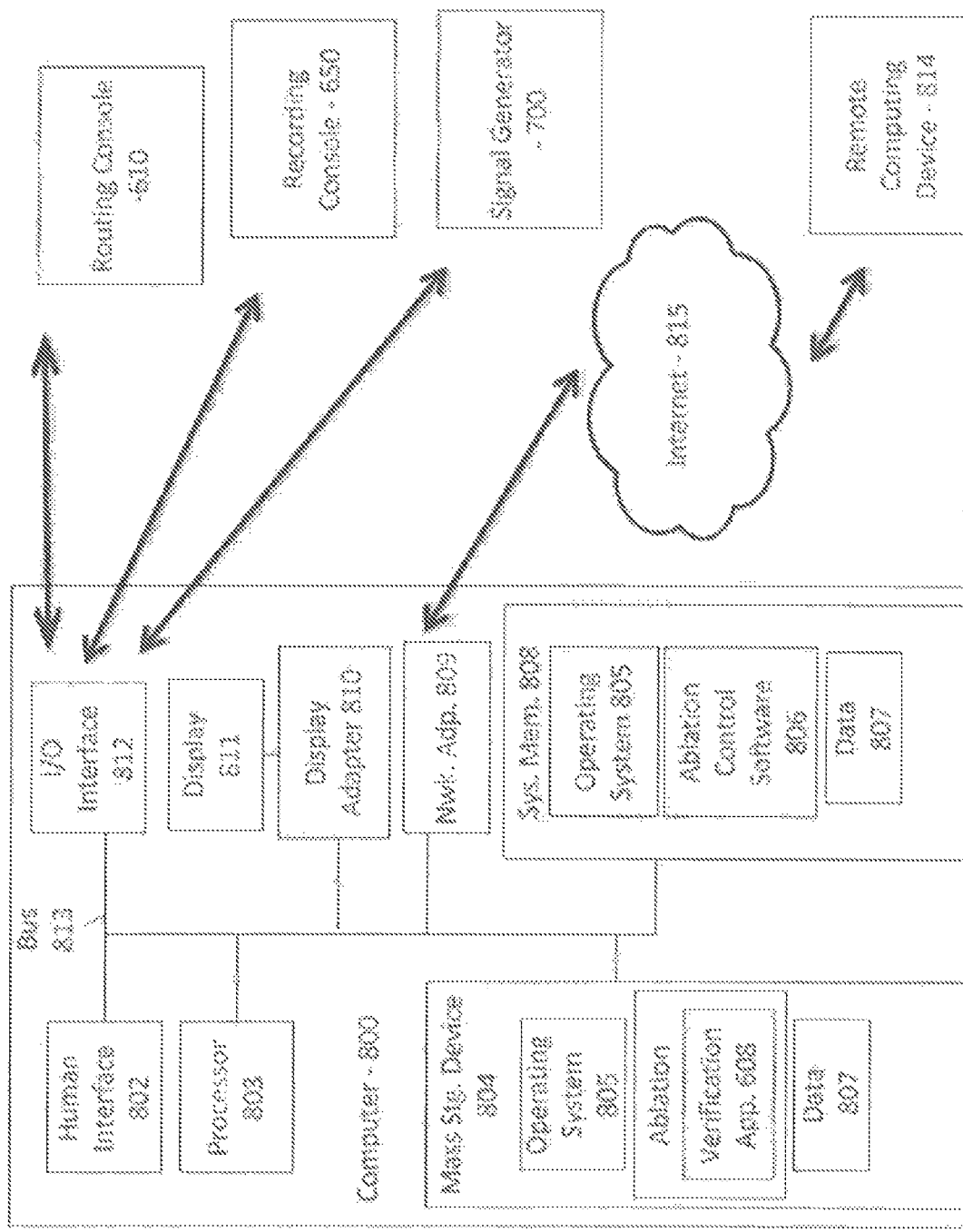
FIG. 44 is a block diagram of an exemplary computer system according to an aspect.

The methods and systems that have been introduced above, and discussed in further detail below, have been and will be described as comprised of units. One skilled in the art will appreciate that this is a functional description and that the respective functions can be performed by software, hardware, or a combination of software and hardware. A unit can be software, hardware, or a combination of software and hardware. The units can comprise the ablation control software 806 as illustrated in FIG. 44 and described below. In one exemplary aspect, the units can comprise a computer 800 as illustrated in FIG. 44 and described below.

FIG. 44 is a block diagram illustrating an exemplary operating environment for performing the disclosed methods. This exemplary operating environment is only an example of an operating environment and is not intended to suggest any limitation as to the scope of use or functionality of operating environment architecture. Neither should the operating environment be interpreted as having any dependency or requirement relating to any one or combination of components illustrated in the exemplary operating environment.

The present methods and systems can be operational with numerous other general purpose or special purpose computing system environments or configurations. Examples of well known computing systems, environments, and/or configurations that can be suitable for use with the systems and methods comprise, but are not limited to, personal computers, server computers, laptop devices, and multiprocessor systems. Additional examples comprise set top boxes, programmable consumer electronics, network PCs, minicomputers, mainframe computers, distributed computing environments that comprise any of the above systems or devices, and the like.

The processing of the disclosed methods and systems can be performed by software components. The disclosed systems and methods can be described in the general context of computer-executable instructions, such as program modules, being executed by one or more computers or other devices. Generally, program modules comprise computer code, routines, programs, objects, components, data structures, etc. that perform particular tasks or implement particular abstract data types. The disclosed methods can also be practiced in grid-based and distributed computing environments where tasks are performed by remote processing devices that are linked through a communications network. In a distributed computing environment, program modules can be located in both local and remote computer storage media including memory storage devices.

Further, one skilled in the art will appreciate that the systems and methods disclosed herein can be implemented via a general-purpose computing device in the form of a computer 800. The components of the computer 800 can comprise, but are not limited to, one or more processors or processing units 803, a system memory 808, and a system bus 813 that couples various system components including the processor 803 to the system memory 808. In the case of multiple processing units 803, the system can utilize parallel computing.

The system bus 813 represents one or more of several possible types of bus structures, including a memory bus or memory controller, a peripheral bus, an accelerated graphics port, and a processor or local bus using any of a variety of bus architectures. By way of example, such architectures can comprise an Industry Standard Architecture (ISA) bus, a Micro Channel Architecture (MCA) bus, an Enhanced ISA (EISA) bus, a Video Electronics Standards Association (VESA) local bus, an Accelerated Graphics Port (AGP) bus, and a Peripheral Component Interconnects (PCI), a PCI-Express bus, a Personal Computer Memory Card Industry Association (PCMC1A), Universal Serial Bus (USB) and the like. The bus 813, and all buses specified in this description can also be implemented over a wired or wireless network connection and each of the subsystems, including the processor 803, a mass storage device 804, an operating system 805, ablation control software 806, data 807, a network adapter 809, system memory 808, an Input/Output Interface 812, a display adapter 810, a display device 811, and a human machine interface 802, can be contained within one or more remote computing devices 814 at physically separate locations, connected through buses of this form, in effect implementing a fully distributed system.

The computer 800 typically comprises a variety of computer readable media. Exemplary readable media can be any available media that is accessible by the computer 800 and comprises, for example and not meant to be limiting, both volatile and non-volatile media, removable and non-removable media. The system memory 808 comprises computer readable media in the form of volatile memory, such as random access memory (RAM), and/or non-volatile memory, such as read only memory (ROM). The system memory 808 typically contains data such as data 807 and/or program modules such as operating system 805 and ablation control software 806 that are immediately accessible to and/or are presently operated on by the processing unit 803.

In another aspect, the computer 800 can also comprise other removable/non removable, volatile/non-volatile computer storage media. By way of example, FIG. 1 illustrates a mass storage device 804 which can provide non-volatile storage of computer code, computer readable instructions, data structures, program modules, and other data for the computer 800. For example and not meant to be limiting, a mass storage device 804 can be a hard disk, a removable magnetic disk, a removable optical disk, magnetic cassettes or other magnetic storage devices, flash memory cards, CD-ROM, digital versatile disks (DVD) or other optical storage, random access memories (RAM), read only memories (ROM), electrically erasable programmable read-only memory (EEPROM), and the like.

Optionally, any number of program modules can be stored on the mass storage device 804, including by way of example, an operating system 805 and ablation control software 806. Each of the operating system 805 and ablation control software 806 (or some combination thereof) can comprise elements of the programming and the ablation control software 806. Data 807 can also be stored on the mass storage device 804. Data 807 can be stored in any of one or more databases known in the art. Examples of such databases comprise, DB20, Microsoft® Access, Microsoft® SQL Server, Oracle®, mySQL, PostgreSQL, and the like. The databases can be centralized or distributed across multiple systems.

In another aspect, the user can enter commands and information into the computer 800 via an input device (not shown). Examples of such input devices comprise, but are not limited to, a keyboard, pointing device (e.g., a "mouse"), a microphone, a joystick, a scanner, tactile input devices such as gloves, and other body coverings, and the like. These and other input devices can be connected to the processing unit 803 via a human machine interface 802 that is coupled to the system bus 813, but can be connected by other interface and bus structures, such as a parallel port, game port, an IEEE 1394 Port (also known as a Firewire port), a serial port, or a universal serial bus (USB).

In yet another aspect, a display device 811 can also be connected to the system bus 813 via an interface, such as a display adapter 810. It is contemplated that the computer 800 can have more than one display adapter 810 and the computer 800 can have more than one display device 811. For example, a display device can be a monitor, an LCD (Liquid Crystal Display), or a projector. In addition to the display device 811, other output peripheral devices can comprise components such as speakers (not shown) and a printer (not shown) which can be connected to the computer 800 via Input/Output Interface 812. Any step and/or result of the methods can be output in any form to an output device.

Such output can be any form of visual representation, including, but not limited to, textual, graphical, animation, audio, tactile, and the like. Likewise, the routing console 610, recording console 650, and signal generator 700 can communicate with the computer 800 and its components through the Input/Output Interface 812.

The computer 800 can operate in a networked environment using logical connections to the routing console 610, recording console 650, and signal generator 700 and/or to one or more remote computing devices 814. By way of example, a remote computing device can be a personal computer, portable computer, a server, a router, a network computer, a wireless connected tablet or mobile device, a peer device or other common network node, and so on. Logical connections between the computer 800 and a remote computing device 814 can be made via a local area network (LAN) and a general wide area network (WAN). Such network connections can be through a network adapter 809. A network adapter 809 can be implemented in both wired and wireless environments. Such networking environments are conventional and commonplace in offices, enterprise-wide computer networks, intranets, cellular networks and the Internet 815.

For purposes of illustration, application programs and other executable program components such as the operating system 805 are illustrated herein as discrete blocks, although it is recognized that such programs and components reside at various times in different storage components of the computing device 800, and are executed by the data processor(s) of the computer. An implementation of ablation control software 806 can be stored on or transmitted across some form of computer readable media. Any of the disclosed methods can be performed by computer readable instructions embodied on computer readable media. Computer readable media can be any available media that can be accessed by a computer. By way of example and not meant to be limiting, computer readable media can comprise "computer storage media" and "communications media." "Computer storage media" comprise volatile and non-volatile, removable and non-removable media implemented in any methods or technology for storage of information such as computer readable instructions, data structures, program modules, or other data. Exemplary computer storage media comprises, but is not limited to, RAM, ROM, EEPROM, flash memory or other memory technology, CD-ROM, digital versatile disks (DVD) or other optical storage, magnetic cassettes, magnetic tape, magnetic disk storage or other magnetic storage devices, or any other medium which can be used to store the desired information and which can be accessed by a computer.

The methods and systems can employ Artificial Intelligence techniques such as machine learning and iterative learning. Examples of such techniques include, but are not limited to, expert systems, case based reasoning, Bayesian networks, behavior based AI, neural networks, fuzzy systems, evolutionary computation (e.g. genetic algorithms), swarm intelligence (e.g. ant algorithms), and hybrid intelligent systems (e.g. Expert inference rules generated through a neural network or production rules from statistical learning).

The proposed procedures are performed under conscious sedation and local anesthesia in a standard cardiac catheterization laboratory. The patient is prepped in the typical manner for an electrophysiologic study with an additional sterile field exposing the anterior chest and upper abdomen. Stimulus and mapping catheters are positioned in the RA, RV, and CS position. Percutaneous access to the pericardial space is achieved using a modified Seldinger technique or clinically available pericardial access tool. A small volume of iodinated contrast is injected into the pericardial space for visualization of key cardiac landmarks. The percutaneous track is expanded to accommodate catheter insertion. The clinical goal of the procedure will be to position a multi-electrode ablation catheter within the pericardial space for the purpose of ablation. The catheter will follow a course that circumferentially divides the more anterior left atrial structures from the pulmonary veins. Once in a stable position, the catheter's multi-electrode array will be used to deliver a single linear ablation lesion that can electrophysiologically isolate arrhythmogenic substrate of pulmonary veins from the greater left atrium.

As further described herein, it is contemplated that epicardial positioning the ablation catheter 20 can have mechanical advantages over endocardial multi-electrode arrays. The ablation catheter 20 can tailor the circumference of the loop formed by the elongate shaft 500 of the catheter 20 with little effort to provide full coverage. The flexibility of the ablation catheter 20 can provide a mechanism for secure tissue contact around complex anatomic geometry. It is further contemplated that the natural spatial limitation of the pericardial space provides a natural mechanism to assure electrode approximation. Furthermore, the risks of performing ablation from the epicardial surface place the ablation electrode 530 closer to some important bystander structures that necessitate the delivery of ablative energy with programed directional vectors. (See FIG. 23). With RF energy ablation, extended bipolar ablation can result in 40-50% deeper lesion in the direction of the programed vector. With IE ablation, the potential for creating a preferential directional injury vector can be greater because there is limited or no thermal energy. Typically, unipolar applications utilize an externalized grounding pad that results in a diffuse or spherical virtual electrode, while currently known bipolar ablation techniques typically utilize electrode pairs that are in very close proximity, require equipment is cumbersome, and require entry into both the pericardium and the left atrial blood pool.

In exemplary aspects, it is contemplated that the ablation catheter 20 can be modified to deliver gene therapy. In these aspects, it is contemplated that the elongate shaft 500 of the ablation catheter 20 can be modified to have irrigation side ports. It is further contemplated that a DNA or RNA vector can be delivered via the catheter using a tailored electroporation impulse.

In other exemplary aspects, it is contemplated that the ablation catheter 20 can be employed in a method for prostate ablation. In these aspects, it is contemplated that, in patients with benign prostatic hypertrophy and urinary obstruction, the ablation catheter 20 can be positioned to deliver irreversible electroporation impulses in an extended bipolar or unipolar configuration. High impedance structures 540 can be further utilized by the ablation catheter 20 in an extended bipolar configuration to increase the density current at targeted areas. In use, the ablation catheter can be advanced over a guide wire 300 that has been delivered into the bladder non-traumatically. It is contemplated that this technique can provide substantial advantages over current procedures, which are typically traumatic to the transitional endothelium of the urethra. With irreversible electroporation, it is contemplated that the impulse can be tailored to minimize inflammation and damage to the greater tissue architecture.

In other exemplary aspects, it is contemplated that the ablation catheter 20 can be used to preserve erectile function. In these aspects, the ablation catheter 20 can be used to ablate selected nerve axons.

In further exemplary aspects, it is contemplated that the ablation catheter 20 can be configured for therapy for solid tumors. Typically, current electroporation devises are created to place a pair of needle electrodes into the tumor using open and minimally-invasive surgical techniques. However, it is contemplated that the ablation catheter 20, with its over-the-wire electrode array, can be used in treating tumors which can be accessed through the vascular space (e.g., palliative therapy for renal cell carcinoma that is extending into the vena cava).

In still further exemplary aspects, it is contemplated that the ablation catheter 20 can be used to treat pulmonary hypertension where there is substantial endothelial remodeling and hypertrophy of the pulmonary vascular structures. In these aspects, the ablation catheter 20 can be used to "prune" the smooth muscle mass in these hypertrophied vessels and potentially lead to a favorable remodeling. It is contemplated that the electrodes of the ablation catheter 20 can be advanced around the hilum of the kidneys (using laparoscopic techniques) for purposes performing renal denervation and managing malignant refractory hypertension.

Although several embodiments of the invention have been disclosed in the foregoing specification, it is understood by those skilled in the art that many modifications and other embodiments of the invention will come to mind to which the invention pertains, having the benefit of the teaching presented in the foregoing description and associated drawings. It is thus understood that the invention is not limited to the specific embodiments disclosed hereinabove, and that many modifications and other embodiments are intended to be included within the scope of the appended claims. Moreover, although specific terms are employed herein, as well as in the claims which follow, they are used only in a generic and descriptive sense, and not for the purposes of limiting the described invention, nor the claims which follow.

What is claimed is:

1. A method, comprising:
   selecting, from a set of electrodes of a catheter, subsets of electrodes each including at least one first electrode configured to have a first polarity and at least one second electrode configured to have a second polarity opposite the first polarity, the catheter being positioned external to a heart of a subject such that a central portion of the catheter at least partially encircles left pulmonary veins and right pulmonary veins of the heart, the set of electrodes disposed on the central portion of the catheter;
   generating, via a signal generator, a pulsed waveform; and
   delivering the pulsed waveform to the subsets of electrodes along one or more current paths that each extend from at least one first electrode of a subset of electrodes through an endocardial space of the heart and to at least one second electrode of the subset of electrodes, such that the subsets of electrodes generate one or more electric fields that cause irreversible electroporation of tissue.

2. The method of claim 1, wherein each of the one or more current paths extends from at least one first electrode of a subset of electrodes, through a first wall portion of a left atrium of the heart, through the endocardial space of the heart, through a second wall portion of the left atrium of the heart, and to at least one second electrode of the subset of electrodes.

3. The method of claim 2, wherein the delivering the pulsed waveform causes irreversible electroporation of tissue in the first wall portion and the second wall portion of the left atrium to create a lesion.

4. The method of claim 2, wherein the delivering the pulsed waveform causes irreversible electroporation of tissue in a portion of the left atrium to create a circumferential lesion in the wall of the left atrium without repositioning the catheter.

5. The method of claim 2, wherein the delivering the pulsed waveform causes irreversible electroporation of tissue in a portion of the left atrium to create a lesion collectively around one or more of the left pulmonary veins and the right pulmonary veins formed in the left atrium.

6. The method of claim 1, wherein the pulsed waveform includes a set of biphasic impulses.

7. The method of claim 1, wherein the delivering the pulsed waveform includes delivering the pulsed waveform in synchronization with a cardiac cycle of the subject.

8. The method of claim 1, further comprising monitoring a cardiac cycle of the subject, the delivering the pulsed waveform including delivering the pulsed waveform in synchronization with the cardiac cycle of the subject.

9. The method of claim 1, further comprising monitoring a cardiac cycle of the subject using one or more electrodes of the set of electrodes, the delivering the pulsed waveform including delivering the pulsed waveform in synchronization with the cardiac cycle of the subject.

10. The method of claim 1, wherein the pulsed waveform includes one or more current impulses, the delivering the pulsed waveform including delivering the one or more current impulses for every heartbeat of the subject.

11. The method of claim 1, wherein the subsets of electrodes are first subsets of electrodes, the pulsed waveform is a first pulsed waveform, and the delivering the pulsed waveform causes irreversible electroporation of tissue in a first portion of the left atrium, the method further comprising:
    delivering a second pulsed waveform to a second subset of electrodes to cause irreversible electroporation of tissue in a second portion of the left atrium without repositioning the catheter.

12. The method of claim 1, further comprising:
    surgically creating an opening in a body of the subject to permit passage of the catheter; and
    positioning the catheter external to the heart of the subject prior to delivering the pulsed waveform.

13. The method of claim 1, wherein the central portion of the catheter is positioned in a pericardial space of the heart.

14. A method, comprising:
    identifying one or more intended current paths for delivering a pulsed waveform to a set of electrodes of a catheter, the catheter being positioned external to a heart of a subject such that a central portion of the catheter at least partially encircles left pulmonary veins and right pulmonary veins of the heart, the set of electrodes disposed on the central portion of the catheter, each of the one or more intended current paths extending through an endocardial space of the heart;
    selecting, from the set of electrodes and based on the one or more intended current vectors, subsets of electrodes each including at least one first electrode configured to have a first polarity and at least one second electrode configured to have a second polarity opposite the first polarity;
    generating, via a signal generator, a pulsed waveform; and delivering the pulsed waveform to the subsets of electrodes along one or more current paths corresponding to the one or more intended current paths, such that the subsets of electrodes generate one or more electric fields that cause irreversible electroporation of tissue.

15. The method of claim 14, wherein each of the one or more current paths extends from at least one first electrode of a subset of electrodes, through a first wall portion of a left atrium of the heart, through the endocardial space of the heart, through a second wall portion of the left atrium of the heart, and to at least one second electrode of the subset of electrodes.

16. The method of claim 15, wherein the delivering the pulsed waveform causes irreversible electroporation of tissue in the first wall portion and the second wall portion of the left atrium to create a lesion.

17. The method of claim 15, wherein the delivering the pulsed waveform causes irreversible electroporation of tissue in a portion of the left atrium to create a circumferential lesion in the wall of the left atrium without repositioning the catheter.

18. The method of claim 15, wherein the delivering the pulsed waveform causes irreversible electroporation of tissue in a portion of the left atrium to create a lesion collectively around one or more of the left pulmonary veins and the right pulmonary veins formed in the left atrium.

19. The method of claim 14, wherein the pulsed waveform includes a set of biphasic impulses.

20. The method of claim 14, wherein the delivering the pulsed waveform includes delivering the pulsed waveform in synchronization with a cardiac cycle of the subject.

* * * * *